US009636415B2

(12) United States Patent
Mudde et al.

(10) Patent No.: US 9,636,415 B2
(45) **Date of Patent: *May 2, 2017**

(54) BISPECIFIC MOLECULE BINDING TLR9 AND CD32 AND COMPRISING A T CELL EPITOPE FOR TREATMENT OF ALLERGIES

(71) Applicant: S-TARget therapeutics GmbH, Vienna (AT)

(72) Inventors: Geert Mudde, Vienna (AT); Gottfried Himmler, Vienna (AT)

(73) Assignee: S-TARGET THERAPEUTICS GMBH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/791,824

(22) Filed: Mar. 8, 2013

(65) Prior Publication Data

US 2013/0243767 A1 Sep. 19, 2013

Related U.S. Application Data

(63) Continuation-in-part of application No. 12/281,504, filed as application No. PCT/EP2007/001722 on Feb. 28, 2007, now abandoned.

(30) Foreign Application Priority Data

Mar. 3, 2006 (EP) .................................... 06110672

(51) Int. Cl.

| | |
|---|---|
| ***A61K 38/00*** | (2006.01) |
| ***A61K 48/00*** | (2006.01) |
| ***A61K 39/00*** | (2006.01) |
| ***A61K 39/385*** | (2006.01) |
| ***A61K 47/48*** | (2006.01) |
| ***C07K 14/47*** | (2006.01) |
| ***C07K 16/28*** | (2006.01) |
| ***A61K 39/35*** | (2006.01) |
| ***A61K 39/39*** | (2006.01) |

(52) U.S. Cl.

CPC .... *A61K 47/48369* (2013.01); *A61K 39/0008* (2013.01); *A61K 39/0011* (2013.01); *A61K 39/35* (2013.01); *A61K 39/385* (2013.01); *A61K 39/39* (2013.01); *C07K 14/4713* (2013.01); *C07K 14/4748* (2013.01); *C07K 16/28* (2013.01); *C07K 16/283* (2013.01); *C07K 16/2896* (2013.01); *A61K 2039/55561* (2013.01); *A61K 2039/6056* (2013.01); *C07K 2317/34* (2013.01); *C07K 2317/526* (2013.01); *C07K 2317/55* (2013.01); *C07K 2317/622* (2013.01); *C07K 2317/64* (2013.01); *C07K 2318/20* (2013.01)

(58) Field of Classification Search

None

See application file for complete search history.

(56) References Cited

FOREIGN PATENT DOCUMENTS

| | | |
|---|---|---|
| EP | 0 178 085 | 4/1986 |
| EP | 0 287 361 | 10/1988 |
| EP | 0640130 | 3/1995 |
| WO | WO/97/07218 | 2/1997 |
| WO | WO/03/035695 | 5/2003 |
| WO | PCT/EP2006/050059 | 7/2006 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491 ):471-473.*
Blumenthal et al. 'Definition of an Allergen.' Allergens and Allergen Immunotherapy. Ed. R Lockey, S. Bukantz and J. Bousquet. New York: Marcel Decker, 2004.37-50.*
Means et al. 'Human lupus autoantibody-DNA complexes activate DCs through cooperation of CD32 and TLR9.' J. Clin. Invest. 115(2);402-417, 2005.*
Davies et al. 'Immune complex processing in patients with systemic lupus erythematosis.' j. Clin. Invest. 90:2075=2083, 1992.*
Barton G M et al., "Intracellular localization of toll-like receptor 9 prevents recognition of self DNA but facilitates access to viral DNA," Nat Immunol, Jan. 2006;7(1):49-56.
Baselmans P J et al., 2000, Hum Immunol 61:789-798.
Beck H et al., 2001, Eur J Immunol 31:3726-3736.
Bheekha Escura R-. et al., Immunology, 1995, 86:343-350.
Bian H et al., 2003, Methods 29:299-309.
Bjersing J L et al., 2005, Immunobiology, vol. 210, No. 1, pp. 23-32.
Charbonnier A S, 2003, J Leukocate Biol, 73:91-99.
Chen W L et al., 2005, Immunol Lett, 98:153-159.
Chua K Y et al., 1991, Clin Exp Allergy, 21:161-166.
Eaton-Bassiri A et al., 2004, Infect Immun, 72:7202-7211.
Ebner C 1999, Int Arch Allergy Immunol, 119:1-5.
Ferreira F et al., 1998, FASEB Journal, 12:231-242.
Higgins J A et al., 1994, J Allergy Clin Immunol, 93:891-899.
Horejs-Hoeck J et al., 2005, Immunology, vol. 115, No. 3, pp. 407-415.
Kapsenberg M L et al., 1999, Clin Exp Allergy, 29:33-36.
Latz E et al., 2004, Nat Immunol., 5:190-198.
Le Gall F et al., 2004, J Immunol Methods, 285:111-127.
Leifer C A et al., 2004, J Immunol, 173:1179-1183.
Leroy B P et al., 1992, Dermatology, 184:271-274.
Mudde G C et al., Immunol Cell Biol, 1996, 74:167-173.
Orlandi R et al., 1989, Proc Natl Acad Sci, 86:3833-3837.
Péne 1988, J, Proc Natl Acad Sci, 85:6880-6884.
Rissoan M C, et al., 1999, Science, 283:1183-1186.
Rothenfusser S et al., 2002, Hum Immunol., 63:1111-1119.
Schuster M P Umana, et al., 2005, Cancer Res, 65:7934-7941.
Sturniolo T et al., 2003, Nat Biotechnol, 17:555-561.

(Continued)

*Primary Examiner* — Nora Rooney
(74) *Attorney, Agent, or Firm* — Loza & Loza, LLP; Michael F. Fedrick

(57) ABSTRACT

A molecule or molecule complex capable of binding to TLR9 and to CD32 comprising at least one epitope of at least one antigen, and its use a medicament for the treatment of allergies.

15 Claims, 7 Drawing Sheets

(56) References Cited

OTHER PUBLICATIONS van Schaijk F G et al., 2005, Clin Cancer Res, 11:7130s-7136s.
Wang W W et al., 2005, J Immunol Methods Antigen targeting to dendritic cells with bispecific antibodies, Journal of Immunological Methods, Elsevier Science Publishers B.V.,Amsterdam, NL, vol. 306, No. 1-2, Nov. 30, 2005 (Nov. 30, 2005), pp. 80-92.
Office Action, European Patent Application No. 07722975.5, Sep. 9, 2010.
Extended European Search Report, European Patent Publication No. 06110672.0, Sep. 15, 2006.
International Search Report, International Patent Application No. PCT/EP2007/001722, Jun. 26, 2007.
Written Opinion, International Patent Application No. PCT/EP2007/001722, Jun. 26, 2007.
International Preliminary Examination Report, International Patent Application No. PCT/EP2007/001722, Sep. 9, 2008.
Shirota, H. et al., J Immunol, 164(11):5575-5582 (2000).
Allergy and Immunity, 10(3):56-66 (2003).
Official Action, Japanese Patent Application No. 2013-155366, Jun. 30, 2015 (constituting the Applicant's understanding of item 2, which is in Japanese).

* cited by examiner

BISPECIFIC MOLECULE BINDING TLR9 AND CD32 AND COMPRISING A T CELL EPITOPE FOR TREATMENT OF ALLERGIES

CROSS-REFERENCE TO RELATED APPLICATIONS

This application claims the benefit of priority under 35 U.S.C. §120 and is a continuation in part of U.S. patent application Ser. No. 12/281,504, filed on Sep. 3, 2008 and entitled BISPECIFIC MOLECULE BINDING TLR9 AND CD32 AND COMPRISING A T CELL EPITOPE FOR TREATMENT OF ALLERGIES, which is the U.S. national stage of International Application No. PCT/EP2007/001722, filed Feb. 28, 2007, which claims the benefit of priority under 35 U.S.C. §119 from European Patent Application No. 06110672.0, filed Mar. 3, 2006 and entitled NOVEL MOLECULES. The contents of the foregoing patent applications are hereby incorporated by reference in their entirety.

SEQUENCE LISTING

The entire content of a Sequence Listing titled "Sequence_ Listing.txt," created on May 28, 2013 and having a size of 69 kilobytes, which has been submitted in electronic form in connection with the present application, is hereby incorporated by reference herein in its entirety.

FIELD OF THE INVENTION

The present invention relates to molecules with binding specificity to both, Toll-like Receptor 9 (TLR9) and CD32 containing one or more T cell antigen epitopes. The invention further relates to the production of these molecules and their use for the preparation of medicaments for the treatment of allergies.

BACKGROUND

Allergy is considered to be a hypersensitive reaction to proteins in the environment (air/water/food). Allergens are antigens to which atopic patients respond with IgE antibody responses subsequently leading to allergic reactions. Antigens in the complexes or fusion proteins can be environmental allergens (e.g. house dust mite, birch pollen, grass pollen, cat antigens, cockroach antigens), or food allergens (e.g. cow milk, peanut, shrimp, soya), or a combination of both. IgE molecules are important because of their role in effector cell (mast cell, basophiles and eosinophils) activation. More recently, it has been accepted that IgE also plays an important role in the induction phase of allergic diseases, by up-regulating the antigen capture potential of B cells and dendritic cells (DC), both through low affinity (CD23) and high affinity receptors (FcεRI) [1]. The negative functions of IgE antibodies can be counteracted by allergen specific IgG antibodies. e.g. because they direct the immune response away from B cells to monocytes and DC [2]. In addition, they compete with IgE molecules for allergen binding sites. Allergies therefore can be treated, cured and prevented by the induction of allergen specific IgG molecules.

IgG molecules have a serum half-life of approximately 3 weeks as compared to roughly 3 days for IgE molecules. IgE molecules are induced by the interaction between (naive) B cells and Th2 cells which provide the IL-4 and IL-13 together with CD40L expression necessary to induce a class switch to IgE in memory B cells and plasma cells [3]. In contrast, TM cells, which produce IFN-γ and IL-2, induce a class switch to IgG. Therefore, induction of Th1, rather than Th2 helper T cell responses against allergens, is beneficial for the prevention, treatment and cure of allergic diseases.

To date several forms of active vaccination using allergens are used. The most common is the so called "Immunotherapy", which depends on frequent immunizations with relatively high concentrations of allergens. This technique is only moderately effective in a minority of allergic diseases such as Bee venom allergy and in some cases of Rhinitis and Conjunctivitis, and recently some reports have shown effectiveness in asthma and atopic dermatitis. More recently rush immunotherapy, where increasing amounts of allergen are injected in a rather short time frame, has been proposed with slightly better results [4; 5]. Usually the subcutaneous route is used for administration of the allergens, but recently this route has been compared to oral application or even local application, the results are generally positive but not always consistent. A different technique for immunotherapy is the one described by Saint-Remy (EP 0 178 085 and 0 287 361), which makes use of autologous IgG antibodies which are in vitro complexed to the relevant allergens. This technique allows far smaller amounts of allergen to be applied with fewer side effects.

The mechanism behind these therapies is unclear. In the classical therapy there seems to be a beneficial effect if the therapy induces an increase in specific IgG antibodies, although not every significant increase of specific IgG is correlated with successful immunotherapy. A possible argument why this is the case is the relatively low affinity of IgG antibodies for CD32 on B cells, monocytes and mast cells. The Saint-Remy approach selects the specific IgG antibodies from the patient, which are subsequently mixed with relevant allergens in vitro. This way they assure that the allergen cannot react freely with cells or other antibody isotypes on cells such as IgE on mast cells. In addition they claim that anti-idiotypic antibodies are raised against the specific IgG molecules, which in the future will prevent allergy.

In WO 97/07218 Allergen-anti-CD32 Fusion Proteins are described. In this publication the problems with isolating specific IgG molecules and the low affinity of these IgG antibodies for CD32 are circumvented and the risk factors of classical immunotherapy, which uses complete "IgE binding" allergens, are reduced. However, the claimed induction of Th1 memory responses due to solely directing the anti-CD32 containing vaccine to dendritic cells cannot be substantiated.

Even in view of the intensive research for therapeutic approaches to treat allergic diseases, there is still a great demand for providing medicaments for successful treatment of allergies.

The object of the invention is therefore to provide novel molecules with improved properties for the treatment of allergic diseases.

According to the invention this object is achieved by the subject matter of the claims.

BRIEF SUMMARY OF THE INVENTION

CD32 is strongly expressed on monocytes/dendritic cells and B cells and thus the molecule of the present invention is designed to direct the immune response to these important immunological cells, with the intention to prevent allergen presentation by the B cells, while promoting allergen presentation by especially dendritic cells (DCs), the latter leads to induction of Th1 responses against the allergens in the molecule or molecule complex that can be formulated as vaccine. More recent knowledge shows that two types of dendritic cells (DC) exist: myeloid (mDC) and plasmacytoid dendritic cells (pDC) [6], which has led to the new concept of DC1 and DC2 cells [7]. In this concept DC1 cells promote the induction of Th1 cell development after antigen specific stimulation and DC2 cells support the development of Th2 cells. Monocyte derived DC (or mDC) are generally considered to be of DC1 type, whereas pDC are considered to be DC2 type [6]. Both types of DC express CD32a and will induce an allergen specific T cell response; however it is not guaranteed that the outcome will be of Th1 type. In fact, in allergic donors Th2 responses are more likely [8]. Importantly, the pDC express the TLR9 receptor, which binds CpG-ODNs (oligodeoxynucleotides [ODNs] containing unmethylated CpG motifs). Activation of this receptor in the pDC leads to a very strong production of IFN-α and IL-12 [9], which promotes Th1 induction and thus transforms the potential DC2 into DC1 cells.

Therefore, the molecule of the invention can combine the activation of the TLR9 receptor in pDC with the specific stimulation and induction of allergen specific Th1 cells and comprises therefore a significant improvement of earlier concepts.

The invention comprises a molecule or a molecule complex having binding specificity for toll-like receptor 9 and CD32, wherein the molecule or molecule complex includes at least one epitope, preferably at least one T cell epitope, of at least one antigen. The molecule or molecule complex of the invention will also bypass the effector function of mast cells, which carry IgE, for the native allergen of which T cell epitopes have been selected to be part of the fusion protein.

Preferably the molecule or molecule complex according to the invention can have one or more of the following unique characteristics:

- Activation and induction of allergen specific Th1 cells, without activation of allergen-specific B-cells.
- Activation and induction of allergen specific Th1 cells, without activation of mast cells or any other effector cell, which, by means of allergen specific IgE or IgG, may become activated by the natural allergens of which the selected T cell epitopes are represented in the molecule or molecule complex of the invention.

The CD32-binding part of the molecule or molecule complex of the invention selects the relevant cells, which should internalize the complete molecule or molecule complex.

After internalization of the fusion protein according to the present invention by antigen presenting cells the molecule of the invention is degraded and various peptides, in eluding the incorporated T cell epitope(s) are presented on the MHC class II molecules of the antigen presenting cells, therefore stimulating allergen specific T cells.

The incorporated TLR9-binding structure(s) in the molecule or molecule complex of the invention are necessary for the induction of an allergen specific Th1 memory pool, by binding to the cytoplasmatic [10; 11] TLR9 receptor. Activation of the TLR9 receptor leads to a strong induction of IFN-α and IL12 production [9].

According to the present invention, a molecule is a single entity made up of atoms and/or other molecules by covalent bonds. The molecule can be made up of one single class of substances or a combination thereof. Classes of substances are e.g. polypeptides, carbohydrates, lipids, nucleic acids etc.

A molecule complex is an aggregate of molecules specifically and strongly interacting with each other. A complex of various molecules may be formed by hydrophobic interactions (such as e.g. the binding of antibody variable regions in an Fv) or by strong binding of one molecule to another via ligand/receptor interactions such as antibody-antigen binding or avidin-biotin or by complex formation via chelating chemical groups and the like. The molecule complex is preferably produced through chemical conjugation, recombinant fusion and/or affinity binding.

An antigen can be a structure which can be recognized by an antibody, a B-cell-receptor or a T-cell-receptor when presented by MHC class I or II molecules.

An epitope is the smallest structure to be specifically bound within by an antibody, a B-cell-receptor or a T-cell receptor when presented by MHC class I or II molecules. Specificity is defined as preferred binding to a certain molecular structure (in antibody/antigen interactions also called epitope) within a certain context.

A domain is a discrete region found in a protein or polypeptide. A monomer domain forms a native three-dimensional structure in solution in the absence of flanking native amino acid sequences. Domains of the invention will specifically bind to CD32 and/or TLR9 and/or display or present epitopes. Domains may be used as single domains or monomer domains or combined to form dimers and multimeric domains. For example, a polypeptide that forms a three-dimensional structure that binds to a target molecule is a monomer domain.

According to the present invention the term antibody includes antibodies or antibody derivatives or fragments thereof as well as related molecules of the immunoglobulin superfamily (such as soluble T-cell receptors). Among the antibody fragments are functional equivalents or homologues of antibodies including any polypeptide comprising an immunoglobulin binding domain or a small mutated immunoglobulin domain or peptides mimicking this binding domain together with an Fc region or a region homologous to an Fc region or at least part of it. Chimeric molecules comprising an immunoglobulin binding domain, or equivalents, fused to another polypeptide are included.

Allergens are antigens to which atopic patients respond with allergic reactions.

DETAILED DESCRIPTION OF THE INVENTION

Figure 1:
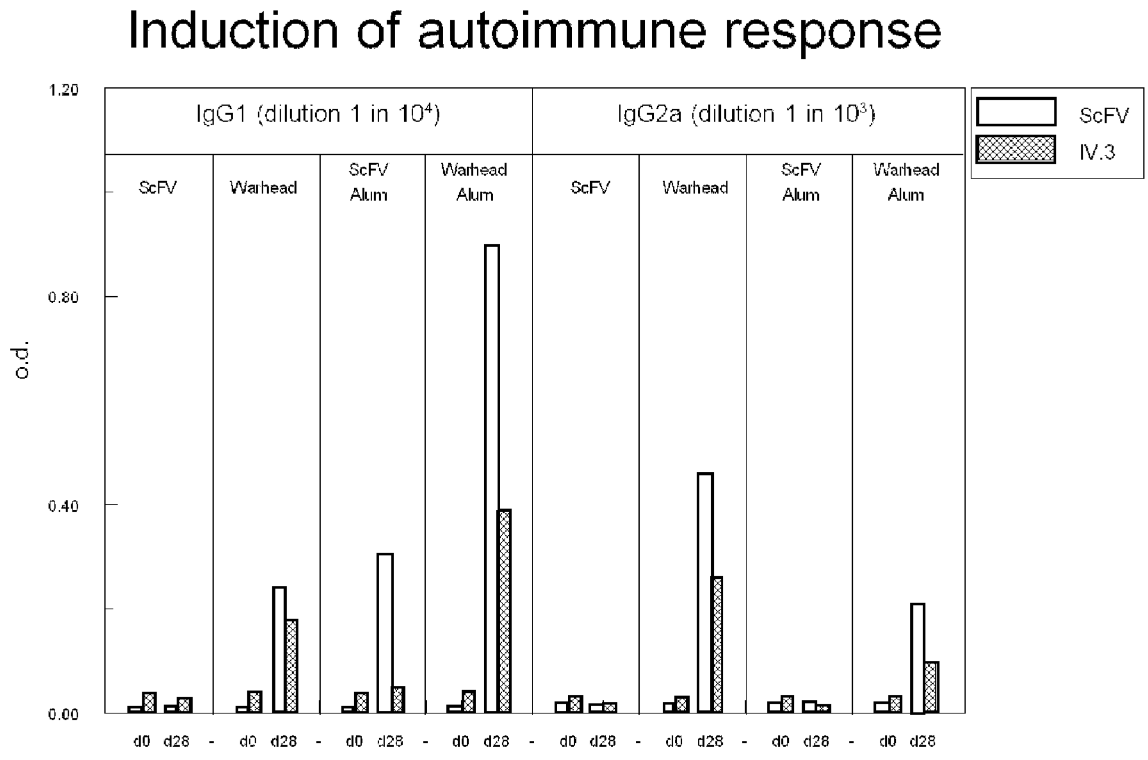
FIG. 1 is a graph showing the results of an experiment in which an autoimmune response was induced in mice using ScFV-1-coil and mAb IV.3.

The invention provides a molecule or a molecule complex being capable of binding to toll-like receptor 9 (TLR9) and Fc gamma receptor RII (CD32) and including at least one epitope of at least one antigen.

In one embodiment of the invention the molecule or molecule complex comprises at least three parts, one part being a structure specifically binding to TLR9 (monovalently, bivalently or multivalently), another part being a structure specifically binding to CD32 (monovalently, bivalently or multivalently) and at least one other part being one or more T cells epitopes of an antigen and/or allergen. The parts may be independent structures which are linked together either by chemical linkages or by genetic fusion or by other (non-covalent) interactions such as ligand-receptor or antibody interactions.

The linkages between the different parts may be different. For example, in one preferred embodiment, the linkage between the parts binding to TLR9 and CD32 is by genetic fusion and the link to at least one of the T cell epitopes is via a receptor/ligand interaction (e.g. biotin-streptavidin). The advantage of such a setup is the flexibility in production. The bispecific (anti-TLR9/anti-CD32), generic part of the molecule complex can be produced in the same way for all patients, selected T cell epitopes are linked to the generic part of the molecule complex according to the need. The selection can be based on disease prevalence or on results of individual specificity tests of patients (specific allergy). The complex formation may be performed centralized or at the bed side or at a physician's office.

Chemical linkage of molecules of the various binding molecules of the same or different chemical class may be achieved by many different techniques yielding either a defined molecular ratio of the various parts of the molecule or molecule complex of the invention. It may also lead to a mixture of molecules with different molecular ratios of the various parts of the molecule or molecule complex of the invention.

The ratio of the various parts of the invention may be an equimolar or non-equimolar. The molecule may be monovalent for binding to TLR9 and/or CD32 and/or T cell epitope(s). It may also be bi-, tri- and multivalent for at least one of the parts of the molecule or the molecule complex. If the binding to TLR9 and/or CD32 is bivalent or of higher valency, the binding specificity may be for one or for more epitopes on CD32 and/or TLR9 respectively.

In another embodiment of the invention the binding specificities of the molecule are overlapping so that one part of the molecule or the molecule complex of the invention is binding to both, TLR9 and CD32. Such a part could be selected for by simultaneous screening of molecules for binding to both CD32 and TLR9 or by engineering of a molecule to bind both, CD32 and TLR9. For example, a protein scaffold can be used for displaying loops to bind CD32 and other loops that bind to TLR9.

In a further embodiment of the invention, a protein scaffold can be used to display structures that bind CD32, structures that bind TLR9 and to display T-cell epitopes.

The specific binding molecules can be natural ligands for CD32 and TLR9 and derivatives thereof. For example, the Fc-part of immunoglobulin is binding to CD32. CpG is a naturally occurring ligand for TLR9.

The specific binding molecules can be peptides. CD32- and TLR9-specific peptides according to the invention can be selected by various methods such as phage display technology or by screening of combinatorial peptide libraries or peptide arrays. The peptides can be selected and used in various formats such as linear, constrained or cyclic peptides, the peptides can be chemically modified for stability and/or specificity.

A specifically binding peptide may also be derived from analysis of interaction of a naturally occurring proteinaceous ligand to TLR9 and CD32 by isolation of the minimal binding site of the ligand.

The specific binding peptides can be used as such in the molecule or the molecule complex of the invention or used to be incorporated into other structures such as by grafting into protein scaffolds, antibodies and protein domains or chemically coupled to carrier molecules which might be part of the molecule or molecule complex of the invention.

The binding part of the molecules or molecule complex of the invention can be comprised of proteins such as antibodies or antibody fragments (such as Fab, Fv, scFv, dAb, $F(ab)_2$, minibody, small mutated immunoglobulin domains, soluble T-cell receptor, etc.). Antibodies and antibody fragments and derivatives may be generated and selected for binding to TLR9 and/or CD32 according to known methods such as hybridoma technology, B-cell cloning, phage display, ribosome display or cell surface display of antibody libraries, array screening of variant antibodies.

The binding parts of the molecules or molecule complexes of the invention can be protein domains which occur naturally or domains which are artificially modified. Protein domains or domain derivatives, e.g. domains with mutations such as amino acid substitutions, deletions or insertions or chemically modified domains may be selected for binding to TLR9 and/or CD32 according to known methods (e.g. phage and cell surface display of libraries of domains or domain variants and screening, arrays of variant molecules and screening). The domains include but are not limited to molecules from the following classes:

EGF-like domain, a Kringle-domain, a fibronectin type I domain, a fibronectin type II domain, a fibronectin type III domain, a PAN domain, a GIa domain, a SRCR domain, a Kunitz/Bovine pancreatic trypsin Inhibitor domain, a Kazal-type serine protease inhibitor domain, a Trefoil (P-type) domain, a von Willebrand factor type C domain, an Anaphylatoxin-like domain, a CUB domain, a thyroglobulin type I repeat, a LDL-receptor class A domain, a Sushi domain, a Link domain, a Thrombospondin type I domain, an immunoglobulin domain, an Immunoglobulin-like domain, a C-type lectin domain, a MAM domain, a von Willebrand factor type A domain, an A-domain, a Somatomedin B domain, a WAP-type four disulfide core domain, an F5/8 type C domain, a Hemopexin domain, an SH2 domain, an SH3 domain, a Laminin-type EGF-like domain, a CTLA-4 domain, a C2 domain.

In a preferred embodiment, the binding part of a molecule or molecule complex of the invention comprises a small mutated immunoglobulin domain (SMID) as described in PCT/EP2006/050059.

The binding part of the molecule or molecule complex of the invention can be nucleic acids such as RNAs or DNAs which can be selected for specific binding to TLR9 and/or CD32 according to known methods such as aptamer screening and in vitro evolution techniques.

It is contemplated that also other molecule classes will be able to show specific binding to TLR9 and or CD32. Libraries of other chemical entities than the ones mentioned above, including carbohydrates, lipids, and small organic molecules, may be screened for specific binding to TLR9 and/or CD32 and may be incorporated into the molecule or molecule complex of the invention.

A preferred embodiment of the invention is a recombinant fusion protein consisting of at least one epitope of at least one antigen, at least one binding site interacting with TLR9 and at least one binding site interacting with CD32. The antigen can be as small as one T cell epitope from one antigen or can be a cocktail or mixture of one or more T cell epitopes from one or more different antigens fused or linked together in a way that allows proper processing and presentation by MHC molecules. The order of the epitopes can be selected according to different criteria such as product stability effective processing, (non-)recognition by preformed antibodies in the treated persons. Generally one will select for a stable molecule which can be efficiently presented by MHC and which will lead to minimal recognition by preformed antibodies.

The invention further comprises the physical coupling of at least one molecule interacting with TLR9, at least one molecule interacting with CD32 and one or more T cell epitopes from one or more antigens linked together in a random form.

Additionally, the invention provides the preparation of a medicament containing the fusion protein according to the invention and its use for treatment of allergies. The medicament can be a vaccine formulation containing the molecule or molecule complex according to the invention, useful esp. for active immunotherapy.

The recombinant production of bispecific binding structures of the molecule or the molecule complex of the invention (i.e. binding to CD32 and to TLR9) can be accomplished in different ways, e.g. by:

- Quadroma technology (fused hybridomas) [12; 13];
- bispecific scFvs, either as “diabodies” or simply by genetic fusion of different scFvs [14];
- single-domain antibodies in which VH recognizes one antigen and VL another one;
- chi-bAbs (as described in EP0640130);
- small mutated immunoglobulin domains, by including engineered immunoglobulin domains, specifically binding to CD32 and/or to TLR9 in constructs coding either for complete antibodies or for antibody fragments such as Fab (according to PCT/EP2006/050059);
- in the context of this invention, binding to CD32 can also be accomplished by monomeric or multimeric immunoglobulin Fc region(s) or a parts thereof especially when the affinity for CD32 of the Fc parts is enhanced, while TLR9 binding is achieved through the normal binding site (VH/VL) of the antibody;
- Fc-region(s) of an immunoglobulin or parts thereof, binding to CD32, fused to any other TLR9 specific binding motif;
- the Fc part of the above mentioned antibody may be “glyco-engineered” to increase the affinity for human FcγR’s [15] engineered scaffolds, specifically binding to TLR9 and/or CD32 of any kind can be used and linked together as needed. These binding scaffolds can be protein domains, fibronectin III, lipocalins, Protein A or α-amylase inhibitor, Ankyrin Repeat Proteins, a C2 domain, an A-domain, an EGFR like domain, a dab, a chi-bAb, CTLA-4, gamma crystalline or any other protein, protein domain or part thereof.

The molecule or molecule complex of the invention consist of one or more epitopes and one or more binding structures, which interact with TLR9, preferably human TLR9 and one or more binding structures, which interact with CD32, preferably human CD32. For easy in vivo testing of the inventive protein the binding structures that recognize human TLR9 and human CD32 may cross react with monkey or mouse TLR9 and monkey or mouse CD32. The selected antigens/allergens may be complete natural/native proteins or parts of these, as long as epitopes which can be presented on MHC class II molecules and which can be recognized by T cells are present on the sequences present in the molecule or molecule complex. The part(s) of the molecule or molecule complex, which interact with TLR9 and CD32 may be complete or incomplete (modified) antibodies or fragments or derivatives thereof, as long as binding to TLR9 and CD32 is retained.

Alternatively, anti-TLR9 and anti-CD32 antibodies or derivatives or fragments thereof, which still specifically recognize and bind to human TLR9 and CD32 such as expressed by B cells, and dendritic cells can be used.

Alternatively, the antibodies interacting with TLR9 or CD32 are improved antibodies with higher affinity than the original antibodies.

Exemplary antibody molecules are intact immunoglobulin molecules and those portions of an immunoglobulin molecule that contains the paratope, including those portions known as Fab, Fab', $F(ab')_2$, Fc and F(v), dAb.

The antibodies can be IgG, IgM, IgE, IgA or IgD. The molecules interacting with TLR9 or CD32 can be of any origin, preferably of mammalian origin, preferably of human, mouse, camel, dog or cat origin or humanized. Preferably the molecules are antibodies, preferably human or humanized antibodies.

As used herein, if the molecule or molecule complex of the invention is a fusion protein, it can be expressed in host cells which cover any kind of cellular system which can be modified to express the fusion protein. Within the scope of the invention, the term “cells” means individual cells, tissues, organs, insect cells, avian cells, mammalian cells, hybridoma cells, primary cells, continuous cell lines, stem cells and/or genetically engineered cells, such as recombinant cells expressing an antibody according to the invention.

Cells can be bacterial cells, fungal cells yeast cells, insect cells, fish cells and plant cells. Preferably the cells are animal cells, more preferably mammalian cells. These can be for example BSC-1 cells, LLC-MK cells, CV-1 cells, CHO cells, COS cells, PerC6 cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0, NSO cells or derivatives thereof.

Preferably the binding structures of the molecule or the molecule complex of the invention recognizing TLR9 and CD32 are small mutated immunoglobulin domains, being for example an Fab fragment in which one binding site (either specific for CD32 or for TLR9) is formed by VH/VL, and is combined with a second binding site (either specific for TLR9 or for CD32 respectively) which can be an engineered CL or an engineered CH1, CH2, CH3, CH4, VL or VH domain according to PCT/EP/2006/050059; or a complete antibody in which one binding site is formed by VH/VL, and is combined with a second binding site which can be an engineered CL, CH1, CH2, CH3, CH4, VL or VH domain according to PCT/EP/2006/050059.

According to the invention, the molecule or molecule complex contains at least one structure that specifically binds to CD32.

An anti-CD32 antibody can be derived by known methods (such as hybridoma technology, B-cell cloning and antibody library screening). For selection, cells displaying CD32 in a natural format can be used or a recombinant extracellular part of CD32 can be used or synthetic peptides selected from the CD32 amino acid sequence can be used. Selection criteria are that the binding structure recognizes CD32a. In case also CD32b is recognized it is preferred that the affinity for CD32a≥CD32b.

As an example, the Fab fragment from the anti-CD32 IV.3 antibody derived from the cell line HB-217 can be used. Using the method e.g. described by Orlandi et al 16, the Fab fragment is cloned from the cell line HB-217. Alternatively, other formats such as scFv can be constructed of the known V-gene sequences. However, for optimal combination with an anti-TLR9 antibody or Fab fragment or Fv fragment it is preferred to select specific binders using one or more of the small mutated immunoglobulin domain libraries from CH1, CH2 CH3, CH4, CL, VL or VH.

Selected CH1, CH2, CH3, CH4, CL1 VL or VH domains can then be cloned into the existing sequence of an anti-TLR9 antibody or a Fab or an Fv fragment thereof thus generating a bi-specific antibody or Fab fragment.

The selected CD32 binding entities should preferably have the following characteristics:

1. Interaction with CD32a leads to internalization of the receptor-binding-structure complex, activation of the antigen presenting cell through the ITAM motif in the cytoplasmic tail of the receptor and antigen presentation of the linked/fused T cell epitopes;

2. Interaction with CD32b leads to negative signaling of the receptor through the ITIM motif;

3. Interaction should show cross reactivity between human and monkey CD32 (for testing of efficacy in a relevant in vivo model);

4. Interaction should show cross reactivity with mouse CD32 (for testing in an established in vivo model for allergy);

For obtaining a binding structure that specifically binds to TLR9, several procedures can be used (such as hybridoma technology, B-cell cloning and antibody library screening). For selection, cells expressing TLR9 in a natural format can be used to isolate natural TLR9 or a recombinant TLR9 can be used or synthetic peptides selected from the TLR9 amino acid sequence can be used. Alternatively, purified TLR9 or TLR9 expressed by cell lines can be used. Antibody genes coding for VL and VH respectively can be extracted after selection for binding to TLR9 and be used to design a recombinant antibody or Fab fragment specific for human TLR9. Alternatively, a single-chain Fv can also be made and fused with the anti-CD32 scFv mentioned above. However, for optimal combination with the anti-CD32 antibody or scFv or Fab fragment it is preferred to select specific binders using one or more of the small mutated immunoglobulin domain libraries from CH1, CH2 CH3, CH4, CL, VH or VL. Selected CH1, CH2, CH3, CH4, CL, VL or VH domains can then be cloned into the existing antibody or Fab fragment or scFv of anti-CD32 antibody thus generating a bi-specific Fab fragment. The selected TLR9 binding entities should preferably have the following characteristics:

1. Interaction with TLR9 leads to signal transduction and cytokine production;

2. Interaction may show cross reactivity between human and monkey TLR9 (for testing of efficacy in a relevant in vivo model);

3. Interaction may show cross reactivity with mouse TLR9 (for testing in an established in vivo model for allergy) and CD32.

Of course the fusion protein can similarly be made using the Fab part of an existing aTRL9 monoclonal antibody. Using the method e.g. described by Orlandi et a116, the Fab fragment is cloned from e.g. clone 26C593 available from Imgenex Corp., as described above for the fab fragment of the aCD32 Ab IV.3. Again for optimal combination with the anti-TLR9Fab fragment it is best to select specific binders for CD32 using one or more of the small mutated immunoglobulin domain libraries from CH1, CH2, CH3, CH4, CL, VL or VH. Selected CH1, CH2, CH3, CH4, CL, VL or VH domains can then be cloned into the existing Fab fragment of anti-TLR9 antibody thus generating a bi-specific molecule.

Finally, e.g. in the absence of available suitable existing Ab's for both CD32 and TLR9, it is also possible to construct a bi-specific molecule using the small mutated immunoglobulin domain libraries from CH1, CH2 CH3 or CL to select specific binders for both CD32 and TLR9 which are subsequently combined to form new structures existing of at least 1 binding structure specific for CD32 and 1 binding structure specific for TLR9 derived from any of the possible libraries in any of the possible combinations (CH1-CH1 or CH1-CH2 or CH1 CH3 or CH2-CH4, or CH3-CH4, or CH1-CH4 or CH2-CH3 etc.).

Alternatively, a single variable domain of the immunoglobulin superfamily may be selected for binding to TLR9 or CD32 with CDR-loops. The selected binder is then randomized at non-structural loop positions to generate a library of variable domains which is selected for the respective other antigen, i.e. in case of a variable domain binding with CDR loops to TLR9 the selection is for binding to CD32 and vice versa. It is also possible to select a library of a V-domain which contains variations in the CDR loops at the same time as variations in the non-CDR-loops for binding to TLR9 and CD32 sequentially or simultaneously.

Such bispecific V-domains may also be part of antibodies or antibody fragments such as single-chain-Fvs, Fabs or complete antibodies.

Selection of a suitable TLR9 epitope, i.e. sequence 244-256 (SEQ ID No 1) of the mature TLR9 protein in amino acid 1 letter code:

```
CPRHFP QLHPDTFS
214    250    257
```

will fulfill criterion 1 and 2 but not 3, whereas sequence 176-191 (SEQ ID No 2) of the mature protein TLR9 in amino acid 1 letter code:

```
LTHL SLKYNNLTVV PR
176  180        191
```

and

Sequence 216-240 of the mature protein TLR9 (SEQ ID No 3) in amino acid 1 letter code:

```
ANLT ALRVLDVGGN CRRCDHAPNP C
216  220        230        240
```

will fulfill all three criteria and are thus preferred for use in this invention.

The process for producing the molecule or molecule complex is carried out according to known methods, e.g. by using recombinant cloning techniques or by chemical cross linking.

A product as described in this invention can be produced in the following way:

The obtained VH and VL of the anti-CD32 antibody are fused to CH 1 and CL respectively. The CL has previously been engineered using SMID technology (PCT/EP2006/050059) and selected using phage display to bind to TLR9 as described below. CH1 is fused at its C-terminus to a sequence encoding the selected T cell epitopes. These two fusion-protein encoding genes are cloned into an expression vector allowing the expression of two independent genes (or into two independent expression vectors) and are co-expressed in bacteria, yeast or animal cells or any other suitable expression system. Thus, an Fab with the desired characteristics, i.e. binding to CD32, binding to TLR9 and carrying the relevant T-cell epitopes is produced.

Alternative examples applying SMID technology include:

- An scFv against TLR9 is derived from a phage display library or from an existing hybridoma, and a CD32 binding molecule is derived from a CH2-CH4, or CH3-CH4, or CH1-CH4 or small mutated immunoglobulin domain library. These two coding sequences are ligated together and a sequence coding for T cell epitopes is attached. The fusion protein is then expressed in bacteria, yeast or animal cells or any other suitable expression system;
- Alternatively, TLR9-specificity and CD32-specificity are swapped: An scFv against CD32 is derived e.g. from a phage display library or from an existing hybridoma, and a TLR9-binding molecule is derived from a CH2-CH4, or CH3-CH4, or CH1-CH4 or small mutated immunoglobulin domain library. These two coding sequences are ligated together and a sequence coding for T cell epitopes is attached. The fusion protein is then expressed in bacteria, yeast or animal cells or any other suitable expression system;
- VH and VL of an anti-TLR9 antibody are fused to CH 1 and CL respectively. CL has previously been engineered and selected using phage display to bind to CD32 (SMID). CH1 is fused at its C-terminus to a sequence encoding the T cell epitopes. These two fusion-protein encoding genes are cloned into an expression vector allowing the expression of two independent genes (or into two independent expression vectors) and are coexpressed in bacteria, yeast or animal cells or any other suitable expression system, (again, anti-TLR9 and anti-CD32 can be swapped. CH1 and CL can also be swapped);
- Heavy and light chain genes of an anti-TLR9 antibody are taken as a whole. In the heavy chain gene, the CH2 (or CH1 or CH3 or CH4) region is replaced by a CH2 (or CH1 or CH3 or CH4 or CL or VH or VL) region which has previously been engineered and selected using phage display to bind to CD32 (small mutated immunoglobulin domain). CH1, CH2, CH3 or CH4 is fused at its C-terminus to a sequence encoding the T cell epitopes. These two genes are again cloned in expression vectors and expressed in animal cells;
- 2 small mutated immunoglobulin domains, one specific for TLR9, the other specific for CD32 are fused and combined with T-cell epitopes;
- 1 small mutated immunoglobulin domain with 2 different specificities (TLR9 and CD32) is combined with T-cell epitopes.

Antigens and Epitopes:

The antigens that are part of the molecule or molecule complex according to the invention can be complete allergens, denatured allergens or any antigens that are treated in any possible way to prevent binding to IgE. Such treatment may consist of epitope shielding of the antigenic protein using high affinity IgM, IgD, IgA or IgG antibodies directed to the same epitopes as the patient's IgE antibodies as described by Leroy et al [20]. Such antibodies may also bind close to the IgE specific epitopes thus preventing binding of the IgE antibodies by sterical hindrance.

Allergens are generally defined as antigens to which atopic patients respond with IgE antibody responses subsequently leading to allergic reactions. Antigens used in the molecule or the molecule complex of the invention can be environmental allergens (e.g. house dust mite, birch pollen, grass pollen, cat antigens, cockroach antigens), or food allergens (e.g. cow milk, peanut, shrimp, soya), or a combination of both. Also non relevant antigens such as HSA can be part of the molecule or molecule complex according to the invention. The antigen can be a complete allergen, exemplary an allergen for which patients with atopic dermatitis, allergic asthma, allergic rhinitis or allergic conjunctivitis are allergic. Preferably the allergen use in the molecule or molecule complex according to the invention does not bind to IgE from the patient in need of treatment.

The antigens and/or epitopes used in the invention can be from natural sources or be produced by recombinant technology or be produced synthetically. Antigens and/or epitopes of the invention may contain ligand structures which facilitate incorporation of antigens and/or epitopes into molecule complexes of the invention via ligand/receptor interactions or antibody binding. Antigens and/or epitopes of the invention may contain chemical groups which facilitate covalent linkage of the antigens and/or epitopes to the CD32- and/or TLR9-binding structures of the molecule of the invention.

In one embodiment of the invention the antigens and epitopes of the molecule or molecule complex of the invention may be covalently linked to the CD32 binding structure and/or to the TLR9 binding structure.

In one embodiment antigens and/or epitopes may also be linked by a ligand/receptor interaction such as biotin and avidin to the molecule or molecule complex of the invention. For example, the antigens or epitopes to be used in the molecule of the invention may be produced with biotin or a biotin mimetic attached to it. The CD32 binding structure and/or the TLR9 binding structure may be produced with avidin or another biotin-specific ligand attached to it. After mixing of these molecules with the different attachments, a stable molecule complex is formed according to the invention. Alternatively, an antibody/antigen binding can be used to form a molecule complex of the invention. High affinity interactions are preferred for these embodiments (e.g. high affinity anti-digoxigenin antibody and digoxigenin labeled antigens and/or epitopes).

In one embodiment of the invention the antigens and/or epitopes are genetically fused to the CD32-binding structure and/or to the TLR9-binding structure.

If the molecule of the invention is a fusion protein, the antigen is preferably produced from at least one T-cell epitope-containing DNA-subsequence of an allergen. The T cell epitopes can alternatively be from one or more related and/or unrelated allergens.

Preferably, the T cell epitopes comprise a new protein, which is not as such a naturally existing protein and therefore is not recognized by existing IgE or IgG antibodies in the patient. Therefore, instead of selecting short T cell epitopes which are cut apart and fused together again in a different order, one could also select a larger stretch of T cell epitopes (>28 AA) which are still in their natural order but which have been previously selected not to bind to allergen specific IgE [21].

In principle all known antigens can be used for incorporation into the molecule or molecule complex of the invention to which allergic patients respond with IgE mediated hypersensitivity reactions. The most common environmental allergens in the developed countries are: house dust mite, birch pollen, grass pollen, cat, and cockroach. Each of these allergens has one or more "major allergens" (e.g. house dust mite: major allergen=Der P1; Der F1, birch pollen: major allergen=Bet V1). However, complete antigens, though possible, are not necessary, because the molecule or molecule complex should only induce T cell responses, and T cells respond to small (ca. 12-28 amino acid long) peptides presented in MHC Class II molecules. The selection of T cell epitopes should be designed in such a way that expression on HLA class II molecules of possibly all patients is guaranteed. Some HLA class II molecules are more frequently expressed than others. A good example for such a HLA class II molecule with wide expression is HLA DPw4, which is expressed on approximately 78% of the Caucasian population [22]. Therefore a selection of T cell epitopes could be included in the molecule or molecule complex for each allergen, thus reducing the size and molecular weight of the complex. If overlapping cross-reactive epitopes between allergens from different genetically related organisms, such as *Dermatophagoides pteronyssinus* (Der P1) and *Dermatophagoides farinae*, (Der F1), are present, they are preferred.

To allow for correct antigen processing, DNA coding for stretches slightly longer than the actual T cell epitope should be included in the molecule or molecule complex and/or the epitopes can be separated from each other by introducing stretches of spacer DNA preferably containing (hydrophobic) epitopes recognized by major protein processing enzymes in antigen presenting cells such the asparagine-specific endopeptidase (AEP) or cathepsin S, cathepsin D or cathepsin L [23].

For fusion to the genes coding for the binding structures specific for TLR9 and CD32, preferably short DNA sequences of major allergens are used such as house dust mite major allergen I (Der P1, Der F1), house dust mite major allergen II (Der P2, Der F2), or birch pollen allergen (Bet V1). These short DNA sequences contain the genetic code for one or more T cell epitopes, which after processing, appear on the surface of antigen presenting cells and therefore induce an immune response in the responding allergen specific T cells. Not only T cell epitopes from Der P1 and Der P2 but also Der P3, Der P4, Der P5, Der P6, Der P7 etc. and Der F3, Der F4, Der F5, Der F6, Der F7 etc. can be used in a molecule or molecule complex of the invention. T cell epitopes from these allergens may be selected by classical epitope mapping using T cell clones [24] or by using modern HLA Class II predicting software such as the Tepitope program [25; 26]. For the molecule or molecule complexes, which can be formulated as vaccine, it is not necessary to combine T cell epitopes from a single allergen source only; to the contrary it is preferred to include as many T cell epitopes derived from different allergen sources produced by one or many different species, e.g. a combination of allergens from house dust mites and of allergens from grass pollen, cats and/or birch pollen.

As an example for Der P1 the majority of the T cell epitopes can be found in the following sequences 101-143 of the mature protein in amino acid 1 letter code (SEQ ID No 4):

```
QSCRRPNAQ RFGISNYCQI YPPNANKIRE ALAQPQRYCR HYWT
101       110        120        131       140 143
```

Especially the amino acid sequence 101-131 contains at least 3 T cell epitopes24, which bind to a number of HLA class II molecules in amino acid 1 letter code (SEQ ID No 5):

```
QSCRRPNAQ RFGISNYCQI YPPNANKIRE AL
101       110        120         131
```

The sequence 107-119 contains an important T cell epitope that binds to HLA DPw4 as well as HLA DPw5 24. These HLA Class II molecules are expressed by the majority of the population. The epitope in amino acid 1 letter code (SEQ ID No 6):

```
NAQ RFGISNYCQI
107 110      119
```

Other important T cell epitopes which in addition are shared between Der P1 and Der F1 are found in the sequences 20-44 and 203-226 of the mature protein in amino acid 1 letter code:

```
                                      (SEQ ID No 7)
RTVTPIRMQG GCGSCWAFSG VAATE
20         30         40  44
and

                                      (SEQ ID No 8)
YDGRTII QRDNGYQPNY HAVNIVGY
203     210        220     227
```

Examples of T cells epitopes shared between Der P2 and Der F2 are found in the sequence 26-44, 89-107 and 102-123

```
                                   (SEQ ID No 9)
PCII HRGKPFQLEA VFEAN
26   30         40  44

                                   (SEQ ID No 10)
K YTWNVPKIAP KSENVVVT
89           100    107

                                   (SEQ ID No 11)
ENVVVTVK VMGDDGVLAC AIAT
102      110        123 127
```

From the above mentioned T cell epitopes of Der P1/F1 and Der P2/F2 one can design several functional molecule or molecule complexes, e.g.: By taking from Der P1 the following sequences:

```
                    (Sequence A, SEQ ID No 12)
QSCRRPNAQ RFGISNYCQI YPP
101       110        120

                    (Sequence B, SEQ ID No 13)
CQI YPPNANKIRE AL
117 120        130

                    (Sequence C, SEQ ID No 14)
IRE ALAQPRYCR HYWT
127 130       140 143

                     (Sequence D, SEQ ID No 7)
RTVTPIRMQG GCGSCWAFSG VAATE
20         30         40  44

                     (Sequence 3, SEQ ID No 8)
YDGRTII QRDNGYQPNY HAVNIVGY
203     210        220     227
```

-continued

And from Der P 2

(Sequence F, SEQ ID No 9)

```
PCII HRGKPFQLEA VFEAN
26   30         40   44
```

(Sequence G, SEQ ID No 10)

```
K YTWNVPKIAP KSENVVVT
89           100    107
```

(Sequence H, SEQ ID No 11)

```
ENVVVTVK VMGDDGVLAC AIAT
102      110        120 123
```

One can design a cDNA with the order B,A,E,H,G,C,F,D or H,A,D,C,F,G,E,B, but any possible combination of the selected sequences will do. The preferred order of the epitopes will largely be determined on the basis of expression efficiency of the complete recombinant molecule. Also duplications of sequences are allowed e.g. B,B,A,E,E,G,C, G,F,A,D etc. The T cell epitope part may of course also contain the genetic codes for shorter peptides or longer peptides for more and for fewer peptides, as long as one or more T cell epitopes from one or more different allergens/antigens are included.

Epitopes from other allergens such as Bet V1, Lol P1, FeL d1 with similar characteristics will be preferred for inclusion in the molecule or molecule complex according to the invention.

The invention also concerns a method of treating diseases, especially allergies, which comprises administering to a subject in need of such treatment a prophylactically or therapeutically effective amount of a molecule or molecule complex according to the invention for use as a pharmaceutical, especially as an agent against allergies.

The molecule or molecule complex may be admixed with conventional pharmaceutically acceptable diluents and carriers and, optionally, other excipients and administered parenterally intravenously or enterally, e.g. intramuscularly and subcutaneously. The concentrations of the molecule or molecule complex will, of course, vary depending, for example, on the compound employed, the treatment desired and the nature of the form.

For different indications the appropriate doses will, of course, vary depending upon, for example, the molecule or molecule complex used, the host, the mode of application and the intended indication. However, in general, satisfactory results are indicated to be obtained with 1 to 4 vaccinations in 1-2 years, but if necessary repeated additional vaccination can be done. It is indicated that for these treatments the molecule or molecule complex of the invention may be administered in 2-4 doses and with an application schedule similar as conventionally employed.

It further concerns a molecule or molecule complex according to the invention for use as a pharmaceutical, particularly for use in the treatment and prophylaxis of allergies.

The pharmaceutical composition prepared according to the present invention for use as vaccine formulation can (but does not have to) contain at least one adjuvant commonly used in the formulation of vaccines apart from the molecule or molecule complex. It is possible to enhance the immune response by such adjuvants. As examples of adjuvants, however not being limited to these, the following can be listed: aluminum hydroxide (Alu gel), QS-21, Enhanzyn, derivatives of lipopolysaccharides, *Bacillus* Calmette Guerin (BCG), liposome preparations, formulations with additional antigens against which the immune system has already produced a strong immune response, such as for example tetanus toxoid, *Pseudomonas* exotoxin, or constituents of influenza viruses, optionally in a liposome preparation, biological adjuvants such as Granulocyte Macrophage Stimulating Factor (GM-CSF), interleukin 2 (IL-2) or gamma interferon (IFNγ). Aluminum hydroxide is the most preferred vaccine adjuvant.

Summary of a Possible Mode of Action of the Fusion Protein According to the Invention:

The fusion protein according to the present invention, can be formulated in any of the available acceptable pharmaceutical formulations, but is preferably formulated as a vaccine. The aCD32 binding portion of the fusion protein according to the invention selects the relevant cells. Triggering of CD32 on these cells will actively induce internalization of the receptor plus the attached fusion protein and by doing so facilitates the interaction of the TLR9 binding portion of the fusion protein with the TLR9, which is expressed within the cytoplasm of the relevant antigen presenting cells [10; 11].

As a consequence of the CD32 mediated internalization, the subsequent processing and presentation of the selected T cell epitopes on MHC Class II molecules, combined with the specific activation of cytoplasmic TRL9 in the antigen presenting cells, allergen specific T cells will be (re-)programmed to become Th1 memory cells. These allergen specific Th1 memory cells at a later time point will induce allergen specific IgG production when encountering the same epitopes derived from the natural allergens presented by naturally exposed allergen specific B cells. These TM cells thus are necessary for rebalancing the immune system from IgE to IgG dominated antibody production.

EXAMPLES

The following examples shall explain the present invention in more detail, without, however, restricting it.

Example 1

Panning of the Human CL-Phage Library on a TLR-9 Peptide e.g. Sequence 216-240 of the Mature Protein TLR9 (SEQ ID No 3) in Amino Acid 1 Letter Code

```
ANLT ALRVLDVGGN CRRCDHAPNP C
216  220        230        240
```

3 panning rounds shall be performed according to standard protocols. Briefly, the following method can be applied. Maxisorp 96-well plates (Nunc) are coated with the (synthetic) peptide representing part of the sequence of the TLR-9. For coating the peptides in the wells, 200 μl of the following solution are added per well: 0.1 M Na-carbonate buffer, pH 9.6, with the following concentrations of dissolved peptide:

1st panning round: 1 mg/ml TLR-9 peptide

2nd panning round: 500 μg/ml TLR-9 peptide

3rd panning round: 100 μg/ml TLR-9 peptide

Incubation is for 1 hour at 37° C., followed by blocking with 2% dry milk (M-PBS) with 200 μl per well for 1 hour at room temperature. The surface display phage library is then allowed to react with the bound peptide by adding 100 μl phage suspension and 100 μl 4% dry milk (M-PBS), followed by incubation for 45 minutes with shaking and for 90 minutes without shaking at room temperature. Unbound phage particles are washed away as follows. After the 1st panning round: 10×300 µl T-PBS, 5×300 µl PBS; after the 2nd panning round: 15×300 µl T-PBS, 10×300 µl PBS; after the 3rd panning round: 20×300 µl T-PBS, 20×300 µl PBS. Elution of bound phage particles is performed by adding 200 µl per well of 0.1 M glycine, pH 2.2, and incubation with shaking for 30 minutes at room temperature. Subsequently, the phage suspension is neutralized by addition of 60 µl 2M Tris-Base, followed by infection into *E. coli* TG1 cells by mixing 10 ml exponentially growing culture with 0.5 ml eluted phage and incubation for 30 minutes at 37° C. Finally, infected bacteria are plated on TYE medium with 1% glucose and 100 µg/ml Ampicillin, and incubated at 30° C. overnight.

Example 2

Cloning of Selected Clones of Human CL Mutants Selected Against TLR-9 for Soluble Expression Phagemid DNA from the phage selected through the 3 panning rounds is isolated with a midi-prep. DNA encoding mutated CL-regions is batch-amplified by PCR and cloned Ncol-Not1 into the vector pNOTBAD/Myc-His, which is the *E. coli* expression vector pBAD/Myc-His (Invitrogen) with an inserted Not1 restriction site to facilitate cloning. Ligated constructs are transformed into *E. coli* LMG194 cells (Invitrogen) with electroporation, and grown at 30° C. on TYE medium with 1% glucose and ampicillin overnight. Selected clones are inoculated into 200 µl 2×YT medium with ampicillin, grown overnight at 30° C., and induced by adding L-arabinose to an end concentration of 0.1%. After expression at 16° C. overnight, the cells are harvested by centrifugation and treated with 100 μl Na-borate buffer, pH 8.0, at 4° C. overnight for preparation of periplasmic extracts. 50 μl of the periplasmic extracts were used in ELISA (see below).

Example 3: ELISA of Human CL Mutants Selected Against TLR-9

Selected clones are assayed for specific binding to the TLR-9 peptide by ELISA.

Coating: Microtiter plate (NUNC, Maxisorp), 100 μl per well, 20 μg TLR-9 peptide/ml 0.1 M Na-carbonate buffer, pH 9.6, 1 h at 37° C.

Wash: 3×200 μl PBS

Blocking: 1% BSA-PBS, 1 h at RT

Wash: 3×200 μl PBS

Periplasmic extract binding: 50 μl periplasmic extract

50 μl 2% BSA-PBS, at room temperature overnight

Wash: 3×200 μl PBS

1st antibody: anti-His4 (Qiagen), 1:1000 in 1% BSA-PBS, 90 min at RT, 100 μl per well Wash: 3×200 μl PBS 2nd antibody: goat anti mouse*HRP (SIGMA), 1:1000 in 1% BSA-PBS, 90 min at RT, 100 μl per well Wash: 3×200 μl PBS Detection: 3 mg/ml OPD in Na-citrate/phosphate buffer, pH 4.5, 0.4 μl 30% H2O2

Stopping: 100 ml 3M H2SO4

Absorbance read: 492/620 nm

Clones that give a high signal in this first, preliminary ELISA are cultured in a 20-ml volume at the same conditions as described above. Their periplasmic extracts are isolated in 1/20 of the culture volume as described above and tested with ELISA (as described above) for confirmation.

Example 4: Cloning of the Anti-CD32 Variable Domains from HB-217 mRNA is isolated from the cell line HB-217 (ATCC, antiCD32 antibody IV.3) and is used to prepare cDNA according to established routine protocols. The cDNA is further used as a template to amplify the regions of the genes coding for the of the light and the heavy chain of the Fab fragment of antibody IV.3 respectively. Upstream PCR primers, which prime from the 5' end of the variable regions, used for this amplification are derived from the published sequences of mouse variable regions (IMGT, the international ImMunoGeneTics information System®). Degenerate primers and/or mixtures of different primers are used as upstream primers. Downstream primers are designed such as to prime from the 31 end of the CL or the CH 1 domains respectively.

In a next step, the CL domain of the antibody IV.3 is removed and replaced by a selected CL domain modified by SMID technology which has binding affinity to TLR9, and which is selected as described above in examples 1-3. For this replacement, overlapping PCR can be used according to standard protocols. Alternatively, for joining VL to the SMID modified CL a uniquely cutting restriction site can be used which is either naturally occurring in the sequence or which is artificially introduced by site directed mutagenesis (as a silent mutation which does not change the amino acid sequence). For example, a BstAPI site can be generated in the hinge region between VL and CL by changing the sequence from:

```
                                    (SEQ ID No 65)
 K  R  A  D  A  A  P  T  V  S  I  F (SEQ ID No 66)
AAACGGGCTGATGCTGCACCAACTGTATCCATCTTC to:
                                    (SEQ ID No 65)
 K  R  A  D  A  A  P  T  V  S  I  F (SEQ ID No 15)
AAACGGGCAGATGCTGCACCAACTGTATCCATCTTC
``` the newly created BstAPI site is highlighted in the above sequence. The new sequence is introduced in the coding regions by amplifying the VL part and the CL part respectively with appropriately designed PCR primers, cutting the PCR products with BstAPI, ligating them, and amplifying the complete resulting ligation product with PCR primers as used initially for amplifying the original light chain part of the Fab fragment.

For expression of the modified Fab fragment, the genes coding for the heavy and the light chains are subsequently cloned in appropriate expression vectors, or together in one expression vector which allows the expression of two independent genes. As an expression system, bacteria, yeast, animal cells or any other suitable expression system can be used. For this example here, expression from one vector in the methylotrophic yeast *Pichia pastoris* will be shown.

The light chain part of the modified PCR fragment is cloned EcoRI/Kpn1 in the *Pichia pastoris* expression vector pPICZalphaA in the correct reading frame such as to fuse it functionally with the alpha-factor secretion signal sequence provided by the vector. Similarly, the heavy chain part of the Fab fragment is cloned in pPICZalphaA. In order to prepare the inserts for this cloning procedure, appropriately designed PCR primers are used which attach the needed restriction sites to the genes. At the 31 ends of both coding regions, a stop codon has to be inserted and provided by the PCR primers as well. The light chain expression cassette is then cut out from the vector with restriction enzymes BglII and BamHI, and the ends of the DNA are made blunt by treatment with Klenow fragment of DNA polymerase. The vector containing the inserted heavy chain part of the Fab is opened by a partial digest with restriction enzyme BglII, the DNA is made blunt by treatment with Klenow fragment of DNA polymerase, and the expression cassette coding for the light chain part is inserted. The partial digest of the heavy chain vector is necessary since the inserted heavy chain gene contains a BglII site. For screening of the final construct, care has to be taken that this internal BglII site has remained intact. The final construct has one Pme1 site which is used for linearizing the construct prior to transformation into *Pichia pastoris*. This linearization is advantageous for efficient integration of the expression vector in the host genome by homologous recombination. *Pichia pastoris* is transformed with the linearized expression vector using electroporation, transformed clones are selected with the antibiotic Zeocin for which the vector confers resistance, and supernatants of randomly picked clones are screened for expression of the Fab construct after induction of expression with methanol. For screening, e.g. a Fab-specific ELISA can be used. Production of the recombinant protein is achieved by culturing the transformed selected *Pichia* clone in a larger scale, preferable in shake flasks or in a fermenter, inducing expression by addition of methanol and purifying the recombinant protein by a chromatographic method. For these latter steps, routine protocols are used.

Example 5: Cloning of the Der P1I/F1 and Der P2/F2 derived T Cell Epitopes

The combination of the selected T cell epitopes formed by sequences B,A,E,H,G,C,F,D looks as follows (SEQ ID No 16):

```
CQIYPPNANKIREAL QSCRRPNAQRFGISNYCQIYPP YDGRTIIQRDNGYQPNYHAVNI
    (Seq: B)            (Seq. A)              (Seq. E)

VGY ENVVVTVKVMGDDGVLACAIAT KYTWNVPKIAPKSENVVVT IREALAQPQRYCRH
           (Seq. H)                (Seq. G)        (Seg. C)

YWT PCIIHRGKPFQLEAVFEAN RTVTPIRMQGGCGSCWAFSGVAATE
          (Seq. F)                (Seq. D)
```

In order to construct a synthetic gene coding for this amino acid sequence, in silico reverse translation can be used. Computer programs are available for this purpose, such as e.g. DNAWORKS, in order to clone the synthetic gene coding for the epitopes in frame with the gene coding for the heavy chain part of the framework, two restriction sites are selected which cut neither on this coding region nor on the vector pPICZalphaA. For example, AccIII and SpeI can be used for this purpose. These two restriction sites are attached to the gene coding for the heavy chain part of the Fab by using appropriately designed PCR primers for the cloning procedure as described above. Furthermore, care has to be taken not to have a stop codon at the end of the coding region of the heavy chain part of the Fab, as the stop codon will be provided at the 3' end of the synthetic gene coding for the epitopes. Again, this construct with the two additional restriction sites located at its 3' end is cloned EcoRI/Kpn1 in the *Pichia pastoris* expression vector pPICZalphaA. The construct is then opened with the restriction enzymes AccIII and SpeI and the insert coding the epitopes in inserted. This insert is generated as follows:

The chosen amino acid sequence:

(SEQ ID No 16)

CQIYPPNANKIREAL *QSCRRPNAQRFGISNYCQIYPP* YDGRTIIQRDNGYQPNYHAVNIVGY *ENVVVTVKVMGDDGVLACAIAT* KYTWNVPKIAPKSENVVVT *IREALAQPQRYCRHYWT* PCIIHRGKPFQLEAVFEAN *RTVTPIRMQGGCGSCWAFSGVAATE* together with the chosen restriction sites, in this example AccIII at the 5' end and SpeI at the 3' end are used as input in the publicly available computer program DNAWORKS. In addition, a stop codon is added between the end of the epitope sequence and the SpeI site.

The parameters which the program uses for designing the oligonucleotides are left at the proposed standard values, and the program is instructed to avoid the sequences of the restriction sites which are necessary for the cloning and transformation steps, such as AccIII, SpeI and PmeI.

| | |
|---|---|
| AccIII: | tccgga |
| SpeI: | actagt |
| PmeI: | gtttaaac |

DNAWORKS generates a set of oligonucleotides which are overlapping and which represent both strands of the desired coding regions.

For example, the following set of 24 oligonucleotides is generated, from which the synthetic gene coding for the allergen epitopes is generated:

```
                                               (SEQ ID No 17)
1   TCCGGATGCCAAATTTACCCGCCAAACG                    28

                                               (SEQ ID No 18)
2   AGCCTCTCTGATCTTGTTCGCGTTTGGCGGGTAAATTTGG    40

                                               (SEQ ID No 19)
3   CGAACAAGATCAGAGAGGCTTTGCAATCTTGCAGGAGGCC    40

                                               (SEQ ID No 20)
4   TATGCCGAATCTCTGCGCATTGGGCCTCCTGCAAGATTGC    40

                                               (SEQ ID No 21)
5   GCGCAGAGATTCGGCATATCCAACTACTGCCAGATCTACC    40

                                               (SEQ ID No 22)
6   GTACGCCCATCGTATGGGGGGTAGATCTGGCAGTAGTTGG    40

                                               (SEQ ID No 23)
7   CCCATACGATGGGCGTACAATCATACAGCGTGATAACGGC    40
```

-continued

```
                                 (SEQ ID No 24)
 8  GCGTGGTAGTTAGGCTGATAGCCGTTATCACGCTGTATGA  40

                                 (SEQ ID No 25)
 9  TATCAGCCTAACTACCACGCCGTGAACATCGTCGGCTACG  40

                                 (SEQ ID No 26)
10  TCACAGTAACCACGACATTCTCGTAGCCGACGATGTTCAC  40

                                 (SEQ ID No 27)
11  AGAATGTCGTGGTTACTGTGAAGGTAATGGGCGATGACGG  40

                                 (SEQ ID No 28)
12  AGCTATGGCGCAAGCTAGAACCCCGTCATCGCCCATTACC  40

                                 (SEQ ID No 29)
13  TCTAGCTTGCGCCATAGCTACCAAGTACACTTGGAACGTA  40

                                 (SEQ ID No 30)
14  TTTTCGGCGCAATTTTGGGTACGTTCCAAGTGTACTTGGT  40

                                 (SEQ ID No 31)
15  CCCAAAATTGCGCCGAAAAGTGAAAACGTCGTAGTGACCA  40

                                 (SEQ ID No 32)
16  TGAGCCAATGCCTCCCTTATGGTCACTACGACGTTTTCAC  40

                                 (SEQ ID No 33)
17  AGGGAGGCATTGGCTCAACCTCAAAGATACTGCAGACACT  40

                                 (SEQ ID No 34)
18  TTATGCAGGGCGTCCAGTAGTGTCTGCAGTATCTTTGAGG  40

                                 (SEQ ID No 35)
19  ACTGGACGCCCTGCATAATCCACCGTGGTAAACCCTTTCA  40

                                 (SEQ ID No 36)
20  CTTCGAACACTGCCTCAAGTTGAAAGGGTTTACCACGGTG  40

                                 (SEQ ID No 37)
21  ACTTGAGGCAGTGTTCGAAGCTAACAGGACGGTAACGCCA  40

                                 (SEQ ID No 38)
22  CCGCACCCACCTTGCATACGAATTGGCGTTACCGTCCTGT  40

                                 (SEQ ID No 39)
23  TGCAAGGTGGGTGCGGGTCTTGTTGGGCTTTTTCTGGTGT  40

                                 (SEQ ID No 40)
24  ACTAGTTTATTCAGTAGCAGCCACACCAGAAAAAGC-     42
    CCAACA
```

These 24 oligonucleotides are dissolved, mixed together, boiled for several minutes and then cooled down to room temperature slowly to allow annealing. In a subsequent PCR steps using large amounts of the two bordering primers (primers #1 and #24), the annealed gene is amplified, the PCR product is then cleaved with the chosen restriction enzymes (AccIII and SpeI in this example), and cloned into the expression vector as described above, which contains as an insert the gene coding for the heavy chain part of the modified Fab. Preparation of the final expression vector containing both chains, transformation of *Pichia pastoris*, selection of clones and screening for producing clones is done as described above. Expression and purification of the recombinant protein is performed by following standard protocols.

Example 6: Fusion of VH and VL of the Anti-CD32 Antibody IV.3 Fusion with Anti-TLR9CH3 Domains (SMIDS)

All molecular modeling was done with Swiss-PdbViewer 3.7.

As a homology model for a mouse Fab fragment, the structure file 2BRR.pdb from the Protein Data Bank is used, and 1OQO.pdb is used as a source for the structure of a human IgG CH3 domain.

Molecular models of VH and VL of the IV.3 antibody are made with the "first approach mode" of the Swissmodel system using the amino acid sequences of VH and VL respectively.

Using the "magic fit" function of the Swiss-PdbViewer, two copies of the CH3 domain structure from 1OQO.pdb are fitted onto the CH1 and the CL domain respectively of 2BRR.pdb. Subsequently, the molecular models of the IV.3 VH and VL respectively are fitted (again using "magic fit") onto VH and VL of 2BRR.pdb.

For construction of a Fab-like protein in which CH 1 and CL are both replaced by a CH3 domain, it is necessary to decide at which point the sequence of VH should be ended and connected to the sequence of CH3, and at which point the sequence of VL should be ended and connected to the sequence of CH3. For both constructs, a point is chosen at which the main chain of the superimposed structures and models (see above) shows an optimal overlap.

For the light chain, it was found that the sequence up to Ala114 (numbering from 2BRR.pdb) will be used an connected to Pro343 (numbering from 1OQO.pdb) of the CH3 domain. The point of connection between these two sequences therefore reads as follows (VL part is underlined):

- - - <u>Lys112-Arg113-Ala114</u>-Pro343-Arg344-Glu345- -

In order to allow joining of the two coding sequences using restriction enzyme sites and DNA ligation, the sequence near the point of connection is changed by silent mutation to introduce a unique Xho1 site (ctcgag, underlined) as follows:

```
                         (SEQ ID No 41)
K  R  A  P  R  E

                         (SEQ ID No 42)
AAACGGGCTCCTCGAGAA
```

For later insertion of the allergen epitopes, an AscI site (ggcgcgcc) is introduced just before the stop codon of the construct plus an extra base for maintenance of the reading frame:

```
ggg cgc gcc
Gly Arg Ala
```

Furthermore, for cloning into the expression vector pPICZalphaA (*Pichia pastoris* expression system, Invitrogen), an EcoRI site (gaattc) is added to the 5'-end (N-terminus) and a Kpn1 site (ggtacc) to the 3'-end (C-terminus) of the construct.

The CH3 domain to be fused to VH and VL respectively selected as part of the construct can be a wild type human IgG CH3 domain which can serve as a negative control, or a CH3 domain previously engineered by SMID technology and selected to bind specifically to TLR9. In this example here, the sequence of clone A23, which binds specifically to TLR9 and which was described in the patent application PCT/EP2006/050059 is fused to both, VH and VL.

Therefore, the complete sequence of the VL-CH3 fusion protein has the following amino acid sequence (VL part is underlined), (SEQ ID No 43):

<u>DIVMTQAAPS VPVTPGESVS ISCRSSKSLL HTNGNTYLHW</u>

<u>FLQRPGQSPQ LLIYRMSVLA SGVPDRFSGS GSGTAFTLSI</u>

<u>SRVEAEDVGV FYCMQHLEYP LTFGAGTKLE LKRA</u>PREPQV

-continued

```
YTLPPSRDEL GIAQVSLTCL VKGFYPSDIA VEWESNGQPE

NNYKTTPPVL DSDGSFFLYS KLTVLGRRWT LGNVFSCSVM

HEALHNHYTQ KSLSLSPGK&
```

Nucleic acid sequence of the VL-CH3 fusion protein (restriction sites are underlined), (SEQ ID No 44):

```
gaattcGACA TTGTGATGAC CCAGGCTGCA CCCTCTGTAC

CTGTCACTCC TGGAGAGTCA GTATCCATCT CCTGCAGGTC

TAGTAAGAGT CTCCTGCATA CTAATGGCAA CACTTACTTG

CATTGGTTCC TACAGAGGCC AGGCCAGTCT CCTCAGCTCC

TGATATATCG GATGTCCGTC CTTGCCTCAG GAGTCCCAGA

CAGGTTCAGT GGCAGTGGGT CAGGAACTGC TTTCACACTG

AGCATCAGTA GAGTGGAGGC TGAGGATGTG GGTGTTTTTT

ACTGTATGCA ACATCTAGAA TATCCGCTCA CGTTCGGTGC

TGGGACCAAG CTGGAACTGA AACGGGCTCC TCGAGAACCA

CAGGTGTACA CCCTGCCCCC ATCCCGGGAC GAGCTCGGCA

TCGCGCAAGT CAGCCTGACC TGCCTGGTCA AAGGCTTCTA

TCCCAGCGAC ATCGCCGTGG AGTGGGAGAG CAACGGGCAG

CCGGAGAACA ACTACAAGAC CACGCCTCCC GTGCTGGACT

CCGACGGCTC TTTCTTCCTC TACAGCAAGC TTACCGTGTT

GGGCCGCAGG TGGACCCTGG GGAACGTCTT CTCATGCTCC

GTGATGCATG AGGCTCTGCA CAACCACTAC ACACAGAAGA

GCCTCTCCCT GTCTCCGGGT AAATGAgggc gcgccggtac c
```

For the heavy chain, it was found that the sequence up to ThM 23 (numbering from 2BRR.pdb) should be used an connected to Arg344 (numbering from 1OQO.pdb) of the CH3 domain. The point of connection between these two sequences therefore reads as follows (VH part is underlined): - - -Ala121-Lys122-Thr123-Arg344-Glu345-Pro346 - - -

In order to allow joining of the two coding sequences using restriction enzyme sites and DNA ligation, the sequence near the point of connection was changed by silent mutation to introduce a unique Xho1 site (ctcgag, underlined) as follows:

```
                                (SEQ ID No 45)
A  K  T  R  E  P

                                (SEQ ID No 46)
GCCAAAACTCGAGAACCA
```

Furthermore, for cloning into the expression vector pPICZalphaA (*Pichia pastoris* expression system, Invitrogen), an EcoRI site (gaattc) is added to the 5'-end (N-terminus) and an Xba1 site (tctaga) to the 3'-end (C-terminus) of the construct. No stop codon is added to this sequence and the Xba1 site is placed in the correct reading frame so as to fuse the construct to the Hexa-His-tag provided by the vector for later purification of the protein using immobilized metal affinity chromatography.

Therefore, the complete sequence of the VH-CH3 fusion protein has the following amino acid sequence (VH part is underlined), (SEQ ID No 47):

```
EVQLQQSGPE LKKPGETVKI SCKASGYTFT NYGMNWVKQA

PGKGLKWMGW LNTYTGESIY PDDFKGRFAF SSETSASTAY

LQINNLKNED MATYFCARGD YGYGGPLDYW GQGTSVTVSS

AKTREPQVYT LPPSRDELGI AQVSLTCLVK GFYPSDIAVE

WESNGQPENN YKTTPPVLDS DGSFFLYSKL TVLGRRWTLG

NVFSCSVMHE ALHNHYTQKS LSLSPGKSLE QKLISEEDLN

SAVDHHHHHH&
```

Nucleic acid sequence of the VH-CH3 fusion protein (restriction sites are underlined), (SEQ ID No 48):

```
GAATTCGAGG TTCAGCTTCA GCAGTCTGGA CCTGAGCTGA

AGAAGCCTGG AGAGACAGTC AAGATCTCCT GCAAGGCTTC

TGGGTATACC TTCACAAACT ATGGAATGAA CTGGGTGAAG

CAGGCTCCAG GAAAGGGTTT AAAGTGGATG GGCTGGTTAA

ACACCTACAC TGGAGAGTCA ATATATCCTG ATGACTTCAA

GGGACGGTTT GCCTTCTCTT CGGAAACCTC TGCCAGCACT

GCCTATTTGC AGATCAACAA CCTCAAAAAT GAGGACATGG

CTACATATTT CTGTGCAAGA GGGGACTATG GTTACGACGA

CCCTTTGGAC TACTGGGGTC AAGGAACCTC AGTCACCGTC

TCCTCAGCCA AAACTCGAGA ACCACAGGTG TACACCCTGC

CCCCATCCCG GGACGAGCTC GGCATCGCGC AAGTCAGCCT

GACCTGCCTG

GTCAAAGGCT TCTATCCCAG CGACATCGCC GTGGAGTGGG

AGAGCAACGG GCAGCCGGAG AACAACTACA AGACCACGCC

TCCCGTGCTG GACTCCGACG GCTCTTTCTT CCTCTACAGC

AAGCTTACCG TGTTGGGCCG CAGGTGGACC CTGGGGAACG

TCTTCTCATG CTCCGTGATG CATGAGGCTC TGCACAACCA

CTACACACAG AAGAGCCTCT CCCTGTCTCC GGGTAAATCT

CTAGAACAAA AACTCATCTC AGAAGAGGAT CTGAATAGCG

CCGTCGACCA TCATCATCAT CATCATTGA
```

Detailed Cloning Plan

Heavy Chain:

The VH region of antibody IV.3 is PCR-amplified with primers 4.3HupEco and 4.3HdownXho, and subsequently digested with EcoRI and Xho1. The CH3 SMID-engineered clone A23 is PCR-amplified with primers CH3upXhoA and CH3XBA2 and subsequently digested with Xho1 and Xba1. The VH sequence and the CH3 sequence are ligated together via the Xho1 site and then ligated into pPICZalphaA (Invitrogen), which was previously digested with EcoRI and Xba1. The resulting vector is named pPICHA23.

Primer List:

```
                                         (SEQ ID No 49)
4.3HUPECO    cagagaattc gaggttcagc ttcagcagtc

                                         (SEQ ID No 50)
4.3HDOWNXHO  gatgctcgag ttttggctga ggagacggtg
```

-continued

```
                                    (SEQ ID No 51)
CH3UPXHOA     aaaactcgag aaccacaggt gtacaccctg cc

                                    (SEQ ID No 52)
CH3XBA2       actgatctag acctttaccc ggagacaggg agag
```

Light Chain:

The VL region of antibody IV.3 is PCR-amplified with primers 4.3LupEco and 4.3LdownXho, and subsequently digested with EcoRI and Xho1. The CH3 SMID-engineered clone A23 is PCR-amplified with primers CH3upXhoB and CH3StopKpn and subsequently digested with Xho1 and Kpn1. The VL sequence and the CH3 sequence are ligated together via the Xho1 site and then ligated into pPICZalphaA (Invitrogen), which was previously digested with EcoRI and Kpn1. The resulting vector is named pPICLA23.

Primer List:

```
                                    (SEQ ID No 53)
4.3LUPECO      gatagaattc gacattgtga tgacccaggc tg

                                    (SEQ ID No 54)
4.3LDOWNXHO    attactcgag gagcccgttt cagttccagc t

                                    (SEQ ID No 55)
CH3UPXHOB      gctcctcgag aaccacaggt gtacaccctg cc

                                    (SEQ ID No 56)
CH3STOPKPN     acgtggtacc tcaggcgcgc cctttacccg

               gagacaggga gag
```

Combination of the Two Expression Cassettes in One Vector

The light chain cassette is cut out with BglII (pos.1) and BamHI (pos. 2319) from pPICLA23 (4235 bp), and the 2319 bp fragment is purified via preparative gel electrophoresis. The 1916 bp fragment is discarded. The vector pPICHA23 (4219 bp) is digested with BamHI, and the previously purified 2319 bp fragment from pPICLA23 is inserted. The resulting *Pichia pastoris* expression vector, which carries two expression cassettes, one for the VL-CH3 fusion protein and on for the VH-CH3 fusion protein is screened so that both inserts that have same direction of transcription. The resulting vector pPICHLA23 (6537 bp) is then linearized before transformation into *Pichia pastoris* e.g. with BamHI or with BssSI, transformed into *Pichia pastoris* by electroporation, and positive transformants are selected with Zeocin. Several clones are screened for expression of the recombinant protein. A clone is then selected for large scale production, and the recombinant fusion protein is purified by immobilized-metal-affinity chromatography using standard procedures. All *Pichia* manipulation, culturing and expression is done by following standard protocols (Invitrogen).

Insertion of allergen epitopes into the vector pPICHLA23 and expression of the recombinant fusion protein The sequence encoding the allergen epitopes as described in example 5 is inserted into the vector pPICHLA23 as follows:

The vector is digested with AscI (4174-4182) which leads to its linearization. In this AscI site, the DNA sequence encoding the allergen epitopes is inserted. The sequence encoding the allergen epitopes is amplified with primers EpiTLRI and EpiTLR2 in order to attach AscI sites to both ends of the sequence.

Primer List

```
                                    (SEQ ID No 57)
EpiTLR1     TAAAGGGCGC GCCTCCGGAT GCCAAATTTA CC

                                    (SEQ ID No 58)
EpiTLR2     TACCTCAGGC GCGCCTTATT CAGTAGCAGC CACAC
```

The resulting PCR product is digested with AscI and ligated into the previously digested vector. The resulting vector is named pHLA23EP (7046 bp). *Pichia* transformation, expression and purification of the recombinant fusion protein is performed as described above for the construct that has no epitopes inserted.

VL of Antibody IV.3

Amino Acid Sequence:

```
                                    (SEQ ID No 59)
DIVMTQAAPS VPVTPGESVS ISCRSSKSLL HTNGNTYLHW

FLQRPGQSPQ LLIYRMSVLA SGVPDRFSGS GSGTAFTLSI

SRVEAEDVGV FYCMQHLEYP LTFGAGTKLE LKRA
```

Nucleic Acid Sequence:

```
                                    (SEQ ID No 60)
GACATTGTGA TGACCCAGGC TGCACCCTCT GTACCTGTCA

CTCCTGGAGA GTCAGTATCC ATCTCCTGCA GGTCTAGTAA

GAGTCTCCTG CATACTAATG GCAACACTTA CTTGCATTGG

TTCCTACAGA GGCCAGGCCA GTCTCCTCAG CTCCTGATAT

ATCGGATGTC CGTCCTTGCC TCAGGAGTCC CAGACAGGTT

CAGTGGCAGT GGGTCAGGAA CTGCTTTCAC ACTGAGCATC

AGTAGAGTGG AGGCTGAGGA TGTGGGTGTT TTTTACTGTA

TGCAACATCT AGAATATCCG CTCACGTTCG GTGCTGGGAC

CAAGCTGGAA CTGAAACGGG CT
```

VH of Antibody IV.3

Amino Acid Sequence:

```
                                    (SEQ ID No 61)
EVQLQQSGPE LKKPGETVKI SCKASGYTFT NYGMNWVKQA

PGKGLKWMGW LNTYTGESIY PDDFKGRFAF SSETSASTAY

LQINNLKNED MATYFCARGD YGYDDPLDYW GQGTSVTVGS AKT
```

Nucleic Acid Sequence:

```
                                    (SEQ ID No 62)
GAGGTTCAGC TTCAGCAGTC TGGACCTGAG CTGAAGAAGC

CTGGAGAGAC AGTCAAGATC TCCTGCAAGG CTTCTGGGTA

TACCTTCACA AACTATGGAA TGAACTGGGT GAAGCAGGCT

CCAGGAAAGG GTTTAAAGTG GATGGGCTGG TTAAACACCT

ACACTGGAGA GTCAATATAT CCTGATGACT TCAAGGGACG
```

-continued

GTTTGCCTTC TCTTCGGAAA CCTCTGCCAG CACTGCCTAT

TTGCAGATCA ACAACCTCAA AAATGAGGAC ATGGCTACAT

ATTTCTGTGC AAGAGGGGAC TATGGTTACG ACGACCCTTT

-continued

GGACTACTGG GGTCAAGGAA CCTCAGTCAC CGTCTCCTCA

GCCAAAACA

Final Expression Vector pPICHCLA23.seq. (SEQ ID No 63) Containing TLR9 and CD32 Binding Regions (6537 bp):

```
   1 agatctaaca tccaaagacg aaaggttgaa tgaaaccttt ttgccatccg acatccacag
  61 gtccattctc acacataagt gccaaacgca acaggagggg atacactagc agcagaccgt
 121 tgcaaacgca ggacctccac tcctcttctc ctcaacaccc acttttgcca tcgaaaaacc
 181 agcccagtta ttgggcttga ttggagctcg ctcattccaa ttccttctat taggctacta
 241 acaccatgac tttattagcc tgtctatcct ggcccccctg gcgaggttca tgtttgttta
 301 tttccgaatg caacaagctc cgcattacac ccgaacatca ctccagatga gggctttctg
 361 agtgtggggt caaatagttt catgttcccc aaatggccca aaactgacag tttaaacgct
 421 gtcttggaac ctaatatgac aaaagcgtga tctcatccaa gatgaactaa gtttggttcg
 481 ttgaaatgct aacggccagt tggtcaaaaa gaaacttcca aaagtcggca taccgtttgt
 541 cttgtttggt attgattgac gaatgctcaa aaataatctc attaatgctt agcgcagtct
 601 ctctatcgct tctgaacccc ggtgcacctg tgccgaaacg caaatgggga aacacccgct
 661 ttttggatga ttatgcattg tctccacatt gtatgcttcc aagattctgg tgggaatact
 721 gctgatagcc taacgttcat gatcaaaatt taactgttct aacccctact tgacagcaat
 781 atataaacag aaggaagctg ccctgtctta aacctttttt tttatcatca ttattagctt
 841 actttcataa ttgcgactgg ttccaattga caagcttttg attttaacga cttttaacga
 901 caacttgaga agatcaaaaa acaactaatt attcgaaacg atgagatttc cttcaatttt
 961 tactgctgtt ttattcgcag catcctccgc attagctgct ccagtcaaca ctacaacaga
1021 agatgaaacg gcacaaattc cggctgaagc tgtcatcggt tactcagatt tagaagggga
1081 tttcgatgtt gctgttttgc cattttccaa cagcacaaat aacgggttat tgtttataaa
1141 tactactatt gccagcattg ctgctaaaga agaaggggta tctctcgaga aaagagaggc
1201 tgaagctgaa ttcgaggttc agcttcagca gtctggacct gagctgaaga agcctggaga
1261 gacagtcaag atctcctgca aggcttctgg gtatacctte acaaactatg gaatgaactg
1321 ggtgaagcag gctccaggaa agggtttaaa gtggatgggc tggttaaaca cctacactgg
1381 agagtcaata tatcctgatg acttcaaggg acggtttgcc ttctcttcgg aaacctctgc
1441 cagcactgcc tatttgcaga tcaacaacct caaaaatgag gacatggcta catatttctg
1501 tgcaagaggg gactatggtt acgacgaccc tttggactac tggggtcaag gaacctcagt
1561 caccgtctcc tcagccaaaa ctcgagaacc acaggtgtac accctgcccc catcccggga
1621 tgagctgggc atcgcgcaag tcagcctgac ctgcctggtc aaaggcttct atcccagcga
1681 catcgccgtg gagtgggaga gcaacgggca gccggagaac aactacaaga ccacgcctcc
1741 cgtgctggac tccgacggct ctttcttcct ctacagcaag cttaccgtgt tgggccgcag
1801 gtggaccctg gggaacgtct tctcatgctc cgtgatgcat gaggctctgc acaaccacta
1861 cacgcagaag agcctctccc tgtctccggg taaatctcta gaacaaaaac tcatctcaga
1921 agaggatctg aatagcgccg tcgaccatca tcatcatcat cattgagttt gtagccttag
1981 acatgactgt tcctcagttc aagttgggca cttacgagaa gaccggtctt gctagattct
2041 aatcaagagg atgtcagaat gccatttgcc tgagagatgc aggcttcatt tttgatactt
```

-continued 2101 ttttatttgt aacctatata gtataggatt tttttgtca ttttgtttct tctcgtacga 2161 gcttgctcct gatcagccta tctcgcagct gatgaatatc ttgtggtagg ggtttgggaa 2221 aatcattcga gtttgatgtt tttcttggta tttcccactc ctcttcagag tacagaagat 2281 taagtgagac cttcgtttgt gcagatccaa catccaaaga cgaaaggttg aatgaaacct 2341 ttttgccatc cgacatccac aggtccattc tcacacataa gtgccaaacg caacaggagg 2401 ggatacacta gcagcagacc gttgcaaacg caggacctcc actcctcttc tcctcaacac 2461 ccacttttgc catcgaaaaa ccagcccagt tattgggctt gattggagct cgctcattcc 2521 aattccttct attaggctac taacaccatg actttattag cctgtctatc ctggcccccc 2581 tggcgaggtt catgtttgtt tatttccgaa tgcaacaagc tccgcattac acccgaacat 2641 cactccagat gagggctttc tgagtgtggg gtcaaatagt ttcatgttcc ccaaatggcc 2701 caaaactgac agtttaaacg ctgtcttgga acctaatatg acaaaagcgt gatctcatcc 2761 aagatgaact aagtttggtt cgttgaaatg ctaacggcca gttggtcaaa aagaaacttc 2821 caaaagtcgg cataccgttt gtcttgtttg gtattgattg acgaatgctc aaaaataatc 2881 tcattaatgc ttagcgcagt ctctctatcg cttctgaacc ccggtgcacc tgtgccgaaa 2941 cgcaaatggg gaaacacccg ctttttggat gattatgcat tgtctccaca ttgtatgctt 3001 ccaagattct ggtgggaata ctgctgatag cctaacgttc atgatcaaaa tttaactgtt 3061 ctaaccccta cttgacagca atatataaac agaaggaagc tgccctgtct taaacctttt 3121 tttttatcat cattattagc ttactttcat aattgcgact ggttccaatt gacaagcttt 3181 tgattttaac gacttttaac gacaacttga gaagatcaaa aaacaactaa ttattcgaaa 3241 cgatgagatt tccttcaatt tttactgctg ttttattcgc agcatcctcc gcattagctg 3301 ctccagtcaa cactacaaca gaagatgaaa cggcacaaat tccggctgaa gctgtcatcg 3361 gttactcaga tttagaaggg gatttcgatg ttgctgtttt gccattttcc aacagcacaa 3421 ataacgggtt attgtttata aatactacta ttgccagcat tgctgctaaa gaagaagggg 3481 tatctctcga gaaaagagag gctgaagctg aattcgacat tgtgatgacc caggctgcac 3541 cctctgtacc tgtcactcct ggagagtcag tatccatctc ctgcaggtct agtaagagtc 3601 tcctgcatac taatggcaac acttacttgc attggttcct acagaggcca ggccagtctc 3661 ctcagctcct gatatatcgg atgtccgtcc ttgcctcagg agtcccagac aggttcagtg 3721 gcagtgggtc aggaactgct ttcacactga gcatcagtag agtggaggct gaggatgtgg 3781 gtgtttttta ctgtatgcaa catctagaat atccgctcac gttcggtgct gggaccaagc 3841 tggaactgaa acgggctcct cgagaaccac aggtgtacac cctgcccccca tcccgggatg 3901 agctgggcat cgcgcaagtc agcctgacct gcctggtcaa aggcttctat cccagcgaca 3961 tcgccgtgga gtgggagagc aacgggcagc cggagaacaa ctacaagacc acgcctcccg 4021 tgctggactc cgacggctct ttcttcctct acagcaagct taccgtgttg ggccgcaggt 4081 ggaccctggg gaacgtcttc tcatgctccg tgatgcatga ggctctgcac aaccactaca 4141 cgcagaagag cctctccctg tctccgggta aagggcgcgc ctgaggtacc tcgagccgcg 4201 gcggccgcca gctttctaga acaaaaactc atctcagaag aggatctgaa tagcgccgtc 4261 gaccatcatc atcatcatca ttgagtttgt agccttagac atgactgttc ctcagttcaa 4321 gttgggcact tacgagaaga ccggtcttgc tagattctaa tcaagaggat gtcagaatgc 4381 catttgcctg agagatgcag gcttcatttt tgatactttt ttatttgtaa cctatatagt 4441 ataggatttt ttttgtcatt ttgtttcttc tcgtacgagc ttgctcctga tcagcctatc 4501 tcgcagctga tgaatatctt gtggtagggg tttgggaaaa tcattcgagt ttgatgtttt -continued 4561 tcttggtatt tcccactcct cttcagagta cagaagatta agtgagacct tcgtttgtgc 4621 ggatccccca cacaccatag cttcaaaatg tttctactcc ttttttactc ttccagattt 4681 tctcggactc cgcgcatcgc cgtaccactt caaaacaccc aagcacagca tactaaattt 4741 tccctctttc ttcctctagg gtgtcgttaa ttacccgtac taaaggtttg gaaaagaaaa 4801 aagagaccgc ctcgtttctt tttcttcgtc gaaaaaggca ataaaaattt ttatcacgtt 4861 tctttttctt gaaatttttt tttttagttt ttttctcttt cagtgacctc cattgatatt 4921 taagttaata aacggtcttc aatttctcaa gtttcagttt cattttcttt gttctattac 4981 aacttttttt acttcttgtt cattagaaag aaagcatagc aatctaatct aaggggcggt 5041 gttgacaatt aatcatcggc atagtatatc ggcatagtat aatacgacaa ggtgaggaac 5101 taaaccatgg ccaagttgac cagtgccgtt ccggtgctca ccgcgcgcga cgtcgccgga 5161 gcggtcgagt tctggaccga ccggctcggg ttctcccggg acttcgtgga ggacgacttc 5221 gccggtgtgg tccgggacga cgtgaccctg ttcatcagcg cggtccagga ccaggtggtg 5281 ccggacaaca ccctggcctg ggtgtgggtg cgcggcctgg acgagctgta cgccgagtgg 5341 tcggaggtcg tgtccacgaa cttccgggac gcctccgggc cggccatgac cgagatcggc 5401 gagcagccgt gggggcggga gttcgccctg cgcgacccgg ccggcaactg cgtgcacttc 5461 gtggccgagg agcaggactg acacgtccga cggcggccca cgggtcccag gcctcggaga 5521 tccgtccccc ttttcctttg tcgatatcat gtaattagtt atgtcacgct tacattcacg 5581 ccctccccc acatccgctc taaccgaaaa ggaaggagtt agacaacctg aagtctaggt 5641 ccctatttat ttttttatag ttatgttagt attaagaacg ttatttatat ttcaaatttt 5701 tcttttttt ctgtacagac gcgtgtacgc atgtaacatt atactgaaaa ccttgcttga 5761 gaaggttttg ggacgctcga aggctttaat ttgcaagctg gagaccaaca tgtgagcaaa 5821 aggccagcaa aaggccagga accgtaaaaa ggccgcgttg ctggcgtttt tccataggct 5881 ccgcccccct gacgagcatc acaaaaatcg acgctcaagt cagaggtggc gaaacccgac 5941 aggactataa agataccagg cgtttccccc tggaagctcc ctcgtgcgct ctcctgttcc 6001 gaccctgccg cttaccggat acctgtccgc ctttctccct tcgggaagcg tggcgctttc 6061 tcaatgctca cgctgtaggt atctcagttc ggtgtaggtc gttcgctcca agctgggctg 6121 tgtgcacgaa ccccccgttc agcccgaccg ctgcgcctta tccggtaact atcgtcttga 6181 gtccaacccg gtaagacacg acttatcgcc actggcagca gccactggta acaggattag 6241 cagagcgagg tatgtaggcg gtgctacaga gttcttgaag tggtggccta actacggcta 6301 cactagaagg acagtatttg gtatctgcgc tctgctgaag ccagttacct tcggaaaaag 6361 agttggtagc tcttgatccg gcaaacaaac caccgctggt agcggtggtt tttttgtttg 6421 caagcagcag attacgcgca gaaaaaaagg atctcaagaa gatcctttga tcttttctac 6481 ggggtctgac gctcagtgga acgaaaactc acgttaaggg attttggtca tgagatc Final Expression Vector pHLA23EP.seq (SEQ ID No 64) Containing TLR9 and CD32 Binding Regions and Epitope Sequence (See SEQ ID No 16) (7046 bp):

1 agatctaaca tccaaagacg aaaggttgaa tgaaaccttt ttgccatccg acatccacag 61 gtccattctc acacataagt gccaaacgca acaggagggg atacactagc agcagaccgt 121 tgcaaacgca ggacctccac tcctcttctc ctcaacaccc acttttgcca tcgaaaaacc 181 agcccagtta ttgggcttga ttggagctcg ctcattccaa ttccttctat taggctacta -continued 241 acaccatgac tttattagcc tgtctatcct ggcccccctg gcgaggttca tgtttgttta 301 tttccgaatg caacaagctc cgcattacac ccgaacatca ctccagatga gggctttctg 361 agtgtggggt caaatagttt catgttcccc aaatggccca aaactgacag tttaaacgct 421 gtcttggaac ctaatatgac aaaagcgtga tctcatccaa gatgaactaa gtttggttcg 481 ttgaaatgct aacggccagt tggtcaaaaa gaaacttcca aaagtcggca taccgtttgt 541 cttgtttggt attgattgac gaatgctcaa aaataatctc attaatgctt agcgcagtct 601 ctctatcgct tctgaacccc ggtgcacctg tgccgaaacg caaatgggga aacacccgct 661 ttttggatga ttatgcattg tctccacatt gtatgcttcc aagattctgg tgggaatact 721 gctgatagcc taacgttcat gatcaaaatt taactgttct aacccctact tgacagcaat 781 atataaacag aaggaagctg ccctgtctta aacctttttt tttatcatca ttattagctt 841 actttcataa ttgcgactgg ttccaattga caagcttttg attttaacga cttttaacga 901 caacttgaga agatcaaaaa acaactaatt attcgaaacg atgagatttc cttcaatttt 961 tactgctgtt ttattcgcag catcctccgc attagctgct ccagtcaaca ctacaacaga 1021 agatgaaacg gcacaaattc cggctgaagc tgtcatcggt tactcagatt tagaagggga

1081 tttcgatgtt gctgttttgc cattttccaa cagcacaaat aacgggttat tgtttataaa 1141 tactactatt gccagcattg ctgctaaaga agaaggggta tctctcgaga aaagagaggc 1201 tgaagctgaa ttcgaggttc agcttcagca gtctggacct gagctgaaga agcctggaga 1261 gacagtcaag atctcctgca aggcttctgg gtataccttc acaaactatg gaatgaactg 1321 ggtgaagcag gctccaggaa agggtttaaa gtggatgggc tggttaaaca cctacactgg 1381 agagtcaata tatcctgatg acttcaaggg acggtttgcc ttctcttcgg aaacctctgc 1441 cagcactgcc tatttgcaga tcaacaacct caaaaatgag gacatggcta catatttctg 1501 tgcaagaggg gactatggtt acgacgaccc tttggactac tggggtcaag gaacctcagt 1561 caccgtctcc tcagccaaaa ctcgagaacc acaggtgtac accctgcccc catcccggga 1621 tgagctgggc atcgcgcaag tcagcctgac ctgcctggtc aaaggcttct atcccagcga 1681 catcgccgtg gagtgggaga gcaacgggca gccggagaac aactacaaga ccacgcctcc 1741 cgtgctggac tccgacggct ctttcttcct ctacagcaag cttaccgtgt tgggccgcag 1801 gtggaccctg gggaacgtct tctcatgctc cgtgatgcat gaggctctgc acaaccacta 1861 cacgcagaag agcctctccc tgtctccggg taaatctcta gaacaaaaac tcatctcaga 1921 agaggatctg aatagcgccg tcgaccatca tcatcatcat cattgagttt gtagccttag 1981 acatgactgt tcctcagttc aagttgggca cttacgagaa gaccggtctt gctagattct 2041 aatcaagagg atgtcagaat gccatttgcc tgagagatgc aggcttcatt tttgatactt 2101 ttttatttgt aacctatata gtataggatt ttttttgtca ttttgtttct tctcgtacga 2161 gcttgctcct gatcagccta tctcgcagct gatgaatatc ttgtggtagg ggtttgggaa 2221 aatcattcga gtttgatgtt tttcttggta tttcccactc ctcttcagag tacagaagat 2281 taagtgagac cttcgtttgt gcagatccaa catccaaaga cgaaaggttg aatgaaacct 2341 ttttgccatc cgacatccac aggtccattc tcacacataa gtgccaaacg caacaggagg 2401 ggatacacta gcagcagacc gttgcaaacg caggacctcc actcctcttc tcctcaacac 2461 ccacttttgc catcgaaaaa ccagcccagt tattgggctt gattggagct cgctcattcc 2521 aattccttct attaggctac taacaccatg actttattag cctgtctatc ctggcccccc 2581 tggcgaggtt catgtttgtt tatttccgaa tgcaacaagc tccgcattac acccgaacat -continued 2641 cactccagat gagggctttc tgagtgtggg gtcaaatagt ttcatgttcc ccaaatggcc
2701 caaaactgac agtttaaacg ctgtcttgga acctaatatg acaaaagcgt gatctcatcc
2761 aagatgaact aagtttggtt cgttgaaatg ctaacggcca gttggtcaaa aagaaacttc
2821 caaaagtcgg cataccgttt gtcttgtttg gtattgattg acgaatgctc aaaaataatc
2881 tcattaatgc ttagcgcagt ctctctatcg cttctgaacc ccggtgcacc tgtgccgaaa
2941 cgcaaatggg gaaacacccg ctttttggat gattatgcat tgtctccaca ttgtatgctt
3001 ccaagattct ggtgggaata ctgctgatag cctaacgttc atgatcaaaa tttaactgtt
3061 ctaaccccta cttgacagca atatataaac agaaggaagc tgccctgtct taaacctttt
3121 tttttatcat cattattagc ttactttcat aattgcgact ggttccaatt gacaagcttt
3181 tgattttaac gacttttaac gacaacttga gaagatcaaa aaacaactaa ttattcgaaa
3241 cgatgagatt tccttcaatt tttactgctg ttttattcgc agcatcctcc gcattagctg
3301 ctccagtcaa cactacaaca gaagatgaaa cggcacaaat tccggctgaa gctgtcatcg
3361 gttactcaga tttagaaggg gatttcgatg ttgctgtttt gccattttcc aacagcacaa
3421 ataacgggtt attgtttata aatactacta ttgccagcat tgctgctaaa gaagaagggg
3481 tatctctcga gaaaagagag gctgaagctg aattcgacat tgtgatgacc caggctgcac
3541 cctctgtacc tgtcactcct ggagagtcag tatccatctc ctgcaggtct agtaagagtc
3601 tcctgcatac taatggcaac acttacttgc attggttcct acagaggcca ggccagtctc
3661 ctcagctcct gatatatcgg atgtccgtcc ttgcctcagg agtcccagac aggttcagtg
3721 gcagtgggtc aggaactgct ttcacactga gcatcagtag agtggaggct gaggatgtgg
3781 gtgtttttta ctgtatgcaa catctagaat atccgctcac gttcggtgct gggaccaagc
3841 tggaactgaa acgggctcct cgagaaccac aggtgtacac cctgccccca tcccgggatg
3901 agctgggcat cgcgcaagtc agcctgacct gcctggtcaa aggcttctat cccagcgaca
3961 tcgccgtgga gtgggagagc aacgggcagc cggagaacaa ctacaagacc acgcctcccg
4021 tgctggactc cgacggctct ttcttcctct acagcaagct taccgtgttg ggccgcaggt
4081 ggaccctggg gaacgtcttc tcatgctccg tgatgcatga ggctctgcac aaccactaca
4141 cgcagaagag cctctccctg tctccgggta aagggcgcgc ctccggatgc caaatttacc
4201 cgccaaacgc gaacaagatc agagaggctt tgcaatcttg caggaggccc aatgcgcaga
4261 gattcggcat atccaactac tgccagatct accccccata cgatgggcgt acaatcatac
4321 agcgtgataa cggctatcag cctaactacc acgccgtgaa catcgtcggc tacgagaatg
4381 tcgtggttac tgtgaaggta atgggcgatg acggggttct agcttgcgcc atagctacca
4441 agtacacttg gaacgtaccc aaaattgcgc cgaaaagtga aaacgtcgta gtgaccataa
4501 gggaggcatt ggctcaacct caaagatact gcagacacta ctggacgccc tgcataatcc
4561 accgtggtaa accctttcaa cttgaggcag tgttcgaagc taacaggacg gtaacgccaa
4621 ttcgtatgca aggtgggtgc gggtcttgtt gggctttttc tggtgtggct gctactgaat
4681 aaggcgcgcc tgaggtacct cgagccgcgg cggccgccag ctttctagaa caaaaactca
4741 tctcagaaga ggatctgaat agcgccgtcg accatcatca tcatcatcat tgagtttgta
4801 gccttagaca tgactgttcc tcagttcaag ttgggcactt acgagaagac cggtcttgct
4861 agattctaat caagaggatg tcagaatgcc atttgcctga gagatgcagg cttcattttt
4921 gatacttttt tatttgtaac ctatatagta taggattttt tttgtcattt tgtttcttct -continued

```
4981 cgtacgagct tgctcctgat cagcctatct cgcagctgat gaatatcttg tggtaggggt
5041 ttgggaaaat cattcgagtt tgatgttttt cttggtattt cccactcctc ttcagagtac
5101 agaagattaa gtgagacctt cgtttgtgcg gatcccccac acaccatagc ttcaaaatgt
5161 ttctactcct tttttactct tccagatttt ctcggactcc gcgcatcgcc gtaccacttc
5221 aaaacaccca agcacagcat actaaatttt ccctctttct tcctctaggg tgtcgttaat
5281 tacccgtact aaaggtttgg aaaagaaaaa agagaccgcc tcgtttcttt ttcttcgtcg
5341 aaaaaggcaa taaaaatttt tatcacgttt ctttttcttg aaattttttt ttttagtttt
5401 tttctctttc agtgacctcc attgatattt aagttaataa acggtcttca atttctcaag
5461 tttcagtttc atttttcttg ttctattaca actttttta cttcttgttc attagaaaga
5521 aagcatagca atctaatcta aggggcggtg ttgacaatta atcatcggca tagtatatcg
5581 gcatagtata atacgacaag gtgaggaact aaaccatggc caagttgacc agtgccgttc
5641 cggtgctcac cgcgcgcgac gtcgccggag cggtcgagtt ctggaccgac cggctcgggt
5701 tctcccggga cttcgtggag gacgacttcg ccggtgtggt ccgggacgac gtgaccctgt
5761 tcatcagcgc ggtccaggac caggtggtgc cggacaacac cctggcctgg gtgtgggtgc
5821 gcggcctgga cgagctgtac gccgagtggt cggaggtcgt gtccacgaac ttccgggacg
5881 cctccgggcc ggccatgacc gagatcggcg agcagccgtg ggggcgggag ttcgccctgc
5941 gcgacccggc cggcaactgc gtgcacttcg tggccgagga gcaggactga cacgtccgac
6001 ggcggcccac gggtcccagg cctcggagat ccgtccccct tttcctttgt cgatatcatg
6061 taattagtta tgtcacgctt acattcacgc cctcccccca catccgctct aaccgaaaag
6121 gaaggagtta gacaacctga agtctaggtc cctatttatt tttttatagt tatgttagta
6181 ttaagaacgt tatttatatt tcaaattttt cttttttttc tgtacagacg cgtgtacgca
6241 tgtaacatta tactgaaaac cttgcttgag aaggttttgg gacgctcgaa ggctttaatt
6301 tgcaagctgg agaccaacat gtgagcaaaa ggccagcaaa aggccaggaa ccgtaaaaag
6361 gccgcgttgc tggcgttttt ccataggctc cgcccccctg acgagcatca caaaaatcga
6421 cgctcaagtc agaggtggcg aaacccgaca ggactataaa gataccaggc gtttccccct
6481 ggaagctccc tcgtgcgctc tcctgttccg accctgccgc ttaccggata cctgtccgcc
6541 tttctccctt cgggaagcgt ggcgctttct caatgctcac gctgtaggta tctcagttcg
6601 gtgtaggtcg ttcgctccaa gctgggctgt gtgcacgaac cccccgttca gcccgaccgc
6661 tgcgccttat ccggtaacta tcgtcttgag tccaacccgg taagacacga cttatcgcca
6721 ctggcagcag ccactggtaa caggattagc agagcgaggt atgtaggcgg tgctacagag
6781 ttcttgaagt ggtggcctaa ctacggctac actagaagga cagtatttgg tatctgcgct
6841 ctgctgaagc cagttacctt cggaaaaaga gttggtagct cttgatccgg caaacaaacc
6901 accgctggta gcggtggttt ttttgtttgc aagcagcaga ttacgcgcag aaaaaaagga
6961 tctcaagaag atcctttgat cttttctacg gggtctgacg ctcagtggaa cgaaaactca
7021 cgttaaggga ttttggtcat gagatc
```

In the present application, all temperatures are in degrees Celsius. The following abbreviations are used:

CD32=FcγRII

TLR9=Toll like receptor 9

Der P1=*Dermatophagoides pteronissyus* major allergen 1

Der P2=*Dermatophagoides pteronissyus* major allergen 2

Der F1=*Dermatophagoides farinae* major allergen 1

Example 7: Exemplary Binders 7.1. CD32 Binding Region, Herein Also Called CD32 Binder The term "CD32 binding region" or "anti-CD32 moiety" as used herein shall mean a ligand specifically binding to the cellular target CD32, either CD32a, CD32b or both, CD32a and CD32b. The moiety can be any binding structure, such as derived from proteins, polypeptides or peptides, including antibodies and antibody fragments or composite molecules with a binding part. The binding part of the molecules or molecule complex of the invention can be comprised of proteins such as antibodies or antibody fragments, such as Fab, Fv, VH/VL, scFv, dAb, $F(ab)_2$, minibody, small mutated immunoglobulin domains, or other biological binders, such as soluble T-cell receptor, Darpins, etc. Antibodies and antibody fragments and derivatives may be generated and selected for binding to CD32 according to known methods such as hybridoma technology, B-cell cloning, phage display, ribosome display or cell surface display of antibody libraries, array screening of variant antibodies. Exemplary anti-CD32 moieties are scFv derived from the anti CD32 monoclonal antibody AT-10, IV.3, 2E6 or any other aCD32 monoclonal antibody.

A preferred CD32 binding region is an anti-CD32 antibody or derived from an anti-CD32 antibody, derived from an IgG1 Fc fragment, or a peptide specifically binding to CD32.

Specifically, the CD32 antibody is selected from the group consisting of a full-length antibody, an scFv or a VH/VL dimer, specifically binding the CD32.

A specific CD32 peptide is a CD32a peptide with the sequence of SEQ ID 66.

CD32a Binders:

Antibody specifically binding to CD32a: mAb IV.3 (Stuart et al. (1987) J. Exp. Med. 166: 1668)

ScFV derived from mAb IV.3
(VH-linker-VL): (SEQ ID 67)
EVQLQQSGPELKKPGETVKISCKASGYTFTNYGMNWVKQAPGKGLKWMG
WLNTYTGESIYPDDFKGRFAFSSETSASTAYLQINNLKNEDMATYFCAR
GDYGYDDPLDYWGQGTSVTVSSGGGGSGGGGSGGGGSDIVMTQAAPSVP
VTPGESVSISCRSSKSLLHTNGNTYLHWFLQRPGQSPQLLIYRMSVLAS
GVPDRFSGSGSGTAFTLSISRVEAEDVGVFYCMQHLEYPLTFGAGTKLE
LKGSI
Underlined: VH domain
Bold: HL domain
Normal type set. Flexible linker
(maybe any linker)

Anti-CD32a Peptide: Berntzen et al. (J. Biol. Chem. (2009) 284: 1126-1135): (SEQ ID 68): ADGAWAWVWLTETAVGAAK Group CD32a+b Binders:

Antibody specifically binding to CD32a and CD32b: mAb AT-10 (AbD Serotec)

ScFV derived from mAb AT-10
(VH-linker-VL) (SEQ ID 69):
EVKLEESGGGLVQPGGSMKLSCVASGFTFSYYWMNWVRQSPEKGLEWVA
EIRLKSNNYATHYAESVKGRFTISRDDSKNNVYLQMNNLRAEDTGIYYC
NRRDEYYAMDYWGQGTSVSVSSGGGGSGGGGSGGGGSDIVLTQSPGSLA
VSLGQRATISCRASESVDNFGISFMNWFQQKPGQPPRLLIYGASNQGSG
VPARFSGSGSGTDFSLNIHPVEEDDAAMYFCQQSKEVPWTFGGGTKLEI
KGSI
Underlined: VH domain
Bold: HL domain -continued Normal type set. Flexible linker
(maybe any linker)

IgG1 Fc fragment (CH2-CH3 domain) (SEQ ID 70):
(PKSCDKTHTCPPCP)PELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK
Between ( ) is hinge region may be omitted
Underlined: CH2 domain
Bold: CH3 domain

7.2 TLR9 Binding Region, Herein Also Called TLR9 Binder or TLR9 Ligand

The term "TLR9 binding region", "TLR9 binder" or "TLR9 ligand" as used herein is understood in the following way.

Toll-like receptor 9 (TLR9) recognizes unmethylated bacterial CpG DNA and initiates a signaling cascade leading to the production of proinflammatory cytokines. There are numerous structures or sequences that have been shown to act as a ligand of TLR9, i.e. bind to this receptor and thereby either activate (stimulate, upregulate) or de-activate (downregulate) TLR9. For instance, microbial DNA or synthetic DNA, e.g. synthetic CpG ODN may stimulate TLR9 with variations in the number and location of CpG dimers, as well as the precise base sequences flanking the CpG dimers. Synthetic CpG ODN differ from microbial DNA in that they have a partially or completely phosphorothioated backbone instead of the typical phosphodiester backbone and may or may not have a poly G tail at the 3' end, 5' end, or both.

The TLR9 ligand typically is coupled to the directed adjuvant component of the present vaccine by chemical coupling e.g. using the commercially available KIT from Solulink. A peptidic TLR9 ligand may be coupled using standard peptide chemistry or may be integrated using recombinant DNA technology.

Exemplary TLR9 ligands are ODN 2216 (group 1), ODN 2006/ODN 2007 (group2) and CpG-M362 (group 3).

The function of a TLR9 ligand or agonist or antagonist may be determined in a suitable assay, e.g. in the following way: pDCs are purified from blood of a healthy donor as described by Tel et al (Immunobiology 2012 October; 217 (10):1017-24) and subsequently incubated with the appropriate concentration of the TLR9 ligand. After 24 h IFNa is measured in the supernatant using standard ELISA protocols. For determination of the maturation state of the cells, pDCs are stained for expression of CD80 CD83 or CD86 using standard FACS procedures with commercially available specific antibodies before and after the incubation with the TLR9 ligand.

The number of reactive T cells that are activated upon exposure to the vaccine according to the invention may be determined by a number of methods including ELISPOT, FACS analysis, cytokine release, or T cell proliferation assays.

TLR9 ligand is a TLR9 agonist selected from the group consisting of CpG class A, in particular CpG-A (D)2 oligodeoxynucleotides (ODN), also known as "D"-type ODN.

Such TLR9 agonists induce a strong IFNa induction and minimal maturation of dendritic cells, and are herein called "group 1" TLR9 ligand.

According to another aspect of the invention, TLR9 ligand is a TLR9 agonist selected from the group consisting of CpG class B, in particular CpG-B (K)2 oligodeoxynucleotides (ODN), also known as "K"-type ODN. Such TLR9 agonists induce a weak IFNa induction and maturation of dendritic cells, and are herein called "group 2" TLR9 ligand.

According to another aspect of the invention, said TLR9 ligand specifically is a TLR9 agonist selected from the group consisting of CpG class C, also known as CpG-C2;3 oligodeoxynucleotides (ODN). Such TLR9 agonists induce IFNa and maturation of immature dendritic cells, and are herein called "group 3" TLR9 ligand.

According to another aspect of the invention, TLR9 ligand is a TLR9 antagonist selected from the group consisting of inhibitory ODNs oligodeoxynucleotides (sometimes called inhibitory CPGs), e.g. those which contain the inhibitory motif consisting of CCx(not-C)(not-C)xxGGG (x=any base)6. Specific inhibitory ODNs have proven not to induce IFNa and not to induce maturation of dendritic cells, also blocking activation through an agonist of TLR9.

Such TLR9 agonist or antagonist can be determined in a suitable cell based assay, which measures stable expression of either of IFNa, or at least one of the markers CD80, CD83 and CD86, which reflect the maturation of immature dendritic cells (DC). For this purpose plasmacytoid dendritic cells (pDCs) are purified from blood of a healthy donor as described by Tel et al (see above) and subsequently incubated with the appropriate concentration of the TLR9 ligand. After 24 h IFNa is measured in the supernatant using standard ELISA protocols. For determination of the maturation state of the cells, pDCs are stained for expression of CD80 CD83 or CD86 using standard FACS procedures with commercially available specific antibodies before and after the incubation with the TLR9 ligand.

The induction of IFNa may be determined by the level of IFNa expression and the respective increase with respect to a reference level. The increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

The maturation of immature dendritic cells may be determined by the level of expression of any of the markers CD80, CD83 and CD86. The respective increase relative to non-stimulated cells may be compared to the induction levels induced by established references for each type of CpG as defined by group 1, 2 or 3 TLR9 ligand and is typically between 30% and 300% of the respective reference, preferably at least 100%, more preferably at least 120%, at least 150%, at least 200% or at least 250%.

Specifically, the TLR9 agonist of group 1 and 3 would result in an increased IFNa expression and a TRL9 agonist of group 2 and 3 would lead to an increased expression of any of the DC maturation factors CD80, CD83 and CD86. The TLR9 antagonist would result in a reduced IFNa expression and a reduced expression of any of the DC maturation factors CD80, CD83 and CD86, even in the presence of a TLR9 agonist of either group 1-3.

CpG Class A
Group CpG-A:

```
ODN2216:                                    (SEQ ID 71)
GGGGGACGATCGTCGGGGGG
```

CpG Class B
Group CpG-B:
Natural Ligands:

```
ODN2006:                                    (SEQ ID 72)
TCGTCGTTTTGTCGTTTTGTCGTT
```

Peptidic Ligands (Peptides):

| Name | SEQ ID | Sequence |
|---|---|---|
| 12-2 | 73 | ESWDKFLSHYLP |
| 7-6 | 74 | TDWSWFY |
| 7-7 | 75 | YPVYWPW |
| 7-12 | 76 | EWWFYWP |
| 7-13 | 77 | WFPIEWW |
| 7-37 | 78 | DQVDIGY |
| 7-38 | 79 | THQVYIS |
| 7-12/13 | 80 | WFPIEWWFYWP |
| 12-1 | 81 | DSWQAFLTKFVL |
| 12-3 | 82 | HDIQWFWQHWNS |
| 12-4 | 83 | WSWWDHTFNYML |
| 12-6 | 84 | TTQQTWNVRYPY |
| 12-8 | 85 | DHTMPWTRNAKN |
| 12-12 | 86 | SWDPYWPFPWFS |
| 12-14 | 87 | AIYYVPSPMFTV |
| 12-16 | 88 | ETTLLKMWLAQM |
| 12-18 | 89 | YPWLDVAVVSLY |
| 12-20 | 90 | VPGWHYLATLRA |
| 12-21 | 91 | FDPLGSRDIKGS |

As a CpG mimic in the molecule or molecule complex of the invention, such immunostimulatory peptides may be preferably used. Likewise functionally active variants thereof may be used, which are fragments, mutants, or hybrids, including combinations thereof.

Functionally active variants are specifically characterized in that they stimulate pDCs, thereby inducing an increased level of IL-6 and/or TNFalpha and/or IFNalpha, as compared to a negative control.

Functionally active variants of the immunostimulatory TLR9 binding peptides specifically a) have at least 60% homology or sequence identity to any of the peptides of SEQ ID 73-91, preferably at least 70%, at least 80% or at least 90%;

b) are mutants of any of the peptides of SEQ ID 73-91, obtainable by modifying the parent amino acid sequence by insertion, deletion or substitution of one or more amino acids within the sequence or at either or both of the distal ends of the sequence, preferably less than 5, 4, 3, 2 or 1 point mutations; or c) are fragments of any of the peptides of SEQ ID 73-91 comprising at least 50% of the parent sequence, or at least 60%, at least 70%, at least 80%, or at least 90%; or at least 5 amino acids, preferably at least 6, at least 7, at least 8, at least 9, at least 10 or at least 11 amino acids.

Specific functional variants comprise a motif selected from the group consisting of EWWFYWP (SEQ ID 101), EWW (SEQ ID 102), WFY (SEQ ID 103), YWP (SEQ ID 104), and QVxI, x being any amino acid (SEQ ID 105).

CpG Class C

Group CpG-C

ODNM362:
(SEQ ID 92)
TCGTCGTCGTTCGAACGACGTTGAT

7.3 Exemplary CD32 Binding Products with Coils

A coiled coil is a structural motif in polypeptides or peptides, in which two to seven alpha-helices are coiled together like the strands of a rope. Such alpha helical regions are likely to form coiled-coil structures and may be involved in oligomerization of the coil repeats as measured in a suitable coiled coil interaction binding assay.

Specifically a dimer of alpha-helices can be formed by contacting the two monomers, such that the dimer is formed through an interaction with the two alpha helix coiled coil domains.

ScFV-coil 1 (IV.3):
(SEQ ID 93)
EVQLQQSGPELKKPGETVKISCKASGYTFTNYGMNWVKQAPGKGLKWMG
WLNTYTGESIYPDDFKGRFAFSSETSASTAYLQINNLKNEDMATYFCAR
GDYGYDDPLDYWGQGTSVTVSSGGGGSGGGGSGGGGSDIVMTQAAPSVP
VTPGESVSISCRSSKSLLHTNGNTYLHWFLQRPGQSPQLLIYRMSVLAS
GVPDRFSGSGSGTAFTLSISRVEAEDVGVFYCMQHLEYPLTFGAGTKLE
LKGSI*SAWSHPQFEKGPEVSALEKEVSALEKEVSALEKEVSALEKEVSA*
*LEK*

Underlined: VH domain
Bold: HL domain
Normal type set. Flexible linker (maybe any linker)
In italics: pepE coil plus C′ StrepTag II sequence and "GP" linker may be any flexible linker (StrepTag II may be removed or replaced by HIS Tag or any other tag)

ScFV-coil 2 (AT10):
(SEQ ID 94)
EVKLEESGGGLVQPGGSMKLSCVASGFTFSYYWMNWVRQSPEKGLEWVA
EIRLKSNNYATHYAESVKGRFTISRDDSKNNVYLQMNNLRAEDTGIYYC
NRRDEYYAMDYWGQGTSVSVSSGGGGSGGGGSGGGGSDIVLTQSPGSLA
VSLGQRATISCRASESVDNFGISFMNWFQQKPGQPPRLLIYGASNQGSG
VPARFSGSGSGTDFSLNIHPVEEDDAAMYFCQQSKEVPWTFGGGTKLEI
KGSI*SAWSHPQFEKGPEVSALEKEVSALEKEVSALEKEVSALEKEVSAL*

-continued

*EK*

Underlined: VH domain
Bold: HL domain
Normal type set. Flexible linker (maybe any linker)
In italics: pepE coil plus at C′ StrepTag II sequence and "GP" linker may be any flexible linker (StrepTag II may be removed or replaced by HIS Tag or any other tag)

Peptide-coil:
(SEQ ID 95)
ADGAWAWVWLTETAVGAAK*GPEVSALEKEVSALEKEVSALEKEVSALEK*
*EVSALEK*

In italics: pepE coil plus "GP" linker may be any flexible linker

IgG1 Fc fragment-coil:
(SEQ ID 94)
(PKSCDKTHTCPPCP)PELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK*GPEVSALEKEVSA*
*LEKEVSALEKEVSALEKEVSALEK*

Between ( ) is hinge region may be omitted
Underlined: CH2 domain
Bold CH3 domain
In italics: pepE coil plus "GP" linker may be any flexible linker

7.4. Exemplary TLR9 Binding Products with SH Group for Chemical Cross-Linking to the CD32 Binder Group CpG-A:

ODN2216_SH:
(SEQ ID 69)
GGGGGACGATCGTCGGGGGG-SH

In bold, flexible linker with SH group for chemical cross-linking to ScFV-coil (Maybe any linker and chemically reactive group e.g. NH2 suited for chemical crosslinking)

Group CpG-B:

Natural Ligands:

ODN2006_SH:
(SEQ ID 70)
TCGTCGTTTTGTCGTTTTGTCGTT-SH

Peptidic Ligands_SH:

| Name | SEQ ID | Sequence |
|---|---|---|
| 12-12_SH | 71 | SWDPYWPFPWFS**GGGS-SH** |
| 7-6_SH | 72 | TDWSWFY**GGGS-SH** |
| 7-7_SH | 73 | YPVYWPW**GGGS-SH** |
| 7-12_SH | 74 | EWWFYWP**GGGS-SH** |
| 7-13_SH | 75 | WFPIEWW**GGGS-SH** |
| 7-37_SH | 76 | DQVDIGY**GGGS-SH** |

-continued

| Name | SEQ ID | Sequence |
|---|---|---|
| 7-38_SH | 77 | THQVYISGGGS-SH |
| 7-12/13_SH | 78 | WFPIEWWFYWPGGGS-SH |
| 12-1_SH | 79 | DSWQAFLTKFVLGGGS-SH |
| 12-2_SH | 80 | ESWDKFLSHYLPGGGS-SH |
| 12-3_SH | 81 | HDIQWFWQHWNSGGGS-SH |
| 12-4_SH | 82 | WSWWDHTFNYMLGGGS-SH |
| 12-6_SH | 83 | TTQQTWNVRYPYGGGS-SH |
| 12-8_SH | 84 | DHTMPWTRNAKNGGGS-SH |
| 12-14_SH | 85 | AIYYVPSPMFTVGGGS-SH |
| 12-16_SH | 86 | ETTLLKMWLAQMGGGS-SH |
| 12-18_SH | 87 | YPWLDVAVVSLYGGGS-SH |
| 12-20_SH | 88 | VPGWHYLATLRAGGGS-SH |
| 12-21_SH | 89 | FDPLGSRDIKGSGGGS-SH |

In bold, flexible linker with SH group for chemical crosslinking to ScFV-coil (Maybe any linker and chemically reactive group e.g. NH2 suited for chemical crosslinking)

Group CpG-C

ODNM362_SH:
(SEQ ID 90)
TCGTCGTCGTTCGAACGACGTTGAT-SH

In bold flexible linker with SH group for chemical crosslinking to ScFV-coil (Maybe any linker and chemically reactive group e.g. NH2 suited for chemical crosslinking)

7.5 Exemplary Warhead, i.e. a Structure Comprising a CD32 Binder and a TLR9 Binder Any representative from the group of CD32 binders chemically linked by any method with any representative of the group of TLR9 binders, where preferably the TLR9 binders are coupled to available Lysines (K) in the CD32 binders e.g. Also mixtures of different TLR9 binders may be coupled e.g. CpG-B natural or peptidic binders.

ScFV-coil 1 (IV.3)
(SEQ ID 91)
EVQLQQSGPELKKPGETVKISCKASGYTFTNYGMNWVKQAPGKGLKWMG
WLNTYTGESIYPDDFKGRFAFSSETSASTAYLQINNLKNEDMATYFCAR
GDYGYDDPLDYWGQGTSVTVSSGGGGSGGGGSGGGGSDIVMTQAAPSVP
VTPGESVSISCRSSKSLLHTNGNTYLHWFLQRPGQSPQLLIYRMSVLAS
GVPDRFSGSGSGTAFTLSISRVEAEDVGVFYCMQHLEYPLTFGAGTKLE
LKGSISAWSHPQFEKGPEVSALEKEVSALEKEVSALEKEVSAL
EKEVSALEK
Lysines in coil structure (Italic) are preferred
or -continued Peptide-coil:
(SEQ ID 93)
ADGAWAWVWLTETAVGAAKGPEVSALEKEVSALEKEVSALEKE
VSALEKEVSALEK
Lysines in coil structure (Italic) are preferred

7.6. Exemplary Immunogen, Herein Also Called Antigen

The term "immunogen" as used herein shall mean one or more antigens triggering an immune response in a subject. The term "antigen" as used herein shall in particular refer to any antigenic determinant, which can be possibly recognized by a binding site of an antibody or is able to bind to the peptide groove of HLA class I or class II molecules and as such may serve as stimulant for specific T cells. The target antigen is either recognized as a whole target molecule or as a fragment of such molecule, especially substructures, e.g. a polypeptide or carbohydrate structure of targets, generally referred to as "epitopes", e.g. B-cell epitopes, T-cell epitope), which are immunologically relevant, i.e. are also recognizable by natural or monoclonal antibodies. Herein the use of T cell epitopes is preferred.

The term "epitope" as used herein according to the present invention shall in particular refer to a molecular structure which may completely make up a specific binding partner or be part of a specific binding partner to a binding site of modular antibody of the present invention. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably 8 to 50 amino acids, and more preferably between about 10-20 amino acids in the peptide. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide or carbohydrate chain. Linear epitopes can be contiguous or overlapping. Conformational epitopes are comprised of amino acids or carbohydrates brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

One or more epitopes of the same antigen or different antigens may be used according to the present invention, which can include antigens of all the self-antigens, pathogens, allergens or auto-antigens for which the regulation of the immune response is desired, e.g. against which induction of a substantial Th1-type response or Treg response (depending on the type of vaccine) in the host is desired.

In cancer disease an immune response to a self-antigen is desirable. The term "self-antigen" as used herein means any antigen, specifically polypeptide or peptide produced by a normal, healthy subject that does not elicit an immune response as such. These self-antigens may be produced at aberrant or high levels in certain disease states, including cancer disease, so called tumor associated antigens (TAAs). Self-antigens which are associated with auto-immune disease are herein called auto-antigens.

It is understood that the self-antigens can be naturally occurring, recombinantly or synthetically produced. It is also understood that the self-antigens need not be identical to the naturally produced antigen, but rather can include variations thereto having certain homology.

The choice of the self-antigen for use in cancer therapy depends on the type and stage of the cancer disease, and in particular on the expression pattern of a cancer cell such as derived from a tumor or metastases. Specific examples of selected tumor associated antigens possibly used in a vaccine according to the invention are Epithelial cell adhesion molecule (EpCAM), Lewis Y, alphafetoprotein (AFP) and carcinoembryonic antigen (CEA), HER2/Neu, VEGF, MUC-1, etc.

The choice of an auto-antigen for use in the therapy of auto-immune diseases depends on the type of the auto-immune disease. Specific examples of selected auto-immune disease associated antigens possibly used in a vaccine according to the invention are C1q, ADAMTS13, Desmogelin 3, keratin, gangliosides (e.g. GM1, GD1a, GQ1b), collagen type IV, IgM, cardiolipin, annexin A5, etc.

In some embodiments, the immunogen comprises one or more specific allergens. An "allergen" is an antigen which can initiate a state of hypersensitivity, or which can provoke an immediate hypersensitivity reaction in a subject already sensitized with the allergen. Allergens are commonly proteins or chemicals bound to proteins which have the property of being allergenic. However, allergens can also include organic or inorganic materials derived from a variety of synthetic or natural sources such as plant materials, metals, ingredients in cosmetics or detergents, latexes, or the like.

The choice of an allergen for use in the anti-allergy therapy depends on the type and severity of allergy. Specific examples of selected allergy associated antigens possibly used in a vaccine according to the invention are any allergen conventionally used as immunogen, specifically house dust mite allergens (e.g. Der p1, Der p2, Der p3, Der p5, Der p7/ - - - Der p23), cat dander, grass or tree pollen cockroach allergens, etc.

The choice of an antigen specifically inducing immune response against a pathogen for use in the prophylaxis or therapy of infectious diseases depends on the type of the pathogen, e.g. a microbial or viral infectious agent. Specific examples of selected pathogen derived antigens possibly used in a vaccine according to the invention are hepatitis B, hepatitis C, Cholera, HIV, Pertussis, Influenza, Typhoid, etc.

An exemplary antigen is an immunogen comprising one or more T cell epitopes of house dust mite allergens.

Specific antigens are selected from Immunogen 3 comprising the sequence of position 7-208 of SEQ ID 97, or Immunogen 5-12 comprising the sequence of position 1-364 of SEQ ID 98.

In a different embodiment, an exemplary antigen is a tumor associated antigen.

Immunogen 3 containing coil (Der P1 and Der P2 T cell epitopes based on human Class II expression): AA7-208 of SEQ ID 95.

(SEQ ID 95)

HHHHHHYYRYVAREQSCRRPNAQRFGISNYCQIYPPNVNKIREALAQTH

SAIAVDLRQMRTVTPIRMQGGCGSCWAFSGVAATESAYLQQYDIKYTWN

-continued

VPKIAPKSENVVVTVKVMGDDGVLACAIATHAKIRDDAFRHYDGRTIIQ

RDNGYQPNYHAVNIVGYSNAQGVDYWIVRNSWDTNWHEIKKVLVPGCHG

SEPCIIHRGKPFGGGSGGGS*GGKVSALKEKVSALKEKVSALKEKVSALK*

*EKVSALKE*

Underlined: HIS tag (may be removed)
In bold: a linker (can be any linker)
In italics: the pepK coil for interaction with warhead Immunogen 5-12 containing coil (~29 T cell epitopes of Der p1, Der p2, Der p3, Der p4, Der p7, Der p9, Der p10, Der p11, Der p14, Der p15, based on human Class II expression): AA1-364 of SEQ ID 96.

(SEQ ID 96)

GVLACAIATHAKIREQERLVKLETVKKSLEQEVRTLHVRIEEVEANALA

GGDLRQMRTVTPIRMQGGCGSCWEAHEQQIRIMTTKLKEAEARQQYDIK

YTWNVPKIAVNIVGYSNAQGVDYWIVRNSWDTNWYHNPHFIGNRSVITH

LMEDLKGELDMRNIQVRGLKQMKRVGDANVKSEDDAFRHYDGRTIIQRD

NGYQPNYLDEYWILTAAHCVDGQTVSKLIRSKVLGEKISYYRYVAREQS

CRRPNAQRFGISNYCVVVTVKVMGDDELHTYFNVNYTMHYYLNNGATRD

ILDEYWILTAAHCVAGQTASKLSIRYNSLKHSLFKYRPFKVNELNLEGE

FGRELQHKFRLMRNSQMEVEEGGGSHHHHHHGGGSGG*KVSALKEKVSAL*

*KEKVSALKEKVSALKEKVSALKE*

Underlined: HIS tag (may be removed)
In bold: a linker (can be any linker)
In italics: the pepK coil for interaction with warhead

7.7 Exemplary Allergy Vaccine SG100 Against House Dust Mite (HDM)

The exemplary molecule complex is formed by chemical linkage, fusion and/or affinity binding, in particular by a coiled-coil structure.

Warhead (based on ScFV-coil1 IV.3+ODNM362) is mixed with Immunogen 5-12 in a ratio which indicates 90% of warhead is complexed with immunogen, no free immunogen (molar ratio of ~1:1.5) and formulated on Alum.

7.8 Efficacy of SG100 in Rhesus Monkeys

Methods:

5 healthy house dust mite (HDM) naïve rhesus monkeys were immunized 3× with SG100 (100 μg/shot) absorbed on Alum) on d0, d14 and d28. Blood samples were taken on d0 and d49 for T cell activation and antibody production.

Antibody Immune Response:

Serum samples were tested in standard ELISA for IgG antibodies against warhead, immo 5-12 (Immo5), Der p1, Der p2,Der p5 and Der p7. The antigens were coated to maxisorb plates (1 μg/ml I PBS) overnight at 4° C., washed twice, blocked with PBS 1% BSA, washed twice incubated with the sera in a 1:1000 dilution for 1 h at 4° C., washed twice and subsequently detected with anti-human-IgG-PO (cross reactive with rhesus monkey IgG).

Cellular Immune Response:

Proliferation: PBMC (105/well) were cultured for 4 days (37° C./5% CO2/99% humidity) in 8 plex with medium, warhead (2 μg/ml), Immunogen (2 μg/ml), Der p1 (2 μg/ml), Der p2 (2 μg/ml), Der p5 (2 μg/ml) and Der p7 (2 μg/ml). As positive control Con A (Concanavaline A, Sigma) was used. Proliferation was measured by [3H]-thymidine (0.5 μCi/well) during the final 18 hrs of a 4 day culture. Cells were harvested for β-scintillation counting (Topcount NXT, Packerd, Ramsey, Minn., USA). Net counts per minutes were calculated by subtracting the counts of the medium control from the counts induced by the different antigens.

Cytokine Production:

From each well of the 8plex stimulations of the proliferation experiment, 50 μl supernatant was taken after 24 h and pooled. The pooled supernatants were tested for the presence of IFN and IL-4 using commercially available ELISA kits from U-Cytech, Utrecht The Netherlands).

Figure 5:
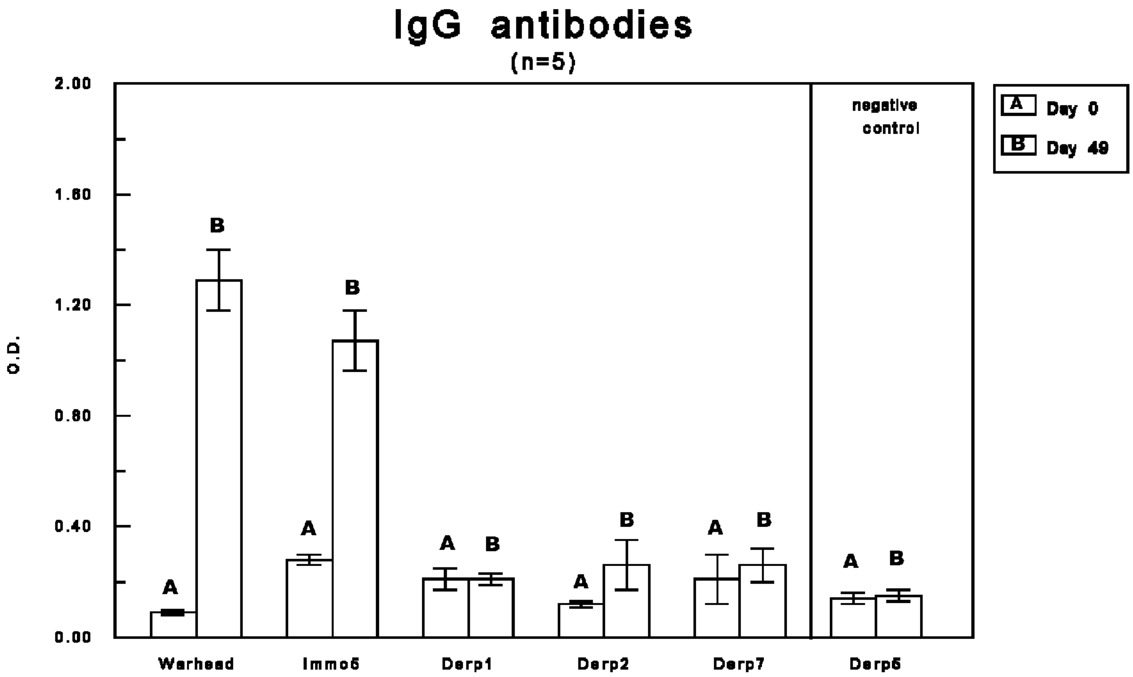
FIG. 5 is a graph showing the production of IgG antibodies in response to various immunogens.

Results:

Antibody Responses:

Strong IgG responses were measured against the warhead and the immunogen of SG100, but no antibodies were detected against Der p1, Der p2, Der p5 or Der p7 (FIG. 5), indicating that the animals were naive for the tested HDM allergens and that SG100 does not contain B cell epitopes, which cross-react with the tested HDM allergens.

Figure 6:
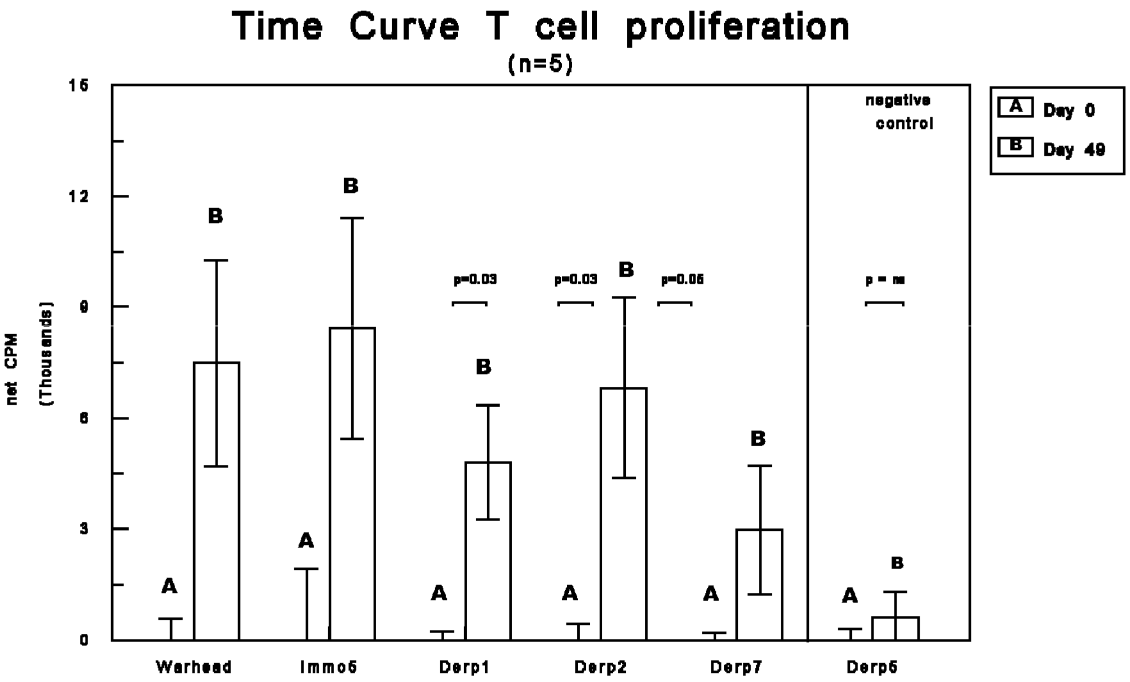
FIG. 6 is a graph of T cell proliferation in response to various immunogens.
Figure 7:
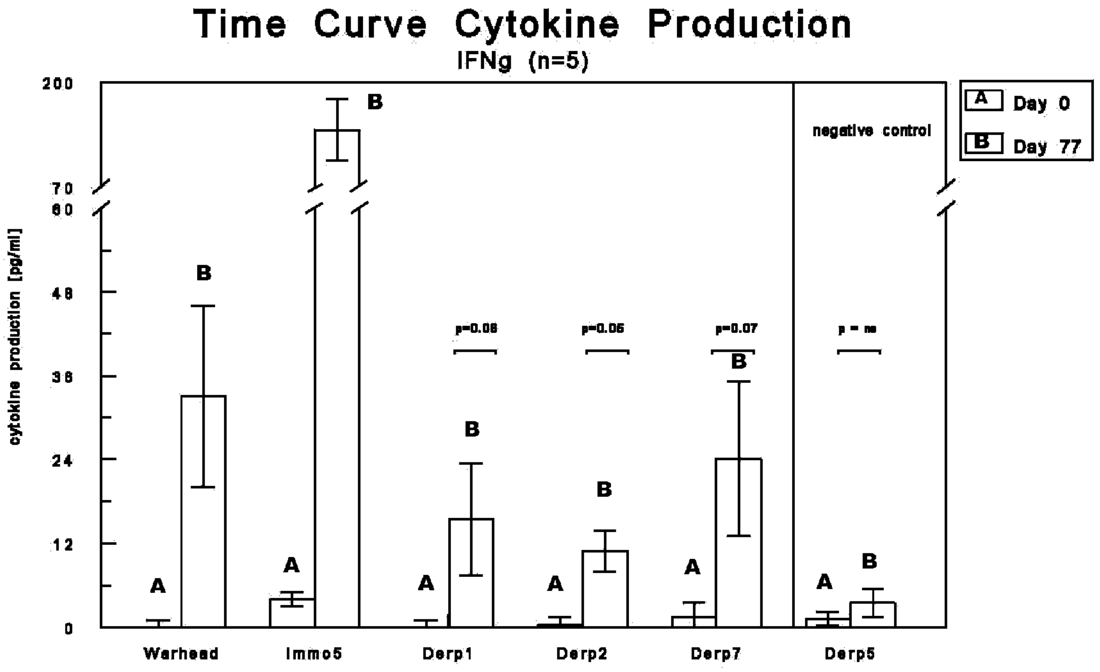
FIG. 7 is a graph of cytokine production in response to various immunogens.

T Cell Response:

In FIG. 6 it can be seen that PBMCs of all treated animals showed strong proliferation when stimulated in vitro with warhead, immo5, Der p1, Der p2, Der p'7, but not against Der p5. Also IFN but no IL-4 was measured in supernatants from in vitro cultures with warhead, immo5, Der p1, Der p2, Der p7 but not against Der p5. (FIG. 7). IL-4 was seen after stimulation with Con A (data not shown).

Conclusion:

Immunization with SG100 induces a Th1 type memory response against the vaccine as indicated by the presence of IgG antibodies as well the induction of T cells which produce IFN but not IL-4 when stimulated by warhead or Immo5. As expected, no IgG (=B cell memory) against Der p1, Der p2, Der p5 or Der p7 was induced because the vaccine does not contain B ell epitopes from these allergens. However, Th1 type memory, was induced against the T cell epitopes of the house dust mite allergens which are present in the vaccine Der p1, Der p2, Der p7. No Th1 type memory is induced against Der p5, which is not included in the vaccine. This confirms the concept of SG100.

7.7 Exemplary Vaccine, Warhead for Use in Oncology

ScFV-coil 1 (IV.3):

(SEQ ID 93)

EVQLQQSGPELKKPGETVKISCKASGYTFTNYGMNWVKQAPGKGLKWMG

WLNTYTGESIYPDDFKGRFAFSSETSASTAYLQINNLKNEDMATYFCAR

GDYGYDDPLDYWGQGTSVTVSSGGGGSGGGGSGGGGSDIVMTQAAPSVP

VTPGESVSISCRSSKSLLHTNGNTYLHWFLQRPGQSPQLLIYRMSVLAS

GVPDRFSGSGSGTAFTLSISRVEAEDVGVFYCMQHLEYPLTFGAGTKLE

LKGSI*SAWSHPQFEKGPEVSALEKEVSALEKEVSALEKEVSALEKEVSA*

*LEK*

Underlined: VH domain
Bold: HL domain
Normal type set. Flexible linker
(maybe any linker)
In italics: pepE coil plus C' StrepTag II -continued sequence and "GP" linker may be any flexible linker (StrepTag II may be removed or replaced by HIS Tag or any other tag)

Warhead with ODNM362 (SEQ ID NO:93):

EVQLQQSGPELKKPGETVKISCKASGYTFTNYGMNWVKQAPGKGLKWMG

WLNTYTGESIYPDDFKGRFAFSSETSASTAYLQINNLKNEDMATYFCAR

GDYGYDDPLDYWGQGTSVTVSSGGGGSGGGGSGGGGSDIVMTQAAPSVP

VTPGESVSISCRSSKSLLHTNGNTYLHWFLQRPGQSPQLLIYRMSVLAS

GVPDRFSGSGSGTAFTLSISRVEAEDVGVFYCMQHLEYPLTFGAGTKLE

LKGSISAWSHPQFEKGPEVSAL*E**KEVSALEKEVSALEKEVSALEK*

*EVSALE**K*

ODNM362_SH (SEQ ID 92)

TCGTCGTCGTTCGAACGACGTTGAT-SH

ODN-M362 may be coupled to any of the available lysines in ScFV-1-coil

Warhead (SG100):

ScFV-1-coil chemically linked with ODN-M362-SH. The preparation is a mix of ScFV-1-coil linked with 1 to 18 molecules ODN-M362 preferred is a mix with 1-6 molecules ODN-M362 coupled to ScFV-1-coil. All these mixes may be named warhead or ScFv-1-coil-M362.

Background:

Oncological targets for active immunotherapy are almost per definition autoantigens which are over expressed on tumor cells. These antigens are called tumor associated antigens (TAA) and the immune system is not able to respond against these antigens because they are recognized as self. A vaccine formulation that enables the immune system to generate a specific antibody and/or cellular immune response against an autoantigen is potentially suited for use as anti-tumor vaccination.

The Warhead of SG100 Enables an Autoimmunresponse:

24 mice (6/group) were immunized s.c. 2× with 35 μg in 150 μl ScFV-1-coil or with warhead (ScFV-1-coil-M362) either formulated on Alum or diluted in PBS. Immunizations were done on d0, and d14, sera were taken on d0 (before immunization) and d28 and analyzed for IgG1 and IgG2a against ScFV-1-coil (indicated as ScFV) and mAb IV.3 by standard ELISA. See FIG. 1.

As can be seen in FIG. 1, immunization with warhead induced a strong IgG1 and IgG2 response to ScFV-1-coil as well as to mAb IV.3 on day 28. A positive response was seen independent of the presence of Alum. Immunization with ScFV-1-coil only induced an IgG1 response against ScFV-1-coil and only in the presence of Alum, no IgG2a response was induced. These data fit with the concept that CpG (M362) induces a Th1 type response (IgG2a) and Alum induces a TH2 type response (IgG1). The response against ScFV-1-coil indicates that this protein is immunogenic in the mouse, indeed both the StrepTagII (amino acid sequence "SAWSHPQFEK" (SEQ ID 97)) and the pepE (amino acid sequence "EVSALEKEVSALEKEVSALEKEVSALEKEVSALEK" SEQ ID 100) were target of the IgG responses (data not shown). However ScFV-1-coil also contains "mouse-self-sequences" because the ScFV contains the VH and VL domains of the mouse mAb IV.3. Therefore, an immune response against IV.3 indicates the presence of autoimmune antibodies. Indeed, only the warhead with or without Alum was able to induce this type of immune response. Hence, the presence of M362 on the ScFV-1-coil is able to break the tolerance against the autoantigens VH and VL domain of the parent antibody. By combining an autoantigen e.g. a TAA, through high affinity interaction with pepE of the warhead, the warhead will be able to induce the necessary autoimmune response against the TAA. The complex of the warhead (ScFV-1-coil-M362) with the TAA forms a potent vaccine for the treatment of cancer with over expression of the TAA in the vaccine. Such a vaccine may be formulated with any adjuvants, e.g. on Alum.

Example 8: Comparison of the Stimulatory Capacity of the TLR9 Binder CPG on Human Plasmocytoid Dendritic Cells Administered in a Complex with an Anti-CD32 Antibody and in a Mixture

8.1 Material and Methods a) Plasmacytoid Dendritic (pDCs) cells:

Buffy coats were obtained from healthy volunteers according to institutional guidelines and pDCs were purified by positive isolation using anti-BDCA-4-conjugated magnetic microbeads (Miltenyi Biotec) and cultured in X-VIVO-15 medium (Cambrex) supplemented with 2% of decomplemented human AB+ serum. pDCs purity was routinely up to 95%, as assessed by double staining BDCA-2/CD123 (Miltenyi Biotec) in a FACS.

b) Stimulation of pDCs:

Freshly isolated pDCs were incubated with biotinylated anti-CD32 (10 μg/ml, clone AT10, AbD Serotec) in PBA (PBS containing 5% BSA) on ice for 30 minutes and washed twice with PBA, followed by an incubation with 10 μg/ml streptavidin-Alexa647 in PBA on ice for 30 minutes and two times washing with PBA. Subsequently, pDCs were incubated on ice for 15 minutes with either PBA, 5 μg/ml ODN-CpG C (M362, Axorra) in PBA or 5 μg/ml ODN-CpG C-3'-biotin in PBA (M362, Biosearch Technologies). Unbound ODN-CpG C was washed away three time with PBA and pDCs were cultured overnight (37° C., 5% CO2) in X-VIVO-15 medium (Cambrex), supplemented with 2% of decomplemented human AB+ serum. Supernatants were collected from pDC cultures after overnight stimulation, and IFNα production was analyzed with murine monoclonal capture and HRP-conjugated anti-IFNa antibodies (BenderMed systems) using standard ELISA procedures.

Figure 2:
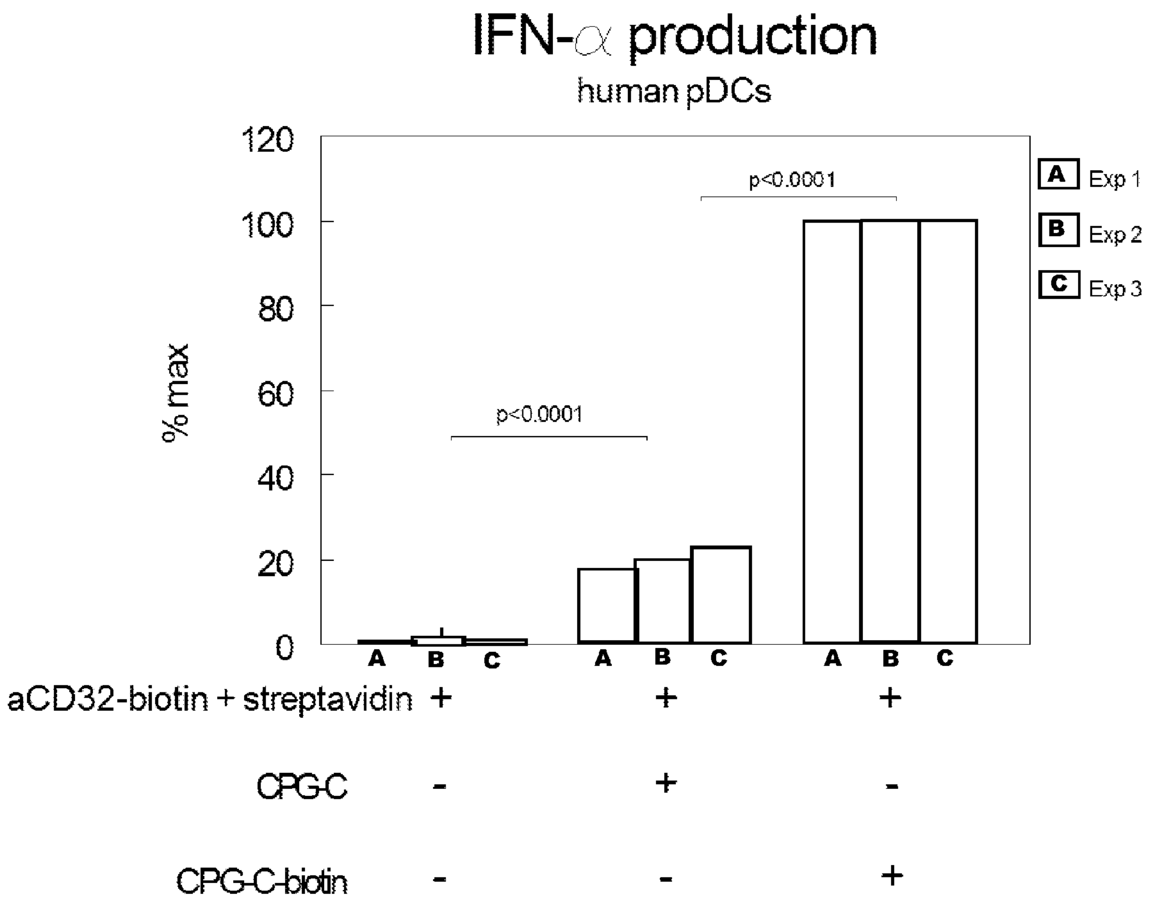
FIG. 2 is a graph showing IFN-α production by human pDCs after stimulation with CPG-C.

8.2. Results pDCs stimulated with 5 μg/ml CPG-C+aCD32-biotin/streptavidin-Alexa647 produced significantly more IFN-α, than pDCs stimulated with aCD32-biotin/streptavidin-Alexa647 alone. When aCD32 and CPG-C-biotin were complexed into one molecule, there was a statistically significant ($p<0.001$) positive synergistic effect on IFNα production compared to either aCD32-biotin/streptavidin-Alexa647 alone or aCD32-biotin/streptavidin-Alexa647+5 μg/ml CPG-C non-complexed. (FIG. 2). In a control experiment, there was no significant difference in IFNα production, when pDCs were stimulated with CPG-C versus CPG-biotin or CPG-C versus CPG-C+aCD32-biotin/streptavidin-Alexa647 (data not shown).

FIG. 2: IFNα Production of pDCS after Stimulation with CPG-C.

Maximum IFNα production in each experiment was seen when CPG-C-biotin was complexed with aCD32biotin through streptavidin. This was set at 100% and the ratio was calculated for aCD32-biotin with or without CPG-C (non complexed). Statistical analyses was done with the paired student t-test; $p<0.05$ were considered significant.

Example 9: Effect of a Molecule Complex Comprising Different Formats of Anti-CD32 And TLR9 Binding Moieties on the Immune Response as Determined on Plasmacytoid Dendritic (pDCs) Cells

Stimulation of pDCs with CpG Targeted to CD32, Employing an Anti-CD32 Single Chain Antibody

9.1 Material and Methods a) Plasmacytoid Dendritic (pDCs) cells:

Buffy coats were obtained from healthy volunteers according to institutional guidelines and pDCs were purified by positive isolation using anti-BDCA-4-conjugated magnetic microbeads (Miltenyi Biotec) and cultured in X-VIVO-15 medium (Cambrex) supplemented with 2% of decomplemented human AB+ serum. pDCs purity was routinely up to 95%, as assessed by double staining BDCA-2/CD123 (Miltenyi Biotec) in a FACS.

b) Stimulation of pDCs:

Freshly isolated pDCs were incubated with biotinylated anti-CD32 (10 μg/ml, clone AT10, AbD Serotec; ScFV from IV.3) in PBA (PBS containing 5% BSA) on ice for 30 minutes and washed twice with PBA, followed by an incubation with 10 μg/ml streptavidin-Alexa647 in PBA on ice for 30 minutes and two times washing with PBA. Subsequently, pDCs were incubated on ice for 15 minutes with either PBA, 5 μg/ml ODN-CpG C (M362, Axorra) in PBA or 5 μg/ml ODN-CpG C-3'-biotin in PBA (M362, Biosearch Technologies). Unbound ODN-CpG C was washed away three time with PBA and pDCs were cultured overnight (37° C., 5% CO2) in X-VIVO-15 medium (Cambrex), supplemented with 2% of decomplemented human AB+ serum. Supernatants were collected from pDC cultures after overnight stimulation, and IFNα production was analyzed with murine monoclonal capture and HRP-conjugated anti-IFNα antibodies (BenderMed systems) using standard ELISA procedures.

9.2. Results

Figure 3:
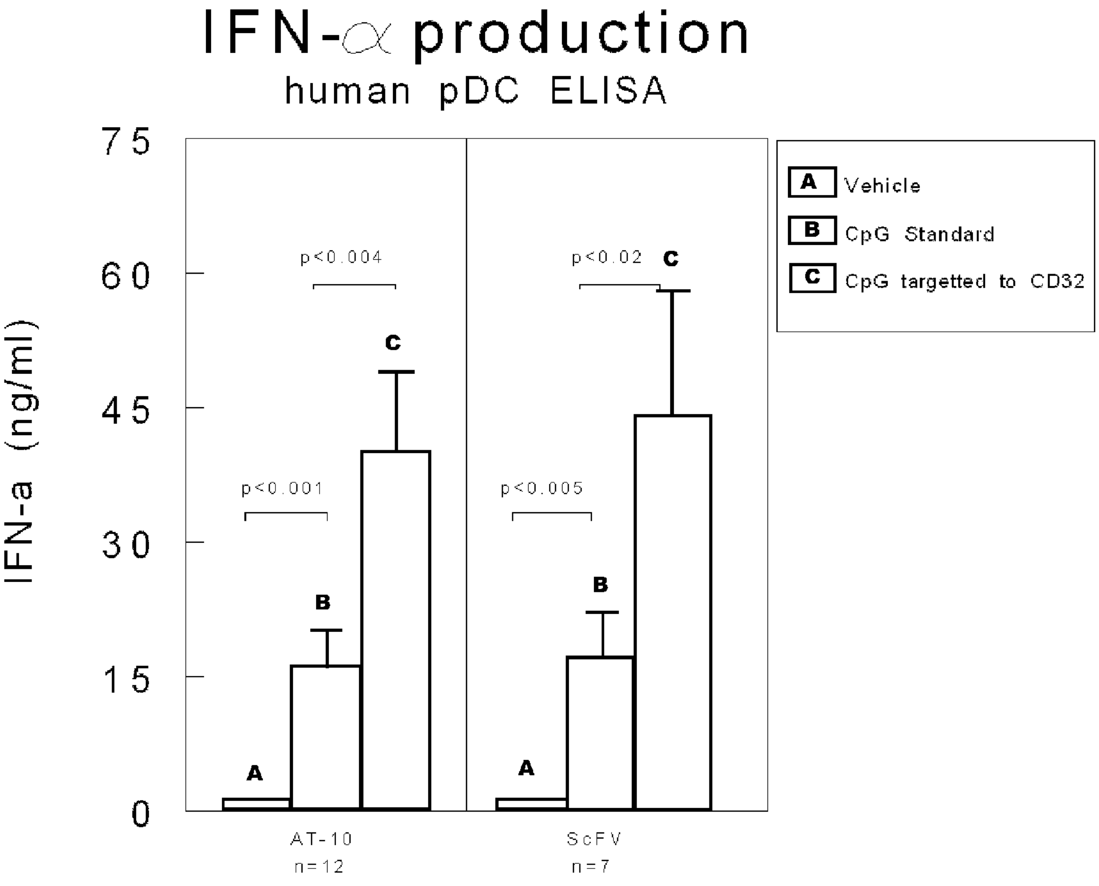
FIG. 3 is another graph showing IFN-α production of human pDCs after stimulation with CPG-C.

IFNα production of pDCS after stimulation with CPG-C: Maximum IFNα production in each experiment was seen when CPG-C-biot was complexed with aCD32biot through streptavidin. Stimulation with CpG without targeting (CpG standard) was significantly less potent than CpG targeted to CD32 ($p<0.04$ resp. $p<0.02$). There is no difference when the aCD32 antibody AT10 (specific for CD32a and CD32b) was used or whether an unrelated single chain antibody (specific for CD32a only) was used. This confirms that the enhancement is independent of the epitope that is recognized on CD32 and independent of the type of binder that is used. Statistical analyses was done with the paired student t-test; $p<0.05$ were considered significant (see FIG. 3).

Example 10: Effect of a Molecule Complex Comprising Different Formats of Anti-CD32 And TLR9 Binding Moieties on the Immune Response as Determined on Plasmacytoid Dendritic (pDCs) Cells Stimulation of pDCs with CpG Targeted to CD32, Employing an aCD32 Peptide, Read Out IL-6 and TNFα Production 10.1 Material and Methods a) PBMC Cells:

Buffy coats were obtained from the Red Cross Austria. Cells were separated on ficoll hypack.

b) Stimulation of pDCs:

Freshly isolated PBMC's were incubated with 200 μg/ml aCD32a peptide published by Berntzen et al (J. Biol. Chem. (2009) 284:1126-1135; sequence ADGAWAWVWLTETAVGAAK-biotin, SEQ ID NO:68) in PBA (PBS containing 5% BSA) on ice for 30 minutes and washed twice with PBA, followed by an incubation with 10 μg/ml streptavidin in PBA on ice for 30 minutes and two times washing with PBA. Subsequently, PBMC's were incubated on ice for 15 minutes with either PBA, 5 μg/ml ODN-CpG C (M362, Axorra) in PBA or 5 μg/ml ODN-CpG C-3'-biotin in PBA (M362, Girindus). Unbound ODN-CpG C was washed away three time with PBA and PBMCs were cultured overnight (37° C., 5% CO2) in X-VIVO-15 medium (Cambrex), supplemented with 2% of decomplemented human AB+ serum. Supernatants were collected from PBMC cultures after overnight stimulation, and $IFN^L$ production was analyzed with murine monoclonal capture and HRP-conjugated anti-IL-6 or $TNF^L$ antibodies (BenderMed systems) using standard ELISA procedures.

10.2. Results

Figure 4:
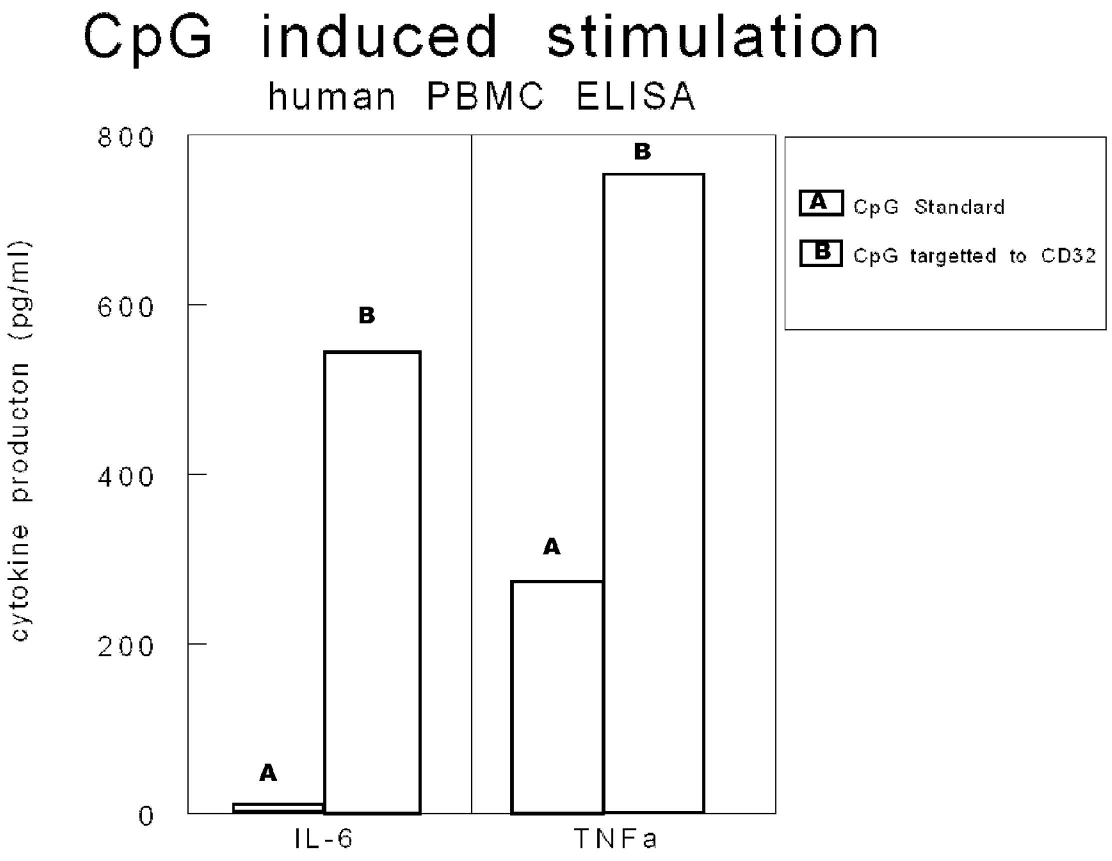
FIG. 4 is a graph showing IL-6 and TNFα production of pDCS after stimulation with CPG-C.

IL-6 production of pDCS in PBMC after stimulation with CPG-C: Maximum IL-6 production was seen when CPG-C-biot was complexed with aCD32biot through streptavidin. Stimulation with CpG without targeting (CpG standard) was ~75 times less potent than CpG targeted to CD32. Whereas for TNFα the induction was ~3 times stronger when CpG was targeted to CD32. This confirms that the enhancement is independent of the epitope that is recognized on CD32 and independent of the type of binder that is used. Statistical analyses was done with the paired student t-test; $p<0.05$ were considered significant (see FIG. 4).

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references cited herein are incorporated by reference in their entirety.

REFERENCES

1. Mudde. G. C, I. G. Reischl, N. Corvaïa, A. Hren, and E.-M. Pollabauer. 1996. Antigen presentation in allergic sensitization. Immunol. Cell Biol. 74:167-173.
2. Bheekha Escura. R., E. Wasserbauer, F. Hammerschmid, A. Pearce, P. Kidd, and G. C. Mudde. 1995. Regulation and targeting of T-cell immune responses by IgE and IgG antibodies. Immunology 86:343-350.
3. Pene. J., F. Rousset, F. Briere, I. Chretien, J.-Y. Bonnefoy, H. Spits, T. Yokota, K.-I. Arai, J. Banchereau, and J. E. De Vries. 1988. IgE production by normal human lymphocytes is induced by interleukin 4 and suppressed by interferons gamma and alpha and prostaglandin E2. Proc. Natl. Acad. ScL USA 85:6880-6884.
4. Ebner. C. 1999. Immunological mechanisms operative in allergen-specific immunotherapy. IntArch Allergy Immunol 119:1-5.
5. Ferreira. F., C. Ebner, B. Kramer, G. Casari, P. Briza, A. J. Kungl, R. Grimm, B. Jahn-Schmid, H. Breiteneder, D. Kraft, M. Breitenbach, H. J. Rheinberger, and O. Scheiner. 1998. Modulation of IgE reactivity of allergens by site-directed mutagenesis: potential use of hypoallergenic variants for immunotherapy. FASEB Journal 12:231-242.
6. Rissoan. M. C, V. Soumelis, N. Kadowaki, G. Grouard, F. Briere, R. D. Malefyt, and Y. J. Liu. 1999. Reciprocal control of T helper cell and dendritic cell differentiation. Science 283:1183-1186.
7. Kapsenberg. M. L, C. M. Hilkens, E. A. Wierenga, and P. Kalinski. 1999. The paradigm of type 1 and type 2 antigen-presenting cells. Implications for atopic allergy. Clin. Exp. Allergy 29:33-36.
8. Charbonnier. A. S., H. Hammad, P. Gosset, G. A. Stewart, S. Alkan, A. B. Tonnel, and J. Pestel. 2003. Der p1-pulsed myeloid and plasmacytoid dendritic cells from house dust mite-sensitized allergic patients dysregulate the T cell response. J. Leukocyte Biol. 73:91-99.
9. Rothenfusser. S., E. Tuma, S. Endres, and G. Hartmann. 2002. Plasmacytoid dendritic cells: The key to CpG. Hum. Immunol. 63:1111-1119.
10. Latz. E., A. Schoenemeyer, A. Visintin, K. A. Fitzgerald, B. G. Monks, C. F. Knetter, E. Lien, N. J. Nilsen, T. Espevik, and D. T. Golenbock. 2004. TLR9 signals after translocating from the ER to CpG DNA in the lysosome. Nat. Immunol. 5:190-198.
11. Leifer. C A, M. N. Kennedy, A. Mazzoni, C. W. Lee, M. J. Kruhlak, and D. A. Segal. 2004. TLR9 Is localized in the endoplasmic reticulum prior to stimulation. J. Immunol. 173:1179-1183.
12. Wang. W. W., D. Das, X. L. Tang, W. Budzynski, and M. R. Suresh. 2005. Antigen targeting to dendritic cells with bispecific antibodies. J. Immunol. Methods.
13. van Schaijk. F. G., E. Oosterwijk, A. C. Soede, M. Broekema, C. Frielink, W. J. McBride, D. M. Goldenberg, F. H. Corstens, and O. C. Boerman. 2005. Pretargeting of carcinoembryonic antigen-expressing tumors with a biologically produced bispecific anticarcinoembryonic antigen x anti-indium-labeled diethylenetriaminepentaacetic acid antibody. CHn. Cancer Res. 11:7130s-7136s.
14. Le. G. F., U. Reusch, G. Moldenhauer, M.ϋttle, and S. M. Kipriyanov. 2004. Immunosuppressive properties of anti-CD3 single-chain Fv and diabody. J. Immunol. Methods 285:111-127.
15. Schuster, M., P. Umana, C. Ferrara, P. Brunker, C. Gerdes, G. Waxenecker, S. Wiederkum, C. Schwager, H. Loibner, G. Himmler, and G. C. Mudde. 2005. Improved effector functions of a therapeutic monoclonal Lewis Y-specific antibody by glycoform engineering. Cancer Res 65:7934-7941.

16. Orlandi. R., D. H. Gussow, P. T. Jones, and G. Winter. 1989. Cloning immunoglobulin variable domains for expression by the polymerase chain reaction. Proc. Natl. Acad. Sci. U.S.A. 86:3833-3837.

17. Barton. G. M., J. C. Kagan, and R. Medzhitov. 2005. Intracellular localization of Toll-like receptor 9 prevents recognition of self DNA but facilitates access to viral DNA. Nat. Immunol.

18. Chen. W. L, J. L. Wang, H. Z. An, J. Zhou, L. H. Zhang, and X. T. Cao. 2005. Heat shock up-regulates TLR9 expression in human B cells through activation of ERK and NF-kappaB signal pathways. Immunol. Lett. 98:153-159.

19. Eaton-Bassiri. A., S. B. Dillon, M. Cunningham, M. A. Rycyzyn, J. Mills, R. T. Sarisky, and M. L. Mbow. 2004. Toll-like receptor 9 can be expressed at the cell surface of distinct populations of tonsils and human peripheral blood mononuclear cells. Infect. Immun. 72:7202-7211.

20. Leroy. B. P., J.-M. Lachapelle, M. Jacquemin, and J.-M. Saint-Remy. 1992. Treatment of atopic dermatitis by allergen-antibody complexes: Long-term clinical results and evolution of IgE antibodies. Dermatologica 184:271-274.

21. Chua. K. Y., W. K. Greene, P. Kehal, and W. R. Thomas. 1991. IgE binding studies with large peptides expressed from Der p Il cDNA constructs. CHn. Exp. Allergy. 21:161-166.

22. Baselmans. P. J., E. Pollabauer, F. C. Van Reijsen, H. C. Heystek, A. Hren, P. Stumptner, M. G. Tilanus, W. C. Vooijs, and G. C. Mudde. 2000. IgE production after antigen-specific and cognate activation of HLA-DPw4-restricted T-cell clones, by 78% of randomly selected B-cell donors. Hum. Immunol. 61:789-798.

23. Beck. H., G. Schwarz, C. J. Schroter, M. Deeg, D. Baier, S. Stevanovic, E. Weber, C. Driessen, and H. Kalbacher. 2001. Cathepsin S and an asparagine-specific endoprotease dominate the proteolytic processing of human myelin basic protein in vitro. Eur J Immunol 31:3726-3736.

24. Higgins. J. A., C. J. Thorpe, J. D. Hayball, R. E. OHehir, and J. R. Lamb. 1994. Overlapping T-cell epitopes in the group I allergen of *Dermatophagoides* species restricted by HLA-DP and HLA-DR class Il molecules. J. Allergy CHn. Immunol. 93:891-899.

25. Bian. H., J. F. Reidhaar-Olson, and J. Hammer. 2003. The use of bioinformatics for identifying class ll-restricted T-cell epitopes. Methods 29:299-309.

26. Sturniolo. T., E. Bono, J. Ding, L. Raddhzzani, O. Tuereci, U. Sahin, M. Braxenthaler, F. Gallazzi, M. P. Protti, F. Sinigaglia, and J. Hammer. 1999. Generation of tissue-specific and promiscuous HLA ligand databases using DNA microarrays and virtual HLA class Il matrices. Nat. Biotechnol. 17:555-561.

The invention claimed is:

1. A composition which comprises a molecule or molecule complex comprising a TLR9 binding part capable of binding to TLR9, a CD32 binding part capable of binding to CD32, and at least one antigen, wherein the CD32 binding part is selected from the group consisting of antibodies and CD32-binding antibody fragments, and wherein the TLR9 binding part is a CpG oligodeoxynucleotide.

2. The composition of claim 1, characterized in that the antigen is an allergen or part of an allergen.

3. The composition of claim 1, characterized in that the antigen is non-covalently linked to the molecule or molecule complex.

4. The composition of claim 1, characterized in that the antigen is non-covalently linked to the TLR9 binding part or the CD32 binding part.

5. The composition of claim 2, characterized in that the allergen is selected from the group consisting of an allergen associated with atopic dermatitis, an allergen associated with allergic asthma, an allergen associated with allergic rhinitis or an allergen associated with allergic conjunctivitis.

6. The composition of claim 1, characterized in that the antigen is selected from the group consisting of a denatured antigen and an antigen modified to prevent binding to IgE.

7. The composition of claim 1, wherein the CD32-binding antibody fragment is an scFv of an antibody.

8. The composition of claim 1, characterized in that the antibody is selected from the group consisting of IgG, IgM, IgE, IgA and IgD.

9. The composition of claim 1, wherein the antibody is selected from the group consisting of a human antibody and a humanized antibody.

10. The composition of claim 1, characterized in that at least part of the antibody is derived from a mammal selected from the group consisting of a human, a mouse, and a camel.

11. The composition of claim 1, further comprising at least one pharmaceutically acceptable carrier or diluent.

12. The composition of claim 1, wherein the TLR9 binding part is any of CpG-A, CpG-B or CpG-C ligands.

13. The composition of claim 1, wherein the antigen comprises one or more T cell epitopes of house dust mite allergens.

14. The composition of claim 13, wherein the antigen is selected from the group consisting of Immunogen 3 comprising the sequence of positions 7-208 of SEQ ID NO:97 and Immunogen 5-12 comprising the sequence of positions 1-364 of SEQ ID NO:98.

15. The composition of claim 1, wherein the antigen is a tumor associated antigen.

* * * * *

SEQUENCE LISTING

```
<160> NUMBER OF SEQ ID NOS: 105

<210> SEQ ID NO 1
<211> LENGTH: 14
<212> TYPE: PRT
<213> ORGANISM: Homo sapiens

<400> SEQUENCE: 1

Cys Pro Arg His Phe Pro Gln Leu His Pro Asp Thr Phe Ser
1               5                   10


<210> SEQ ID NO 2
<211> LENGTH: 16
<212> TYPE: PRT
<213> ORGANISM: Homo sapiens

<400> SEQUENCE: 2

Leu Thr His Leu Ser Leu Lys Tyr Asn Asn Leu Thr Val Val Pro Arg
1               5                   10                  15


<210> SEQ ID NO 3
<211> LENGTH: 25
<212> TYPE: PRT
<213> ORGANISM: Homo sapiens

<400> SEQUENCE: 3

Ala Asn Leu Thr Ala Leu Arg Val Leu Asp Val Gly Gly Asn Cys Arg
1               5                   10                  15

Arg Cys Asp His Ala Pro Asn Pro Cys
            20                  25


<210> SEQ ID NO 4
<211> LENGTH: 43
<212> TYPE: PRT
```

<213> ORGANISM: Dermatophagoides pteronyssinus

<400> SEQUENCE: 4

```
Gln Ser Cys Arg Arg Pro Asn Ala Gln Arg Phe Gly Ile Ser Asn Tyr
1               5                   10                  15

Cys Gln Ile Tyr Pro Pro Asn Ala Asn Lys Ile Arg Glu Ala Leu Ala
            20                  25                  30

Gln Pro Gln Arg Tyr Cys Arg His Tyr Trp Thr
        35                  40
```

<210> SEQ ID NO 5
<211> LENGTH: 31
<212> TYPE: PRT
<213> ORGANISM: Dermatophagoides pteronyssinus

<400> SEQUENCE: 5

```
Gln Ser Cys Arg Arg Pro Asn Ala Gln Arg Phe Gly Ile Ser Asn Tyr
1               5                   10                  15

Cys Gln Ile Tyr Pro Pro Asn Ala Asn Lys Ile Arg Glu Ala Leu
            20                  25                  30
```

<210> SEQ ID NO 6
<211> LENGTH: 13
<212> TYPE: PRT
<213> ORGANISM: Dermatophagoides pteronyssinus

<400> SEQUENCE: 6

```
Asn Ala Gln Arg Phe Gly Ile Ser Asn Tyr Cys Gln Ile
1               5                   10
```

<210> SEQ ID NO 7
<211> LENGTH: 25
<212> TYPE: PRT
<213> ORGANISM: Dermatophagoides pteronyssinus

<400> SEQUENCE: 7

```
Arg Thr Val Thr Pro Ile Arg Met Gln Gly Gly Cys Gly Ser Cys Trp
1               5                   10                  15

Ala Phe Ser Gly Val Ala Ala Thr Glu
            20                  25
```

<210> SEQ ID NO 8
<211> LENGTH: 25
<212> TYPE: PRT
<213> ORGANISM: Dermatophagoides pteronyssinus

<400> SEQUENCE: 8

```
Tyr Asp Gly Arg Thr Ile Ile Gln Arg Asp Asn Gly Tyr Gln Pro Asn
1               5                   10                  15

Tyr His Ala Val Asn Ile Val Gly Tyr
            20                  25
```

<210> SEQ ID NO 9
<211> LENGTH: 19
<212> TYPE: PRT
<213> ORGANISM: Dermatophagoides pteronyssinus

<400> SEQUENCE: 9

```
Pro Cys Ile Ile His Arg Gly Lys Pro Phe Gln Leu Glu Ala Val Phe
1               5                   10                  15

Glu Ala Asn
```

<210> SEQ ID NO 10
<211> LENGTH: 19
<212> TYPE: PRT
<213> ORGANISM: Dermatophagoides pteronyssinus

<400> SEQUENCE: 10

Lys Tyr Thr Trp Asn Val Pro Lys Ile Ala Pro Lys Ser Glu Asn Val
1               5                   10                  15

Val Val Thr

<210> SEQ ID NO 11
<211> LENGTH: 22
<212> TYPE: PRT
<213> ORGANISM: Dermatophagoides pteronyssinus

<400> SEQUENCE: 11

Glu Asn Val Val Val Thr Val Lys Val Met Gly Asp Asp Gly Val Leu
1               5                   10                  15

Ala Cys Ala Ile Ala Thr
            20

<210> SEQ ID NO 12
<211> LENGTH: 22
<212> TYPE: PRT
<213> ORGANISM: Dermatophagoides pteronyssinus

<400> SEQUENCE: 12

Gln Ser Cys Arg Arg Pro Asn Ala Gln Arg Phe Gly Ile Ser Asn Tyr
1               5                   10                  15

Cys Gln Ile Tyr Pro Pro
            20

<210> SEQ ID NO 13
<211> LENGTH: 15
<212> TYPE: PRT
<213> ORGANISM: Dermatophagoides pteronyssinus

<400> SEQUENCE: 13

Cys Gln Ile Tyr Pro Pro Asn Ala Asn Lys Ile Arg Glu Ala Leu
1               5                   10                  15

<210> SEQ ID NO 14
<211> LENGTH: 17
<212> TYPE: PRT
<213> ORGANISM: Dermatophagoides pteronyssinus

<400> SEQUENCE: 14

Ile Arg Glu Ala Leu Ala Gln Pro Gln Arg Tyr Cys Arg His Tyr Trp
1               5                   10                  15

Thr

<210> SEQ ID NO 15
<211> LENGTH: 36
<212> TYPE: DNA
<213> ORGANISM: Homo sapiens

<400> SEQUENCE: 15
aaacgggcag atgctgcacc aactgtatcc atcttc                              36

<210> SEQ ID NO 16
<211> LENGTH: 164
<212> TYPE: PRT

<213> ORGANISM: Homo sapiens

<400> SEQUENCE: 16

```
Cys Gln Ile Tyr Pro Pro Asn Ala Asn Lys Ile Arg Glu Ala Leu Gln
1               5                   10                  15

Ser Cys Arg Arg Pro Asn Ala Gln Arg Phe Gly Ile Ser Asn Tyr Cys
            20                  25                  30

Gln Ile Tyr Pro Pro Tyr Asp Gly Arg Thr Ile Ile Gln Arg Asp Asn
        35                  40                  45

Gly Tyr Gln Pro Asn Tyr His Ala Val Asn Ile Val Gly Tyr Glu Asn
    50                  55                  60

Val Val Val Thr Val Lys Val Met Gly Asp Asp Gly Val Leu Ala Cys
65                  70                  75                  80

Ala Ile Ala Thr Lys Tyr Thr Trp Asn Val Pro Lys Ile Ala Pro Lys
                85                  90                  95

Ser Glu Asn Val Val Val Thr Ile Arg Glu Ala Leu Ala Gln Pro Gln
            100                 105                 110

Arg Tyr Cys Arg His Tyr Trp Thr Pro Cys Ile Ile His Arg Gly Lys
        115                 120                 125

Pro Phe Gln Leu Glu Ala Val Phe Glu Ala Asn Arg Thr Val Thr Pro
    130                 135                 140

Ile Arg Met Gln Gly Gly Cys Gly Ser Cys Trp Ala Phe Ser Gly Val
145                 150                 155                 160

Ala Ala Thr Glu
```

<210> SEQ ID NO 17
<211> LENGTH: 28
<212> TYPE: DNA
<213> ORGANISM: artificial sequence
<220> FEATURE:
<223> OTHER INFORMATION: oligonucleotide for generation of synthetic gene coding for the allergen epitope

<400> SEQUENCE: 17
tccggatgcc aaatttaccc gccaaacg 28

<210> SEQ ID NO 18
<211> LENGTH: 40
<212> TYPE: DNA
<213> ORGANISM: artificial sequence
<220> FEATURE:
<223> OTHER INFORMATION: oligonculeotide for generation of synthetic gene coding for allergen epitope

<400> SEQUENCE: 18
agcctctctg atcttgttcg cgtttggcgg gtaaatttgg 40

<210> SEQ ID NO 19
<211> LENGTH: 40
<212> TYPE: DNA
<213> ORGANISM: artificial sequence
<220> FEATURE:
<223> OTHER INFORMATION: oligonucleotide for generation of synthetic gene coding for allergen epitope

<400> SEQUENCE: 19
cgaacaagat cagagaggct ttgcaatctt gcaggaggcc 40

<210> SEQ ID NO 20
<211> LENGTH: 40
<212> TYPE: DNA

<213> ORGANISM: artificial sequence
<220> FEATURE:
<223> OTHER INFORMATION: oligonucleotide for generation of synthetic
gene coding for allergen epitope

<400> SEQUENCE: 20
tatgccgaat ctctgcgcat tgggcctcct gcaagattgc 40

<210> SEQ ID NO 21
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 21
gcgcagagat tcggcatatc caactactgc cagatctacc 40

<210> SEQ ID NO 22
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 22
gtacgcccat cgtatggggg gtagatctgg cagtagttgg 40

<210> SEQ ID NO 23
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 23
cccatacgat gggcgtacaa tcatacagcg tgataacggc 40

<210> SEQ ID NO 24
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 24
gcgtggtagt taggctgata gccgttatca cgctgtatga 40

<210> SEQ ID NO 25
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 25
tatcagccta actaccacgc cgtgaacatc gtcggctacg 40

<210> SEQ ID NO 26
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 26
tcacagtaac cacgacattc tcgtagccga cgatgttcac 40

<210> SEQ ID NO 27
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 27
agaatgtcgt ggttactgtg aaggtaatgg gcgatgacgg 40

<210> SEQ ID NO 28
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 28
agctatggcg caagctagaa ccccgtcatc gcccattacc 40

<210> SEQ ID NO 29
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 29
tctagcttgc gccatagcta ccaagtacac ttggaacgta 40

<210> SEQ ID NO 30
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 30
ttttcggcgc aattttgggt acgttccaag tgtacttggt 40

<210> SEQ ID NO 31
<211> LENGTH: 40
<212> TYPE: DNA
<213> ORGANISM: artificial sequence
<220> FEATURE:
<223> OTHER INFORMATION: oligonucleotide for generation of synthetic
gene coding for allergen epitope

<400> SEQUENCE: 31
cccaaaattg cgccgaaaag tgaaaacgtc gtagtgacca 40

<210> SEQ ID NO 32
<211> LENGTH: 40
<212> TYPE: DNA
<213> ORGANISM: artificial sequence
<220> FEATURE:

<223> OTHER INFORMATION: oligonucleotide for generation of synthetic
      gene coding for allergen epitope

<400> SEQUENCE: 32
tgagccaatg cctcccttat ggtcactacg acgttttcac 40

<210> SEQ ID NO 33
<211> LENGTH: 40
<212> TYPE: DNA
<213> ORGANISM: artificial sequence
<220> FEATURE:
<223> OTHER INFORMATION: oligonucleotide for generation of synthetic
      gene coding for allergen epitope

<400> SEQUENCE: 33
agggaggcat tggctcaacc tcaaagatac tgcagacact 40

<210> SEQ ID NO 34
<211> LENGTH: 40
<212> TYPE: DNA
<213> ORGANISM: artificial sequence
<220> FEATURE:
<223> OTHER INFORMATION: oligonucleotide for generation of synthetic
      gene coding for allergen epitope

<400> SEQUENCE: 34
ttatgcaggg cgtccagtag tgtctgcagt atctttgagg 40

<210> SEQ ID NO 35
<211> LENGTH: 40
<212> TYPE: DNA
<213> ORGANISM: artificial sequence
<220> FEATURE:
<223> OTHER INFORMATION: oligonucleotide for generation of synthetic
      gene coding for allergen epitope

<400> SEQUENCE: 35
actggacgcc ctgcataatc caccgtggta aaccctttca 40

<210> SEQ ID NO 36
<211> LENGTH: 40
<212> TYPE: DNA
<213> ORGANISM: artificial sequence
<220> FEATURE:
<223> OTHER INFORMATION: oligonucleotide for generation of synthetic
      gene coding for allergen epitope

<400> SEQUENCE: 36
cttcgaacac tgcctcaagt tgaaagggtt taccacggtg 40

<210> SEQ ID NO 37
<211> LENGTH: 40
<212> TYPE: DNA
<213> ORGANISM: artificial sequence
<220> FEATURE:
<223> OTHER INFORMATION: oligonucleotide for generation of synthetic
      gene coding for allergen epitope

<400> SEQUENCE: 37
acttgaggca gtgttcgaag ctaacaggac ggtaacgcca 40

<210> SEQ ID NO 38
<211> LENGTH: 40
<212> TYPE: DNA
<213> ORGANISM: artificial sequence
<220> FEATURE:
<223> OTHER INFORMATION: oligonucleotide for generation of synthetic gene coding for allergen epitope

<400> SEQUENCE: 38
ccgcacccac cttgcatacg aattggcgtt accgtcctgt 40

<210> SEQ ID NO 39
<211> LENGTH: 40
<212> TYPE: DNA
<213> ORGANISM: artificial sequence
<220> FEATURE:
<223> OTHER INFORMATION: oligonucleotide for generation of synthetic gene coding for allergen epitope

<400> SEQUENCE: 39
tgcaaggtgg gtgcgggtct tgttgggctt tttctggtgt 40

<210> SEQ ID NO 40
<211> LENGTH: 42
<212> TYPE: DNA
<213> ORGANISM: artificial sequence
<220> FEATURE:
<223> OTHER INFORMATION: oligonucleotide for generation of synthetic gene coding for allergen epitope

<400> SEQUENCE: 40
actagtttat tcagtagcag ccacaccaga aaaagcccaa ca 42

<210> SEQ ID NO 41
<211> LENGTH: 6
<212> TYPE: PRT
<213> ORGANISM: Homo sapiens

<400> SEQUENCE: 41

Lys Arg Ala Pro Arg Glu
1 5

<210> SEQ ID NO 42
<211> LENGTH: 18
<212> TYPE: DNA
<213> ORGANISM: artificial sequence
<220> FEATURE:
<223> OTHER INFORMATION: silent mutation to introduce unique XhoI site

<400> SEQUENCE: 42
aaacgggctc ctcgagaa 18

<210> SEQ ID NO 43
<211> LENGTH: 219
<212> TYPE: PRT
<213> ORGANISM: artificial sequence
<220> FEATURE:
<223> OTHER INFORMATION: complete sequence of a VL-CH3 fusion protein

<400> SEQUENCE: 43

Asp Ile Val Met Thr Gln Ala Ala Pro Ser Val Pro Val Thr Pro Gly
1 5 10 15

Glu Ser Val Ser Ile Ser Cys Arg Ser Ser Lys Ser Leu Leu His Thr
20 25 30

Asn Gly Asn Thr Tyr Leu His Trp Phe Leu Gln Arg Pro Gly Gln Ser
35 40 45

Pro Gln Leu Leu Ile Tyr Arg Met Ser Val Leu Ala Ser Gly Val Pro
50 55 60

Asp Arg Phe Ser Gly Ser Gly Ser Gly Thr Ala Phe Thr Leu Ser Ile
65 70 75 80

Ser Arg Val Glu Ala Glu Asp Val Gly Val Phe Tyr Cys Met Gln His
85 90 95

Leu Glu Tyr Pro Leu Thr Phe Gly Ala Gly Thr Lys Leu Glu Leu Lys
100 105 110

Arg Ala Pro Arg Glu Pro Gln Val Tyr Thr Leu Pro Pro Ser Arg Asp
115 120 125

Glu Leu Gly Ile Ala Gln Val Ser Leu Thr Cys Leu Val Lys Gly Phe
130 135 140

Tyr Pro Ser Asp Ile Ala Val Glu Trp Glu Ser Asn Gly Gln Pro Glu
145 150 155 160

Asn Asn Tyr Lys Thr Thr Pro Pro Val Leu Asp Ser Asp Gly Ser Phe
165 170 175

Phe Leu Tyr Ser Lys Leu Thr Val Leu Gly Arg Arg Trp Thr Leu Gly
180 185 190

Asn Val Phe Ser Cys Ser Val Met His Glu Ala Leu His Asn His Tyr
195 200 205

Thr Gln Lys Ser Leu Ser Leu Ser Pro Gly Lys
210 215

<210> SEQ ID NO 44
<211> LENGTH: 681
<212> TYPE: DNA
<213> ORGANISM: artificial sequence
<220> FEATURE:
<223> OTHER INFORMATION: nucleic acid sequence of VL-CH3 fusion protein

<400> SEQUENCE: 44
gaattcgaca ttgtgatgac ccaggctgca ccctctgtac ctgtcactcc tggagagtca 60
gtatccatct cctgcaggtc tagtaagagt ctcctgcata ctaatggcaa cacttacttg 120
cattggttcc tacagaggcc aggccagtct cctcagctcc tgatatatcg gatgtccgtc 180
cttgcctcag gagtcccaga caggttcagt ggcagtgggt caggaactgc tttcacactg 240
agcatcagta gagtggaggc tgaggatgtg ggtgtttttt actgtatgca acatctagaa 300
tatccgctca cgttcggtgc tgggaccaag ctggaactga aacgggctcc tcgagaacca 360
caggtgtaca ccctgccccc atcccgggac gagctcggca tcgcgcaagt cagcctgacc 420
tgcctggtca aaggcttcta tcccagcgac atcgccgtgg agtgggagag caacgggcag 480
ccggagaaca actacaagac cacgcctccc gtgctggact ccgacggctc tttcttcctc 540
tacagcaagc ttaccgtgtt gggccgcagg tggaccctgg ggaacgtctt ctcatgctcc 600
gtgatgcatg aggctctgca caaccactac acacagaaga gcctctccct gtctccgggt 660
aaatgagggc gcgccggtac c 681

<210> SEQ ID NO 45
<211> LENGTH: 6
<212> TYPE: PRT
<213> ORGANISM: artificial sequence
<220> FEATURE:
<223> OTHER INFORMATION: part of heavy chain of CH3 domain

<400> SEQUENCE: 45

Ala Lys Thr Arg Glu Pro
1 5

<210> SEQ ID NO 46
<211> LENGTH: 18
<212> TYPE: DNA

<213> ORGANISM: artificial sequence
<220> FEATURE:
<223> OTHER INFORMATION: VH-CH3 with silent mutation to introduce XhoI site

<400> SEQUENCE: 46
gccaaaactc gagaacca 18

<210> SEQ ID NO 47
<211> LENGTH: 250
<212> TYPE: PRT
<213> ORGANISM: artificial sequence
<220> FEATURE:
<223> OTHER INFORMATION: complete sequence of VH-CH3 fusion protein

<400> SEQUENCE: 47

```
Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Ala Lys Thr Arg Glu Pro Gln Val
        115                 120                 125

Tyr Thr Leu Pro Pro Ser Arg Asp Glu Leu Gly Ile Ala Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Leu Gly Arg Arg Trp Thr Leu Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ser Leu Glu Gln Lys Leu Ile Ser Glu Glu Asp Leu Asn
225                 230                 235                 240

Ser Ala Val Asp His His His His His His
                245                 250
```

<210> SEQ ID NO 48
<211> LENGTH: 759
<212> TYPE: DNA
<213> ORGANISM: artificial sequence
<220> FEATURE:
<223> OTHER INFORMATION: nucleic acid sequence of VH-CH3 complete fusion protein

<400> SEQUENCE: 48
gaattcgagg ttcagcttca gcagtctgga cctgagctga agaagcctgg agagacagtc 60

```
aagatctcct gcaaggcttc tgggtatacc ttcacaaact atggaatgaa ctgggtgaag    120

caggctccag gaaagggttt aaagtggatg ggctggttaa acacctacac tggagagtca    180

atatatcctg atgacttcaa gggacggttt gccttctctt cggaaacctc tgccagcact    240

gcctatttgc agatcaacaa cctcaaaaat gaggacatgg ctacatattt ctgtgcaaga    300

ggggactatg gttacgacga ccctttggac tactggggtc aaggaacctc agtcaccgtc    360

tcctcagcca aaactcgaga accacaggtg tacaccctgc ccccatcccg ggacgagctc    420

ggcatcgcgc aagtcagcct gacctgcctg gtcaaaggct tctatcccag cgacatcgcc    480

gtggagtggg agagcaacgg gcagccggag aacaactaca agaccacgcc tcccgtgctg    540

gactccgacg gctctttctt cctctacagc aagcttaccg tgttgggccg caggtggacc    600

ctggggaacg tcttctcatg ctccgtgatg catgaggctc tgcacaacca ctacacacag    660

aagagcctct ccctgtctcc gggtaaatct ctagaacaaa aactcatctc agaagaggat    720

ctgaatagcg ccgtcgacca tcatcatcat catcattga                           759
```

<210> SEQ ID NO 49
<211> LENGTH: 30
<212> TYPE: DNA
<213> ORGANISM: artificial sequence
<220> FEATURE:
<223> OTHER INFORMATION: primer 4.3HupEco for PCR amplification

<400> SEQUENCE: 49

```
cagagaattc gaggttcagc ttcagcagtc                                      30
```

<210> SEQ ID NO 50
<211> LENGTH: 30
<212> TYPE: DNA
<213> ORGANISM: artificial sequence
<220> FEATURE:
<223> OTHER INFORMATION: primer 4.3HDOWNXHO for PCR amplification

<400> SEQUENCE: 50

```
gatgctcgag ttttggctga ggagacggtg                                      30
```

<210> SEQ ID NO 51
<211> LENGTH: 32
<212> TYPE: DNA
<213> ORGANISM: artificial sequence
<220> FEATURE:
<223> OTHER INFORMATION: primer CH3UPXHOA for PCR amplification

<400> SEQUENCE: 51

```
aaaactcgag aaccacaggt gtacaccctg cc                                   32
```

<210> SEQ ID NO 52
<211> LENGTH: 34
<212> TYPE: DNA
<213> ORGANISM: artificial sequence
<220> FEATURE:
<223> OTHER INFORMATION: primer CH3XBA2 for PCR amplification

<400> SEQUENCE: 52

```
actgatctag acctttaccc ggagacaggg agag                                 34
```

<210> SEQ ID NO 53
<211> LENGTH: 32
<212> TYPE: DNA
<213> ORGANISM: artificial sequence
<220> FEATURE:

<223> OTHER INFORMATION: primer 4.3LUPECO for PCR amplification

<400> SEQUENCE: 53
gatagaattc gacattgtga tgacccaggc tg 32

<210> SEQ ID NO 54
<211> LENGTH: 31
<212> TYPE: DNA
<213> ORGANISM: artificial sequence
<220> FEATURE:
<223> OTHER INFORMATION: primer 4.3LDOWNXHO for PCR amplification

<400> SEQUENCE: 54
attactcgag gagcccgttt cagttccagc t 31

<210> SEQ ID NO 55
<211> LENGTH: 32
<212> TYPE: DNA
<213> ORGANISM: artificial sequence
<220> FEATURE:
<223> OTHER INFORMATION: primer CH3UPXHOB for PCR amplification

<400> SEQUENCE: 55
gctcctcgag aaccacaggt gtacaccctg cc 32

<210> SEQ ID NO 56
<211> LENGTH: 43
<212> TYPE: DNA
<213> ORGANISM: artificial sequence
<220> FEATURE:
<223> OTHER INFORMATION: primer CH3STOPKPN for PCR amplification

<400> SEQUENCE: 56
acgtggtacc tcaggcgcgc cctttacccg gagacaggga gag 43

<210> SEQ ID NO 57
<211> LENGTH: 32
<212> TYPE: DNA
<213> ORGANISM: artificial sequence
<220> FEATURE:
<223> OTHER INFORMATION: primer EpiTLR1 for PCR amplification

<400> SEQUENCE: 57
taaagggcgc gcctccggat gccaaattta cc 32

<210> SEQ ID NO 58
<211> LENGTH: 35
<212> TYPE: DNA
<213> ORGANISM: artificial sequence
<220> FEATURE:
<223> OTHER INFORMATION: primer EpiTLR2 for PCR amplification

<400> SEQUENCE: 58
tacctcaggc gcgccttatt cagtagcagc cacac 35

<210> SEQ ID NO 59
<211> LENGTH: 114
<212> TYPE: PRT
<213> ORGANISM: artificial sequence
<220> FEATURE:
<223> OTHER INFORMATION: recombinantly produced antibody

<400> SEQUENCE: 59

Asp Ile Val Met Thr Gln Ala Ala Pro Ser Val Pro Val Thr Pro Gly
1 5 10 15

-continued

```
Glu Ser Val Ser Ile Ser Cys Arg Ser Ser Lys Ser Leu Leu His Thr
            20                  25                  30

Asn Gly Asn Thr Tyr Leu His Trp Phe Leu Gln Arg Pro Gly Gln Ser
        35                  40                  45

Pro Gln Leu Leu Ile Tyr Arg Met Ser Val Leu Ala Ser Gly Val Pro
    50                  55                  60

Asp Arg Phe Ser Gly Ser Gly Ser Gly Thr Ala Phe Thr Leu Ser Ile
65                  70                  75                  80

Ser Arg Val Glu Ala Glu Asp Val Gly Val Phe Tyr Cys Met Gln His
                85                  90                  95

Leu Glu Tyr Pro Leu Thr Phe Gly Ala Gly Thr Lys Leu Glu Leu Lys
            100                 105                 110

Arg Ala


<210> SEQ ID NO 60
<211> LENGTH: 342
<212> TYPE: DNA
<213> ORGANISM: artificial sequence
<220> FEATURE:
<223> OTHER INFORMATION: nucleic acid sequence of recombinantly produced
      antibody

<400> SEQUENCE: 60

gacattgtga tgacccaggc tgcaccctct gtacctgtca ctcctggaga gtcagtatcc      60

atctcctgca ggtctagtaa gagtctcctg catactaatg gcaacactta cttgcattgg     120

ttcctacaga ggccaggcca gtctcctcag ctcctgatat atcggatgtc cgtccttgcc     180

tcaggagtcc cagacaggtt cagtggcagt gggtcaggaa ctgctttcac actgagcatc     240

agtagagtgg aggctgagga tgtgggtgtt ttttactgta tgcaacatct agaatatccg     300

ctcacgttcg gtgctgggac caagctggaa ctgaaacggg ct                        342


<210> SEQ ID NO 61
<211> LENGTH: 123
<212> TYPE: PRT
<213> ORGANISM: artificial sequence
<220> FEATURE:
<223> OTHER INFORMATION: recombinantly produce antibody

<400> SEQUENCE: 61

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Ala Lys Thr
        115                 120


<210> SEQ ID NO 62
```

<211> LENGTH: 369
<212> TYPE: DNA
<213> ORGANISM: artificial sequence
<220> FEATURE:
<223> OTHER INFORMATION: nucleic acid sequence of recombinantly produced antibody

<400> SEQUENCE: 62
gaggttcagc ttcagcagtc tggacctgag ctgaagaagc ctggagagac agtcaagatc 60
tcctgcaagg cttctgggta taccttcaca aactatggaa tgaactgggt gaagcaggct 120
ccaggaaagg gtttaaagtg gatgggctgg ttaaacacct acactggaga gtcaatatat 180
cctgatgact tcaagggacg gtttgccttc tcttcggaaa cctctgccag cactgcctat 240
ttgcagatca acaacctcaa aaatgaggac atggctacat atttctgtgc aagaggggac 300
tatggttacg acgacccttt ggactactgg ggtcaaggaa cctcagtcac cgtctcctca 360
gccaaaaca 369

<210> SEQ ID NO 63
<211> LENGTH: 6537
<212> TYPE: DNA
<213> ORGANISM: artificial sequence
<220> FEATURE:
<223> OTHER INFORMATION: final expression vector containing TLR9 and CD32 binding regions

<400> SEQUENCE: 63
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg atgagatttc cttcaatttt 960
tactgctgtt ttattcgcag catcctccgc attagctgct ccagtcaaca ctacaacaga 1020
agatgaaacg gcacaaattc cggctgaagc tgtcatcggt tactcagatt tagaagggga 1080
tttcgatgtt gctgttttgc cattttccaa cagcacaaat aacgggttat tgtttataaa 1140
tactactatt gccagcattg ctgctaaaga agaaggggta tctctcgaga aaagagaggc 1200
tgaagctgaa ttcgaggttc agcttcagca gtctggacct gagctgaaga agcctggaga 1260
gacagtcaag atctcctgca aggcttctgg gtataccttc acaaactatg gaatgaactg 1320
ggtgaagcag gctccaggaa agggtttaaa gtggatgggc tggttaaaca cctacactgg 1380
agagtcaata tatcctgatg acttcaaggg acggtttgcc ttctcttcgg aaacctctgc 1440
cagcactgcc tatttgcaga tcaacaacct caaaaatgag gacatggcta catatttctg 1500
tgcaagaggg gactatggtt acgacgaccc tttggactac tggggtcaag gaacctcagt 1560
caccgtctcc tcagccaaaa ctcgagaacc acaggtgtac accctgcccc catcccggga 1620
tgagctgggc atcgcgcaag tcagcctgac ctgcctggtc aaaggcttct atcccagcga 1680
catcgccgtg gagtgggaga gcaacgggca gccggagaac aactacaaga ccacgcctcc 1740
cgtgctggac tccgacggct ctttcttcct ctacagcaag cttaccgtgt tgggccgcag 1800
gtggaccctg gggaacgtct tctcatgctc cgtgatgcat gaggctctgc acaaccacta 1860
cacgcagaag agcctctccc tgtctccggg taaatctcta gaacaaaaac tcatctcaga 1920
agaggatctg aatagcgccg tcgaccatca tcatcatcat cattgagttt gtagccttag 1980
acatgactgt tcctcagttc aagttgggca cttacgagaa gaccggtctt gctagattct 2040
aatcaagagg atgtcagaat gccatttgcc tgagagatgc aggcttcatt tttgatactt 2100
ttttatttgt aacctatata gtataggatt ttttttgtca ttttgtttct tctcgtacga 2160
gcttgctcct gatcagccta tctcgcagct gatgaatatc ttgtggtagg ggtttgggaa 2220
aatcattcga gtttgatgtt tttcttggta tttcccactc ctcttcagag tacagaagat 2280
taagtgagac cttcgtttgt gcagatccaa catccaaaga cgaaaggttg aatgaaacct 2340
ttttgccatc cgacatccac aggtccattc tcacacataa gtgccaaacg caacaggagg 2400
ggatacacta gcagcagacc gttgcaaacg caggacctcc actcctcttc tcctcaacac 2460
ccacttttgc catcgaaaaa ccagcccagt tattgggctt gattggagct cgctcattcc 2520
aattccttct attaggctac taacaccatg actttattag cctgtctatc ctggcccccc 2580
tggcgaggtt catgtttgtt tatttccgaa tgcaacaagc tccgcattac acccgaacat 2640
cactccagat gagggctttc tgagtgtggg gtcaaatagt ttcatgttcc ccaaatggcc 2700
caaaactgac agtttaaacg ctgtcttgga acctaatatg acaaaagcgt gatctcatcc 2760
aagatgaact aagtttggtt cgttgaaatg ctaacggcca gttggtcaaa aagaaacttc 2820
caaaagtcgg cataccgttt gtcttgtttg gtattgattg acgaatgctc aaaaataatc 2880
tcattaatgc ttagcgcagt ctctctatcg cttctgaacc ccggtgcacc tgtgccgaaa 2940
cgcaaatggg gaaacacccg ctttttggat gattatgcat tgtctccaca ttgtatgctt 3000
ccaagattct ggtgggaata ctgctgatag cctaacgttc atgatcaaaa tttaactgtt 3060
ctaaccccta cttgacagca atatataaac agaaggaagc tgccctgtct taaacctttt 3120
tttttatcat cattattagc ttactttcat aattgcgact ggttccaatt gacaagcttt 3180
tgattttaac gacttttaac gacaacttga gaagatcaaa aaacaactaa ttattcgaaa 3240
cgatgagatt tccttcaatt tttactgctg ttttattcgc agcatcctcc gcattagctg 3300
ctccagtcaa cactacaaca gaagatgaaa cggcacaaat tccggctgaa gctgtcatcg 3360
gttactcaga tttagaaggg gatttcgatg ttgctgtttt gccattttcc aacagcacaa 3420
ataacgggtt attgtttata aatactacta ttgccagcat tgctgctaaa gaagaagggg 3480
tatctctcga gaaaagagag gctgaagctg aattcgacat tgtgatgacc caggctgcac 3540
cctctgtacc tgtcactcct ggagagtcag tatccatctc ctgcaggtct agtaagagtc 3600
tcctgcatac taatggcaac acttacttgc attggttcct acagaggcca ggccagtctc 3660
ctcagctcct gatatatcgg atgtccgtcc ttgcctcagg agtcccagac aggttcagtg 3720
gcagtgggtc aggaactgct ttcacactga gcatcagtag agtggaggct gaggatgtgg 3780
gtgtttttta ctgtatgcaa catctagaat atccgctcac gttcggtgct gggaccaagc 3840
tggaactgaa acgggctcct cgagaaccac aggtgtacac cctgcccccca tcccgggatg 3900 agctgggcat cgcgcaagtc agcctgacct gcctggtcaa aggcttctat cccagcgaca 3960
tcgccgtgga gtgggagagc aacgggcagc cggagaacaa ctacaagacc acgcctcccg 4020
tgctggactc cgacggctct ttcttcctct acagcaagct taccgtgttg ggccgcaggt 4080
ggaccctggg gaacgtcttc tcatgctccg tgatgcatga ggctctgcac aaccactaca 4140
cgcagaagag cctctccctg tctccgggta aagggcgcgc ctgaggtacc tcgagccgcg 4200
gcggccgcca gctttctaga acaaaaactc atctcagaag aggatctgaa tagcgccgtc 4260
gaccatcatc atcatcatca ttgagtttgt agccttagac atgactgttc ctcagttcaa 4320
gttgggcact tacgagaaga ccggtcttgc tagattctaa tcaagaggat gtcagaatgc 4380
catttgcctg agagatgcag gcttcatttt tgatactttt ttatttgtaa cctatatagt 4440
ataggatttt ttttgtcatt ttgtttcttc tcgtacgagc ttgctcctga tcagcctatc 4500
tcgcagctga tgaatatctt gtggtagggg tttgggaaaa tcattcgagt ttgatgtttt 4560
tcttggtatt tcccactcct cttcagagta cagaagatta agtgagacct tcgtttgtgc 4620
ggatccccca cacaccatag cttcaaaatg tttctactcc tttttttactc ttccagattt 4680 tctcggactc cgcgcatcgc cgtaccactt caaaacaccc aagcacagca tactaaattt 4740
tccctctttc ttcctctagg gtgtcgttaa ttacccgtac taaaggtttg gaaaagaaaa 4800
aagagaccgc ctcgtttctt tttcttcgtc gaaaaaggca ataaaaattt ttatcacgtt 4860
tctttttctt gaaatttttt tttttagttt ttttctcttt cagtgacctc cattgatatt 4920
taagttaata aacggtcttc aatttctcaa gtttcagttt catttttctt gttctattac 4980
aacttttttt acttcttgtt cattagaaag aaagcatagc aatctaatct aaggggcggt 5040
gttgacaatt aatcatcggc atagtatatc ggcatagtat aatacgacaa ggtgaggaac 5100
taaaccatgg ccaagttgac cagtgccgtt ccggtgctca ccgcgcgcga cgtcgccgga 5160
gcggtcgagt tctggaccga ccggctcggg ttctcccggg acttcgtgga ggacgacttc 5220
gccggtgtgg tccgggacga cgtgaccctg ttcatcagcg cggtccagga ccaggtggtg 5280
ccggacaaca ccctggcctg ggtgtgggtg cgcggcctgg acgagctgta cgccgagtgg 5340
tcggaggtcg tgtccacgaa cttccgggac gcctccgggc cggccatgac cgagatcggc 5400
gagcagccgt gggggcggga gttcgccctg cgcgacccgg ccggcaactg cgtgcacttc 5460
gtggccgagg agcaggactg acacgtccga cggcggccca cgggtcccag gcctcggaga 5520
tccgtccccc ttttcctttg tcgatatcat gtaattagtt atgtcacgct tacattcacg 5580
ccctcccccc acatccgctc taaccgaaaa ggaaggagtt agacaacctg aagtctaggt 5640
ccctatttat ttttttatag ttatgttagt attaagaacg ttatttatat ttcaaatttt 5700
tctttttttt ctgtacagac gcgtgtacgc atgtaacatt atactgaaaa ccttgcttga 5760
gaaggttttg ggacgctcga aggctttaat ttgcaagctg gagaccaaca tgtgagcaaa 5820
aggccagcaa aaggccagga accgtaaaaa ggccgcgttg ctggcgtttt tccataggct 5880
ccgcccccct gacgagcatc acaaaaatcg acgctcaagt cagaggtggc gaaacccgac 5940
aggactataa agataccagg cgtttccccc tggaagctcc ctcgtgcgct ctcctgttcc 6000
gaccctgccg cttaccggat acctgtccgc ctttctccct tcgggaagcg tggcgctttc 6060
tcaatgctca cgctgtaggt atctcagttc ggtgtaggtc gttcgctcca agctgggctg 6120
tgtgcacgaa ccccccgttc agcccgaccg ctgcgcctta tccggtaact atcgtcttga 6180
gtccaacccg gtaagacacg acttatcgcc actggcagca gccactggta acaggattag 6240
cagagcgagg tatgtaggcg gtgctacaga gttcttgaag tggtggccta actacggcta 6300
cactagaagg acagtatttg gtatctgcgc tctgctgaag ccagttacct tcggaaaaag 6360
agttggtagc tcttgatccg gcaaacaaac caccgctggt agcggtggtt tttttgtttg 6420
caagcagcag attacgcgca gaaaaaaagg atctcaagaa gatcctttga tcttttctac 6480
ggggtctgac gctcagtgga acgaaaactc acgttaaggg attttggtca tgagatc 6537

<210> SEQ ID NO 64
<211> LENGTH: 7046
<212> TYPE: DNA
<213> ORGANISM: artificial sequence
<220> FEATURE:
<223> OTHER INFORMATION: final expression vector containg TLR9 and CD32 binding regions and epitope sequence

<400> SEQUENCE: 64
agatctaaca tccaaagacg aaaggttgaa tgaaaccttt ttgccatccg acatccacag 60
gtccattctc acacataagt gccaaacgca acaggagggg atacactagc agcagaccgt 120
tgcaaacgca ggacctccac tcctcttctc ctcaacaccc acttttgcca tcgaaaaacc 180
agcccagtta ttgggcttga ttggagctcg ctcattccaa ttccttctat taggctacta 240
acaccatgac tttattagcc tgtctatcct ggcccccctg gcgaggttca tgtttgttta 300
tttccgaatg caacaagctc cgcattacac ccgaacatca ctccagatga gggctttctg 360
agtgtggggt caaatagttt catgttcccc aaatggccca aaactgacag tttaaacgct 420
gtcttggaac ctaatatgac aaaagcgtga tctcatccaa gatgaactaa gtttggttcg 480
ttgaaatgct aacggccagt tggtcaaaaa gaaacttcca aaagtcggca taccgtttgt 540
cttgtttggt attgattgac gaatgctcaa aaataatctc attaatgctt agcgcagtct 600
ctctatcgct tctgaacccc ggtgcacctg tgccgaaacg caaatgggga aacacccgct 660
ttttggatga ttatgcattg tctccacatt gtatgcttcc aagattctgg tgggaatact 720
gctgatagcc taacgttcat gatcaaaatt taactgttct aacccctact tgacagcaat 780
atataaacag aaggaagctg ccctgtctta aacctttttt tttatcatca ttattagctt 840
actttcataa ttgcgactgg ttccaattga caagcttttg attttaacga cttttaacga 900
caacttgaga agatcaaaaa acaactaatt attcgaaacg atgagatttc cttcaatttt 960
tactgctgtt ttattcgcag catcctccgc attagctgct ccagtcaaca ctacaacaga 1020
agatgaaacg gcacaaattc cggctgaagc tgtcatcggt tactcagatt tagaagggga 1080
tttcgatgtt gctgttttgc cattttccaa cagcacaaat aacgggttat tgtttataaa 1140
tactactatt gccagcattg ctgctaaaga agaaggggta tctctcgaga aaagagaggc 1200
tgaagctgaa ttcgaggttc agcttcagca gtctggacct gagctgaaga agcctggaga 1260
gacagtcaag atctcctgca aggcttctgg gtataccttc acaaactatg gaatgaactg 1320
ggtgaagcag gctccaggaa agggtttaaa gtggatgggc tggttaaaca cctacactgg 1380
agagtcaata tatcctgatg acttcaaggg acggtttgcc ttctcttcgg aaacctctgc 1440
cagcactgcc tatttgcaga tcaacaacct caaaaatgag gacatggcta catatttctg 1500
tgcaagaggg gactatggtt acgacgaccc tttggactac tggggtcaag gaacctcagt 1560
caccgtctcc tcagccaaaa ctcgagaacc acaggtgtac accctgcccc catcccggga 1620

```
tgagctgggc atcgcgcaag tcagcctgac ctgcctggtc aaaggcttct atcccagcga   1680
catcgccgtg gagtgggaga gcaacgggca gccggagaac aactacaaga ccacgcctcc   1740
cgtgctggac tccgacggct ctttcttcct ctacagcaag cttaccgtgt tgggccgcag   1800
gtggaccctg ggaacgtct tctcatgctc cgtgatgcat gaggctctgc acaaccacta   1860
cacgcagaag agcctctccc tgtctccggg taaatctcta gaacaaaaac tcatctcaga   1920
agaggatctg aatagcgccg tcgaccatca tcatcatcat cattgagttt gtagccttag   1980
acatgactgt tcctcagttc aagttgggca cttacgagaa gaccggtctt gctagattct   2040
aatcaagagg atgtcagaat gccatttgcc tgagagatgc aggcttcatt tttgatactt   2100
ttttatttgt aacctatata gtataggatt ttttttgtca ttttgtttct tctcgtacga   2160
gcttgctcct gatcagccta tctcgcagct gatgaatatc ttgtggtagg ggtttgggaa   2220
aatcattcga gtttgatgtt tttcttggta tttcccactc ctcttcagag tacagaagat   2280
taagtgagac cttcgtttgt gcagatccaa catccaaaga cgaaaggttg aatgaaacct   2340
ttttgccatc cgacatccac aggtccattc tcacacataa gtgccaaacg caacaggagg   2400
ggatacacta gcagcagacc gttgcaaacg caggacctcc actcctcttc tcctcaacac   2460
ccacttttgc catcgaaaaa ccagcccagt tattgggctt gattggagct cgctcattcc   2520
aattccttct attaggctac taacaccatg actttattag cctgtctatc ctggcccccc   2580
tggcgaggtt catgtttgtt tatttccgaa tgcaacaagc tccgcattac acccgaacat   2640
cactccagat gagggctttc tgagtgtggg gtcaaatagt ttcatgttcc ccaaatggcc   2700
caaaactgac agtttaaacg ctgtcttgga acctaatatg acaaaagcgt gatctcatcc   2760
aagatgaact aagtttggtt cgttgaaatg ctaacggcca gttggtcaaa aagaaacttc   2820
caaaagtcgg cataccgttt gtcttgtttg gtattgattg acgaatgctc aaaaataatc   2880
tcattaatgc ttagcgcagt ctctctatcg cttctgaacc ccggtgcacc tgtgccgaaa   2940
cgcaaatggg gaaacacccg ctttttggat gattatgcat tgtctccaca ttgtatgctt   3000
ccaagattct ggtgggaata ctgctgatag cctaacgttc atgatcaaaa tttaactgtt   3060
ctaacccccta cttgacagca atatataaac agaaggaagc tgccctgtct taaacctttt   3120
tttttatcat cattattagc ttactttcat aattgcgact ggttccaatt gacaagcttt   3180
tgattttaac gacttttaac gacaacttga gaagatcaaa aaacaactaa ttattcgaaa   3240
cgatgagatt tccttcaatt tttactgctg ttttattcgc agcatcctcc gcattagctg   3300
ctccagtcaa cactacaaca gaagatgaaa cggcacaaat tccggctgaa gctgtcatcg   3360
gttactcaga tttagaaggg gatttcgatg ttgctgtttt gccattttcc aacagcacaa   3420
ataacgggtt attgtttata aatactacta ttgccagcat tgctgctaaa gaagaagggg   3480
tatctctcga gaaaagagag gctgaagctg aattcgacat tgtgatgacc caggctgcac   3540
cctctgtacc tgtcactcct ggagagtcag tatccatctc ctgcaggtct agtaagagtc   3600
tcctgcatac taatggcaac acttacttgc attggttcct acagaggcca ggccagtctc   3660
ctcagctcct gatatatcgg atgtccgtcc ttgcctcagg agtcccagac aggttcagtg   3720
gcagtgggtc aggaactgct ttcacactga gcatcagtag agtggaggct gaggatgtgg   3780
gtgtttttta ctgtatgcaa catctagaat atccgctcac gttcggtgct gggaccaagc   3840
tggaactgaa acgggctcct cgagaaccac aggtgtacac cctgccccca tcccgggatg   3900
agctgggcat cgcgcaagtc agcctgacct gcctggtcaa aggcttctat cccagcgaca   3960
```

```
tcgccgtgga gtgggagagc aacgggcagc cggagaacaa ctacaagacc acgcctcccg   4020
tgctggactc cgacggctct ttcttcctct acagcaagct taccgtgttg ggccgcaggt   4080
ggaccctggg gaacgtcttc tcatgctccg tgatgcatga ggctctgcac aaccactaca   4140
cgcagaagag cctctccctg tctccgggta aagggcgcgc ctccggatgc caaatttacc   4200
cgccaaacgc gaacaagatc agagaggctt tgcaatcttg caggaggccc aatgcgcaga   4260
gattcggcat atccaactac tgccagatct accccccata cgatgggcgt acaatcatac   4320
agcgtgataa cggctatcag cctaactacc acgccgtgaa catcgtcggc tacgagaatg   4380
tcgtggttac tgtgaaggta atgggcgatg acggggttct agcttgcgcc atagctacca   4440
agtacacttg gaacgtaccc aaaattgcgc cgaaaagtga aaacgtcgta gtgaccataa   4500
gggaggcatt ggctcaacct caaagatact gcagacacta ctggacgccc tgcataatcc   4560
accgtggtaa accctttcaa cttgaggcag tgttcgaagc taacaggacg gtaacgccaa   4620
ttcgtatgca aggtgggtgc gggtcttgtt gggctttttc tggtgtggct gctactgaat   4680
aaggcgcgcc tgaggtacct cgagccgcgg cggccgccag ctttctagaa caaaaactca   4740
tctcagaaga ggatctgaat agcgccgtcg accatcatca tcatcatcat tgagtttgta   4800
gccttagaca tgactgttcc tcagttcaag ttgggcactt acgagaagac cggtcttgct   4860
agattctaat caagaggatg tcagaatgcc atttgcctga gagatgcagg cttcattttt   4920
gatacttttt tatttgtaac ctatatagta taggattttt tttgtcattt tgtttcttct   4980
cgtacgagct tgctcctgat cagcctatct cgcagctgat gaatatcttg tggtaggggt   5040
ttgggaaaat cattcgagtt tgatgttttt cttggtattt cccactcctc ttcagagtac   5100
agaagattaa gtgagacctt cgtttgtgcg gatcccccac acaccatagc ttcaaaatgt   5160
ttctactcct tttttactct tccagatttt ctcggactcc gcgcatcgcc gtaccacttc   5220
aaaacaccca agcacagcat actaaatttt ccctctttct tcctctaggg tgtcgttaat   5280
tacccgtact aaaggtttgg aaaagaaaaa agagaccgcc tcgtttcttt ttcttcgtcg   5340
aaaaaggcaa taaaaatttt tatcacgttt ctttttcttg aaattttttt ttttagtttt   5400
tttctctttc agtgacctcc attgatattt aagttaataa acggtcttca atttctcaag   5460
tttcagtttc atttttcttg ttctattaca actttttttta cttcttgttc attagaaaga   5520
aagcatagca atctaatcta aggggcggtg ttgacaatta atcatcggca tagtatatcg   5580
gcatagtata atacgacaag gtgaggaact aaaccatggc caagttgacc agtgccgttc   5640
cggtgctcac cgcgcgcgac gtcgccggag cggtcgagtt ctggaccgac cggctcgggt   5700
tctcccggga cttcgtggag gacgacttcg ccggtgtggt ccgggacgac gtgaccctgt   5760
tcatcagcgc ggtccaggac caggtggtgc cggacaacac cctggcctgg gtgtgggtgc   5820
gcggcctgga cgagctgtac gccgagtggt cggaggtcgt gtccacgaac ttccgggacg   5880
cctccgggcc ggccatgacc gagatcggcg agcagccgtg gggcgggag ttcgccctgc   5940
gcgacccggc cggcaactgc gtgcacttcg tggccgagga gcaggactga cacgtccgac   6000
ggcggcccac gggtcccagg cctcggagat ccgtccccct tttcctttgt cgatatcatg   6060
taattagtta tgtcacgctt acattcacgc cctcccccca catccgctct aaccgaaaag   6120
gaaggagtta gacaacctga agtctaggtc cctatttatt tttttatagt tatgttagta   6180
ttaagaacgt tatttatatt tcaaattttt cttttttttc tgtacagacg cgtgtacgca   6240
tgtaacatta tactgaaaac cttgcttgag aaggttttgg gacgctcgaa ggctttaatt   6300
tgcaagctgg agaccaacat gtgagcaaaa ggccagcaaa aggccaggaa ccgtaaaaag   6360
```

```
gccgcgttgc tggcgttttt ccataggctc cgcccccctg acgagcatca caaaaatcga   6420

cgctcaagtc agaggtggcg aaacccgaca ggactataaa gataccaggc gtttccccct   6480

ggaagctccc tcgtgcgctc tcctgttccg accctgccgc ttaccggata cctgtccgcc   6540

tttctccctt cgggaagcgt ggcgctttct caatgctcac gctgtaggta tctcagttcg   6600

gtgtaggtcg ttcgctccaa gctgggctgt gtgcacgaac cccccgttca gcccgaccgc   6660

tgcgccttat ccggtaacta tcgtcttgag tccaacccgg taagacacga cttatcgcca   6720

ctggcagcag ccactggtaa caggattagc agagcgaggt atgtaggcgg tgctacagag   6780

ttcttgaagt ggtggcctaa ctacggctac actagaagga cagtatttgg tatctgcgct   6840

ctgctgaagc cagttacctt cggaaaaaga gttggtagct cttgatccgg caaacaaacc   6900

accgctggta gcggtggttt ttttgtttgc aagcagcaga ttacgcgcag aaaaaaagga   6960

tctcaagaag atcctttgat cttttctacg gggtctgacg ctcagtggaa cgaaaactca   7020

cgttaaggga ttttggtcat gagatc                                        7046


<210> SEQ ID NO 65
<211> LENGTH: 12
<212> TYPE: PRT
<213> ORGANISM: Homo sapiens

<400> SEQUENCE: 65

Lys Arg Ala Asp Ala Ala Pro Thr Val Ser Ile Phe
1               5                   10


<210> SEQ ID NO 66
<211> LENGTH: 36
<212> TYPE: DNA
<213> ORGANISM: Homo sapiens

<400> SEQUENCE: 66

aaacgggctg atgctgcacc aactgtatcc atcttc                               36


<210> SEQ ID NO 67
<211> LENGTH: 250
<212> TYPE: PRT
<213> ORGANISM: Artificial sequence
<220> FEATURE:
<223> OTHER INFORMATION: ScFV

<400> SEQUENCE: 67

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Gly Ser Gly Gly Gly
        115                 120                 125
```

```
Gly Ser Gly Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
145                 150                 155                 160

Ser Lys Ser Leu Leu His Thr Asn Gly Asn Thr Tyr Leu His Trp Phe
                165                 170                 175

Leu Gln Arg Pro Gly Gln Ser Pro Gln Leu Leu Ile Tyr Arg Met Ser
            180                 185                 190

Val Leu Ala Ser Gly Val Pro Asp Arg Phe Ser Gly Ser Gly Ser Gly
        195                 200                 205

Thr Ala Phe Thr Leu Ser Ile Ser Arg Val Glu Ala Glu Asp Val Gly
    210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Ser Ile
                245                 250


<210> SEQ ID NO 68
<211> LENGTH: 19
<212> TYPE: PRT
<213> ORGANISM: Artificial sequence
<220> FEATURE:
<223> OTHER INFORMATION: synthesized

<400> SEQUENCE: 68

Ala Asp Gly Ala Trp Ala Trp Val Trp Leu Thr Glu Thr Ala Val Gly
1               5                   10                  15

Ala Ala Lys


<210> SEQ ID NO 69
<211> LENGTH: 249
<212> TYPE: PRT
<213> ORGANISM: Artificial sequence
<220> FEATURE:
<223> OTHER INFORMATION: ScFV

<400> SEQUENCE: 69

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
                85                  90                  95

Tyr Cys Asn Arg Arg Asp Glu Tyr Tyr Ala Met Asp Tyr Trp Gly Gln
            100                 105                 110

Gly Thr Ser Val Ser Val Ser Ser Gly Gly Gly Gly Ser Gly Gly Gly
        115                 120                 125

Gly Ser Gly Gly Gly Gly Ser Asp Ile Val Leu Thr Gln Ser Pro Gly
    130                 135                 140

Ser Leu Ala Val Ser Leu Gly Gln Arg Ala Thr Ile Ser Cys Arg Ala
145                 150                 155                 160
```

```
Ser Glu Ser Val Asp Asn Phe Gly Ile Ser Phe Met Asn Trp Phe Gln
                165                 170                 175

Gln Lys Pro Gly Gln Pro Pro Arg Leu Leu Ile Tyr Gly Ala Ser Asn
            180                 185                 190

Gln Gly Ser Gly Val Pro Ala Arg Phe Ser Gly Ser Gly Ser Gly Thr
        195                 200                 205

Asp Phe Ser Leu Asn Ile His Pro Val Glu Glu Asp Asp Ala Ala Met
    210                 215                 220

Tyr Phe Cys Gln Gln Ser Lys Glu Val Pro Trp Thr Phe Gly Gly Gly
225                 230                 235                 240

Thr Lys Leu Glu Ile Lys Gly Ser Ile
                245


<210> SEQ ID NO 70
<211> LENGTH: 230
<212> TYPE: PRT
<213> ORGANISM: Artificial sequence
<220> FEATURE:
<223> OTHER INFORMATION: Fc fragment

<400> SEQUENCE: 70

Pro Lys Ser Cys Asp Lys Thr His Thr Cys Pro Pro Cys Pro Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
    210                 215                 220

Ser Leu Ser Pro Gly Lys
225                 230


<210> SEQ ID NO 71
<211> LENGTH: 20
<212> TYPE: DNA
<213> ORGANISM: Artificial sequence
```

<220> FEATURE:
<223> OTHER INFORMATION: CpG

<400> SEQUENCE: 71
gggggacgat cgtcgggggg 20

<210> SEQ ID NO 72
<211> LENGTH: 24
<212> TYPE: DNA
<213> ORGANISM: Artificial sequence
<220> FEATURE:
<223> OTHER INFORMATION: CpG

<400> SEQUENCE: 72
tcgtcgtttt gtcgttttgt cgtt 24

<210> SEQ ID NO 73
<211> LENGTH: 12
<212> TYPE: PRT
<213> ORGANISM: Artificial sequence
<220> FEATURE:
<223> OTHER INFORMATION: synthesized

<400> SEQUENCE: 73

Glu Ser Trp Asp Lys Phe Leu Ser His Tyr Leu Pro
1 5 10

<210> SEQ ID NO 74
<211> LENGTH: 7
<212> TYPE: PRT
<213> ORGANISM: Artificial sequence
<220> FEATURE:
<223> OTHER INFORMATION: synthesized

<400> SEQUENCE: 74

Thr Asp Trp Ser Trp Phe Tyr
1 5

<210> SEQ ID NO 75
<211> LENGTH: 7
<212> TYPE: PRT
<213> ORGANISM: Artificial sequence
<220> FEATURE:
<223> OTHER INFORMATION: synthesized

<400> SEQUENCE: 75

Tyr Pro Val Tyr Trp Pro Trp
1 5

<210> SEQ ID NO 76
<211> LENGTH: 7
<212> TYPE: PRT
<213> ORGANISM: Artificial sequence
<220> FEATURE:
<223> OTHER INFORMATION: synthesized

<400> SEQUENCE: 76

Glu Trp Trp Phe Tyr Trp Pro
1 5

<210> SEQ ID NO 77
<211> LENGTH: 7
<212> TYPE: PRT
<213> ORGANISM: Artificial sequence
<220> FEATURE:
<223> OTHER INFORMATION: synthesized

<400> SEQUENCE: 77

Trp Phe Pro Ile Glu Trp Trp
1 5

<210> SEQ ID NO 78
<211> LENGTH: 7
<212> TYPE: PRT
<213> ORGANISM: Artificial sequence
<220> FEATURE:
<223> OTHER INFORMATION: synthesized

<400> SEQUENCE: 78

Asp Gln Val Asp Ile Gly Tyr
1 5

<210> SEQ ID NO 79
<211> LENGTH: 7
<212> TYPE: PRT
<213> ORGANISM: Artificial sequence
<220> FEATURE:
<223> OTHER INFORMATION: synthesized

<400> SEQUENCE: 79

Thr His Gln Val Tyr Ile Ser
1 5

<210> SEQ ID NO 80
<211> LENGTH: 11
<212> TYPE: PRT
<213> ORGANISM: Artificial sequence
<220> FEATURE:
<223> OTHER INFORMATION: synthesized

<400> SEQUENCE: 80

Trp Phe Pro Ile Glu Trp Trp Phe Tyr Trp Pro
1 5 10

<210> SEQ ID NO 81
<211> LENGTH: 12
<212> TYPE: PRT
<213> ORGANISM: Artificial sequence
<220> FEATURE:
<223> OTHER INFORMATION: synthesized

<400> SEQUENCE: 81

Asp Ser Trp Gln Ala Phe Leu Thr Lys Phe Val Leu
1 5 10

<210> SEQ ID NO 82
<211> LENGTH: 12
<212> TYPE: PRT
<213> ORGANISM: Artificial sequence
<220> FEATURE:
<223> OTHER INFORMATION: synthesized

<400> SEQUENCE: 82

His Asp Ile Gln Trp Phe Trp Gln His Trp Asn Ser
1 5 10

<210> SEQ ID NO 83
<211> LENGTH: 12
<212> TYPE: PRT
<213> ORGANISM: Artificial sequence
<220> FEATURE:
<223> OTHER INFORMATION: synthesized

<400> SEQUENCE: 83

Trp Ser Trp Trp Asp His Thr Phe Asn Tyr Met Leu
1 5 10

<210> SEQ ID NO 84
<211> LENGTH: 12
<212> TYPE: PRT
<213> ORGANISM: Artificial sequence
<220> FEATURE:
<223> OTHER INFORMATION: synthesized

<400> SEQUENCE: 84

Thr Thr Gln Gln Thr Trp Asn Val Arg Tyr Pro Tyr
1 5 10

<210> SEQ ID NO 85
<211> LENGTH: 12
<212> TYPE: PRT
<213> ORGANISM: Artificial sequence
<220> FEATURE:
<223> OTHER INFORMATION: synthesized

<400> SEQUENCE: 85

Asp His Thr Met Pro Trp Thr Arg Asn Ala Lys Asn
1 5 10

<210> SEQ ID NO 86
<211> LENGTH: 12
<212> TYPE: PRT
<213> ORGANISM: Artificial sequence
<220> FEATURE:
<223> OTHER INFORMATION: synthesized

<400> SEQUENCE: 86

Ser Trp Asp Pro Tyr Trp Pro Phe Pro Trp Phe Ser
1 5 10

<210> SEQ ID NO 87
<211> LENGTH: 12
<212> TYPE: PRT
<213> ORGANISM: Artificial sequence
<220> FEATURE:
<223> OTHER INFORMATION: synthesized

<400> SEQUENCE: 87

Ala Ile Tyr Tyr Val Pro Ser Pro Met Phe Thr Val
1 5 10

<210> SEQ ID NO 88
<211> LENGTH: 12
<212> TYPE: PRT
<213> ORGANISM: Artificial sequence
<220> FEATURE:
<223> OTHER INFORMATION: synthesized

<400> SEQUENCE: 88

Glu Thr Thr Leu Leu Lys Met Trp Leu Ala Gln Met
1 5 10

<210> SEQ ID NO 89
<211> LENGTH: 12
<212> TYPE: PRT
<213> ORGANISM: Artificial sequence
<220> FEATURE:
<223> OTHER INFORMATION: synthesized

<400> SEQUENCE: 89

```
Tyr Pro Trp Leu Asp Val Ala Val Val Ser Leu Tyr
1               5                   10


<210> SEQ ID NO 90
<211> LENGTH: 12
<212> TYPE: PRT
<213> ORGANISM: Artificial sequence
<220> FEATURE:
<223> OTHER INFORMATION: synthesized

<400> SEQUENCE: 90

Val Pro Gly Trp His Tyr Leu Ala Thr Leu Arg Ala
1               5                   10


<210> SEQ ID NO 91
<211> LENGTH: 12
<212> TYPE: PRT
<213> ORGANISM: Artificial sequence
<220> FEATURE:
<223> OTHER INFORMATION: synthesized

<400> SEQUENCE: 91

Phe Asp Pro Leu Gly Ser Arg Asp Ile Lys Gly Ser
1               5                   10


<210> SEQ ID NO 92
<211> LENGTH: 25
<212> TYPE: DNA
<213> ORGANISM: Artificial sequence
<220> FEATURE:
<223> OTHER INFORMATION: CpG

<400> SEQUENCE: 92

tcgtcgtcgt tcgaacgacg ttgat                                            25


<210> SEQ ID NO 93
<211> LENGTH: 297
<212> TYPE: PRT
<213> ORGANISM: Artificial sequence
<220> FEATURE:
<223> OTHER INFORMATION: ScFV

<400> SEQUENCE: 93

Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Leu Asn Thr Tyr Thr Gly Glu Ser Ile Tyr Pro Asp Asp Phe
    50                  55                  60

Lys Gly Arg Phe Ala Phe Ser Ser Glu Thr Ser Ala Ser Thr Ala Tyr
65                  70                  75                  80

Leu Gln Ile Asn Asn Leu Lys Asn Glu Asp Met Ala Thr Tyr Phe Cys
                85                  90                  95

Ala Arg Gly Asp Tyr Gly Tyr Asp Asp Pro Leu Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Met Thr Gln Ala Ala Pro
    130                 135                 140

Ser Val Pro Val Thr Pro Gly Glu Ser Val Ser Ile Ser Cys Arg Ser
```

```
145                 150                 155                 160

Ser Lys Ser Leu Leu His Thr Asn Gly Asn Thr Tyr Leu His Trp Phe
                165                 170                 175

Leu Gln Arg Pro Gly Gln Ser Pro Gln Leu Leu Ile Tyr Arg Met Ser
            180                 185                 190

Val Leu Ala Ser Gly Val Pro Asp Arg Phe Ser Gly Ser Gly Ser Gly
        195                 200                 205

Thr Ala Phe Thr Leu Ser Ile Ser Arg Val Glu Ala Glu Asp Val Gly
    210                 215                 220

Val Phe Tyr Cys Met Gln His Leu Glu Tyr Pro Leu Thr Phe Gly Ala
225                 230                 235                 240

Gly Thr Lys Leu Glu Leu Lys Gly Ser Ile Ser Ala Trp Ser His Pro
                245                 250                 255

Gln Phe Glu Lys Gly Pro Glu Val Ser Ala Leu Glu Lys Glu Val Ser
            260                 265                 270

Ala Leu Glu Lys Glu Val Ser Ala Leu Glu Lys Glu Val Ser Ala Leu
        275                 280                 285

Glu Lys Glu Val Ser Ala Leu Glu Lys
    290                 295


<210> SEQ ID NO 94
<211> LENGTH: 296
<212> TYPE: PRT
<213> ORGANISM: Artificial sequence
<220> FEATURE:
<223> OTHER INFORMATION: ScFV

<400> SEQUENCE: 94

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Tyr Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Ala Thr His Tyr Ala Glu
    50                  55                  60

Ser Val Lys Gly Arg Phe Thr Ile Ser Arg Asp Asp Ser Lys Asn Asn
65                  70                  75                  80

Val Tyr Leu Gln Met Asn Asn Leu Arg Ala Glu Asp Thr Gly Ile Tyr
                85                  90                  95

Tyr Cys Asn Arg Arg Asp Glu Tyr Tyr Ala Met Asp Tyr Trp Gly Gln
            100                 105                 110

Gly Thr Ser Val Ser Val Ser Ser Gly Gly Gly Gly Ser Gly Gly Gly
        115                 120                 125

Gly Ser Gly Gly Gly Gly Ser Asp Ile Val Leu Thr Gln Ser Pro Gly
    130                 135                 140

Ser Leu Ala Val Ser Leu Gly Gln Arg Ala Thr Ile Ser Cys Arg Ala
145                 150                 155                 160

Ser Glu Ser Val Asp Asn Phe Gly Ile Ser Phe Met Asn Trp Phe Gln
                165                 170                 175

Gln Lys Pro Gly Gln Pro Pro Arg Leu Leu Ile Tyr Gly Ala Ser Asn
            180                 185                 190

Gln Gly Ser Gly Val Pro Ala Arg Phe Ser Gly Ser Gly Ser Gly Thr
        195                 200                 205

Asp Phe Ser Leu Asn Ile His Pro Val Glu Glu Asp Asp Ala Ala Met
```

```
    210                 215                 220

Tyr Phe Cys Gln Gln Ser Lys Glu Val Pro Trp Thr Phe Gly Gly Gly
225                 230                 235                 240

Thr Lys Leu Glu Ile Lys Gly Ser Ile Ser Ala Trp Ser His Pro Gln
                245                 250                 255

Phe Glu Lys Gly Pro Glu Val Ser Ala Leu Glu Lys Glu Val Ser Ala
            260                 265                 270

Leu Glu Lys Glu Val Ser Ala Leu Glu Lys Glu Val Ser Ala Leu Glu
        275                 280                 285

Lys Glu Val Ser Ala Leu Glu Lys
    290                 295


<210> SEQ ID NO 95
<211> LENGTH: 56
<212> TYPE: PRT
<213> ORGANISM: Artificial sequence
<220> FEATURE:
<223> OTHER INFORMATION: Immunogen-coil

<400> SEQUENCE: 95

Ala Asp Gly Ala Trp Ala Trp Val Trp Leu Thr Glu Thr Ala Val Gly
1               5                   10                  15

Ala Ala Lys Gly Pro Glu Val Ser Ala Leu Glu Lys Glu Val Ser Ala
            20                  25                  30

Leu Glu Lys Glu Val Ser Ala Leu Glu Lys Glu Val Ser Ala Leu Glu
        35                  40                  45

Lys Glu Val Ser Ala Leu Glu Lys
    50                  55


<210> SEQ ID NO 96
<211> LENGTH: 267
<212> TYPE: PRT
<213> ORGANISM: Artificial sequence
<220> FEATURE:
<223> OTHER INFORMATION: Fc fragment-coil

<400> SEQUENCE: 96

Pro Lys Ser Cys Asp Lys Thr His Thr Cys Pro Pro Cys Pro Pro Glu
1               5                   10                  15

Leu Leu Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160
```

Ala Val Glu Trp Glu Ser Asn Gly Gln Pro Glu Asn Asn Tyr Lys Thr
165 170 175

Thr Pro Pro Val Leu Asp Ser Asp Gly Ser Phe Phe Leu Tyr Ser Lys
180 185 190

Leu Thr Val Asp Lys Ser Arg Trp Gln Gln Gly Asn Val Phe Ser Cys
195 200 205

Ser Val Met His Glu Ala Leu His Asn His Tyr Thr Gln Lys Ser Leu
210 215 220

Ser Leu Ser Pro Gly Lys Gly Pro Glu Val Ser Ala Leu Glu Lys Glu
225 230 235 240

Val Ser Ala Leu Glu Lys Glu Val Ser Ala Leu Glu Lys Glu Val Ser
245 250 255

Ala Leu Glu Lys Glu Val Ser Ala Leu Glu Lys
260 265

<210> SEQ ID NO 97
<211> LENGTH: 253
<212> TYPE: PRT
<213> ORGANISM: Artificial sequence
<220> FEATURE:
<223> OTHER INFORMATION: Immunogen-coil

<400> SEQUENCE: 97

His His His His His His Tyr Tyr Arg Tyr Val Ala Arg Glu Gln Ser
1 5 10 15

Cys Arg Arg Pro Asn Ala Gln Arg Phe Gly Ile Ser Asn Tyr Cys Gln
20 25 30

Ile Tyr Pro Pro Asn Val Asn Lys Ile Arg Glu Ala Leu Ala Gln Thr
35 40 45

His Ser Ala Ile Ala Val Asp Leu Arg Gln Met Arg Thr Val Thr Pro
50 55 60

Ile Arg Met Gln Gly Gly Cys Gly Ser Cys Trp Ala Phe Ser Gly Val
65 70 75 80

Ala Ala Thr Glu Ser Ala Tyr Leu Gln Gln Tyr Asp Ile Lys Tyr Thr
85 90 95

Trp Asn Val Pro Lys Ile Ala Pro Lys Ser Glu Asn Val Val Val Thr
100 105 110

Val Lys Val Met Gly Asp Asp Gly Val Leu Ala Cys Ala Ile Ala Thr
115 120 125

His Ala Lys Ile Arg Asp Asp Ala Phe Arg His Tyr Asp Gly Arg Thr
130 135 140

Ile Ile Gln Arg Asp Asn Gly Tyr Gln Pro Asn Tyr His Ala Val Asn
145 150 155 160

Ile Val Gly Tyr Ser Asn Ala Gln Gly Val Asp Tyr Trp Ile Val Arg
165 170 175

Asn Ser Trp Asp Thr Asn Trp His Glu Ile Lys Lys Val Leu Val Pro
180 185 190

Gly Cys His Gly Ser Glu Pro Cys Ile Ile His Arg Gly Lys Pro Phe
195 200 205

Gly Gly Gly Ser Gly Gly Gly Ser Gly Gly Lys Val Ser Ala Leu Lys
210 215 220

Glu Lys Val Ser Ala Leu Lys Glu Lys Val Ser Ala Leu Lys Glu Lys
225 230 235 240

Val Ser Ala Leu Lys Glu Lys Val Ser Ala Leu Lys Glu
245 250

<210> SEQ ID NO 98
<211> LENGTH: 415
<212> TYPE: PRT
<213> ORGANISM: Artificial sequence
<220> FEATURE:
<223> OTHER INFORMATION: Immunogen-coil

<400> SEQUENCE: 98

```
Gly Val Leu Ala Cys Ala Ile Ala Thr His Ala Lys Ile Arg Glu Gln
1               5                   10                  15

Glu Arg Leu Val Lys Leu Glu Thr Val Lys Lys Ser Leu Glu Gln Glu
            20                  25                  30

Val Arg Thr Leu His Val Arg Ile Glu Glu Val Glu Ala Asn Ala Leu
        35                  40                  45

Ala Gly Gly Asp Leu Arg Gln Met Arg Thr Val Thr Pro Ile Arg Met
    50                  55                  60

Gln Gly Gly Cys Gly Ser Cys Trp Glu Ala His Glu Gln Gln Ile Arg
65                  70                  75                  80

Ile Met Thr Thr Lys Leu Lys Glu Ala Glu Ala Arg Gln Gln Tyr Asp
                85                  90                  95

Ile Lys Tyr Thr Trp Asn Val Pro Lys Ile Ala Val Asn Ile Val Gly
            100                 105                 110

Tyr Ser Asn Ala Gln Gly Val Asp Tyr Trp Ile Val Arg Asn Ser Trp
        115                 120                 125

Asp Thr Asn Trp Tyr His Asn Pro His Phe Ile Gly Asn Arg Ser Val
    130                 135                 140

Ile Thr His Leu Met Glu Asp Leu Lys Gly Glu Leu Asp Met Arg Asn
145                 150                 155                 160

Ile Gln Val Arg Gly Leu Lys Gln Met Lys Arg Val Gly Asp Ala Asn
                165                 170                 175

Val Lys Ser Glu Asp Asp Ala Phe Arg His Tyr Asp Gly Arg Thr Ile
            180                 185                 190

Ile Gln Arg Asp Asn Gly Tyr Gln Pro Asn Tyr Leu Asp Glu Tyr Trp
        195                 200                 205

Ile Leu Thr Ala Ala His Cys Val Asp Gly Gln Thr Val Ser Lys Leu
    210                 215                 220

Ile Arg Ser Lys Val Leu Gly Glu Lys Ile Ser Tyr Tyr Arg Tyr Val
225                 230                 235                 240

Ala Arg Glu Gln Ser Cys Arg Arg Pro Asn Ala Gln Arg Phe Gly Ile
                245                 250                 255

Ser Asn Tyr Cys Val Val Val Thr Val Lys Val Met Gly Asp Asp Glu
            260                 265                 270

Leu His Thr Tyr Phe Asn Val Asn Tyr Thr Met His Tyr Tyr Leu Asn
        275                 280                 285

Asn Gly Ala Thr Arg Asp Ile Leu Asp Glu Tyr Trp Ile Leu Thr Ala
    290                 295                 300

Ala His Cys Val Ala Gly Gln Thr Ala Ser Lys Leu Ser Ile Arg Tyr
305                 310                 315                 320

Asn Ser Leu Lys His Ser Leu Phe Lys Tyr Arg Pro Phe Lys Val Asn
                325                 330                 335

Glu Leu Asn Leu Glu Gly Glu Phe Gly Arg Glu Leu Gln His Lys Phe
            340                 345                 350

Arg Leu Met Arg Asn Ser Gln Met Glu Val Glu Glu Gly Gly Gly Ser
        355                 360                 365
```

His His His His His His Gly Gly Gly Ser Gly Gly Lys Val Ser Ala
370 375 380

Leu Lys Glu Lys Val Ser Ala Leu Lys Glu Lys Val Ser Ala Leu Lys
385 390 395 400

Glu Lys Val Ser Ala Leu Lys Glu Lys Val Ser Ala Leu Lys Glu
405 410 415

<210> SEQ ID NO 99
<211> LENGTH: 10
<212> TYPE: PRT
<213> ORGANISM: Artificial sequence
<220> FEATURE:
<223> OTHER INFORMATION: synthesized

<400> SEQUENCE: 99

Ser Ala Trp Ser His Pro Gln Phe Glu Lys
1 5 10

<210> SEQ ID NO 100
<211> LENGTH: 35
<212> TYPE: PRT
<213> ORGANISM: Artificial sequence
<220> FEATURE:
<223> OTHER INFORMATION: synthesized

<400> SEQUENCE: 100

Glu Val Ser Ala Leu Glu Lys Glu Val Ser Ala Leu Glu Lys Glu Val
1 5 10 15

Ser Ala Leu Glu Lys Glu Val Ser Ala Leu Glu Lys Glu Val Ser Ala
20 25 30

Leu Glu Lys
35

<210> SEQ ID NO 101
<211> LENGTH: 7
<212> TYPE: PRT
<213> ORGANISM: Artificial sequence
<220> FEATURE:
<223> OTHER INFORMATION: synthesized

<400> SEQUENCE: 101

Glu Trp Trp Phe Tyr Trp Pro
1 5

<210> SEQ ID NO 102
<211> LENGTH: 3
<212> TYPE: PRT
<213> ORGANISM: Artificial sequence
<220> FEATURE:
<223> OTHER INFORMATION: synthesized

<400> SEQUENCE: 102

Glu Trp Trp
1

<210> SEQ ID NO 103
<211> LENGTH: 3
<212> TYPE: PRT
<213> ORGANISM: Artificial sequence
<220> FEATURE:
<223> OTHER INFORMATION: synthesized

<400> SEQUENCE: 103

Trp Phe Tyr
1

-continued

```
<210> SEQ ID NO 104
<211> LENGTH: 3
<212> TYPE: PRT
<213> ORGANISM: Artificial sequence
<220> FEATURE:
<223> OTHER INFORMATION: synthesized

<400> SEQUENCE: 104

Tyr Trp Pro
1


<210> SEQ ID NO 105
<211> LENGTH: 4
<212> TYPE: PRT
<213> ORGANISM: Artificial sequence
<220> FEATURE:
<223> OTHER INFORMATION: synthesized
<220> FEATURE:
<221> NAME/KEY: synthesized
<222> LOCATION: (3)..(3)
<223> OTHER INFORMATION: Xaa can be any amino acid

<400> SEQUENCE: 105

Gln Val Xaa Ile
1
```